United States Patent
Ngo et al.

(10) Patent No.: US 9,540,357 B1
(45) Date of Patent: Jan. 10, 2017

(54) 15-ARYL PROSTAGLANDINS AS EP4 AGONISTS, AND METHODS OF USE THEREOF

(71) Applicant: Allergan, Inc., Irvine, CA (US)

(72) Inventors: Vinh X. Ngo, Huntington Beach, CA (US); David W. Old, Irvine, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/501,760

(22) Filed: Sep. 30, 2014

Related U.S. Application Data

(60) Provisional application No. 62/031,615, filed on Jul. 31, 2014.

(51) Int. Cl.
  *C07D 207/27* (2006.01)
  *C07D 409/06* (2006.01)

(52) U.S. Cl.
  CPC .......... *C07D 409/06* (2013.01); *C07D 207/27* (2013.01)

(58) Field of Classification Search
  CPC . C07D 207/267; C07D 207/27; C07D 207/26; C07D 207/273; C07D 207/24
  USPC .................. 548/543, 527; 514/422
  See application file for complete search history.

(56) References Cited

U.S. PATENT DOCUMENTS

| | | |
|---|---|---|
| 6,552,067 B2 | 4/2003 | Cameron |
| 6,747,054 B2 | 6/2004 | Cameron |
| 7,192,979 B2 | 3/2007 | Cameron |
| 7,256,211 B1 | 8/2007 | Kambe |
| 7,414,071 B2 | 8/2008 | Cameron |
| 7,427,685 B2 | 9/2008 | Donde |
| 7,592,366 B2 | 9/2009 | Old |
| 7,662,850 B2 | 2/2010 | Old |
| 7,737,140 B2 | 6/2010 | Old |
| 7,786,117 B2 | 8/2010 | Old |
| 7,820,661 B2 | 10/2010 | Old |
| 7,947,732 B2 | 5/2011 | Old |
| 7,964,595 B2 | 6/2011 | Johnson |
| 7,998,998 B2 | 8/2011 | Old |
| 8,124,648 B2 | 2/2012 | Old |
| 8,252,788 B2 | 8/2012 | Old |
| 8,377,984 B2 | 2/2013 | Old |
| 8,592,413 B2 | 11/2013 | Gac |
| 2004/0142969 A1 | 7/2004 | Elworthy |
| 2005/0124577 A1 | 6/2005 | Tani |
| 2006/0167081 A1 | 7/2006 | Billot |
| 2009/0270392 A1 | 10/2009 | Old |
| 2009/0270396 A1 | 10/2009 | Old |
| 2009/0281171 A1 | 11/2009 | Old |
| 2009/0318449 A1 | 12/2009 | Old |
| 2011/0172299 A1 | 7/2011 | Gac |
| 2011/0178084 A1 | 7/2011 | Old |

FOREIGN PATENT DOCUMENTS

| | | | | |
|---|---|---|---|---|
| EP | 1707208 A1 | * | 10/2006 | |
| WO | WO0242268 | | 5/2002 | |
| WO | WO03074483 A1 | | 9/2003 | |
| WO | WO 03077910 A1 | * | 9/2003 | ......... A61K 31/4015 |
| WO | WO 2004037786 A2 | * | 5/2004 | |
| WO | WO2007014454 A1 | | 2/2007 | |
| WO | WO2008008718 A2 | | 1/2008 | |
| WO | WO2009055289 A2 | | 4/2009 | |
| WO | WO2009091765 A1 | | 7/2009 | |
| WO | WO2009097223 A1 | | 8/2009 | |
| WO | WO2011091276 A1 | | 7/2011 | |

OTHER PUBLICATIONS

Iwanaga, K., M. Okada, T. Murata, M. Hori, and H. Ozaki "Prostaglandin E2 Promotes Wound-Induced Migration of Intestinal Subepithelial Myofibroblasts via EP2, EP3, and EP4 Prostanoid Receptor Activation" Journ. Pharm. Exper. Therap. (2012), 340 (3), pp. 604-611.*
Jonsson and Änggård Scand, J Clin Lab Invest, 29 289-296, 1972.
Jouvenaz et al., Biochim Biophys Acta, 202, 231-234, 1970.
Pentland and Needleman, J Clin Invest,77(1) 246-251,1986.
Evans et al., Prostaglandins Leukot Essent Fatty Acid 49: 777-781, 1993.
Li et al., Arch Otolaryngol Head Neck Surg, 126, 1337-1343, 2000.
T. Higuchi and V. Stella, Pro-drugs as Novel Delivery Systems, vol. 14 of the A.C.S. Symposium Series, 1987.
T. W. Greene et al., Protective Groups in organic Synthesis, 1991, Wiley New York.
Edward B. Roche, Bioreversible Carriers in Drug Design, 1987, American Pharmaceutical Association and Pergamon Press.
M. Caira et al., J. Pharmaceutical Sci., 93(3), 601-611, 2004.
E. C. van Tonder et al., AAPS PharmSciTech., 5(1), article 12, 2004.
A. L. Bingham et al., Chem. Commun., 603-604, 2001.
P. Stahl et al., Camille G. (eds.), Handbook of Pharmaceutical Salts. Properties Selection and Use., 2002, Zurich: Wiley-VCH.
S. Berge et al., Journal of Pharmaceutical Sciences, 1977, 66(1), 1-19.
P. Gould, International J. of Pharmaceutics,1986, 33, 201-217.
Anderson et al., The Practice of Medicinal Chemistry,1996, Academic Press, New York.
The Orange Book, Food & Drug Administration website at http://www.accessdata.fda.gov/scripts/cder/obt. Retrieved Jan. 27, 2015.
Elworthy et al., Lactams as EP4 prostanoid receptor subtype selective agonists., Part 1: 2-Pyrrolidinones—stereochemical and lower side chain optimization; Bioorg. Med Chem. Lett. 2004 14 pp. 1655-1659.

* cited by examiner

*Primary Examiner* — Alicia L Otton
*Assistant Examiner* — Sagar Patel
(74) *Attorney, Agent, or Firm* — Jonathan Bass

(57) ABSTRACT

The invention provides compositions and methods for reducing healing wounds and reducing scars and blemishes. The compositions and methods of the invention include at least one EP4 agonist set forth herein. Wounds and or scars that can be treated by the compositions and methods of the invention can arise from events such as surgery, trauma, disease, mechanical injury, burn, radiation, poisoning, and the like.

12 Claims, 1 Drawing Sheet

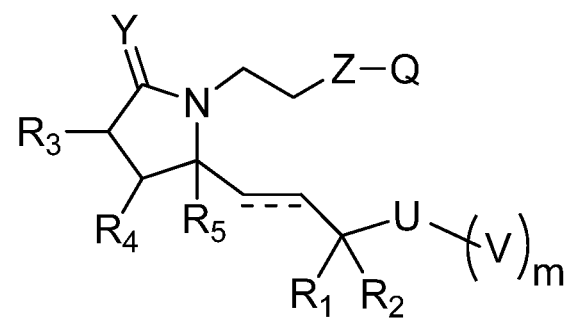
Formula I

15-ARYL PROSTAGLANDINS AS EP4 AGONISTS, AND METHODS OF USE THEREOF

RELATED APPLICATIONS

This application claims priority to U.S. Provisional Patent Application Ser. No. 62/031,615 filed on Jul. 31, 2014, the entire content of which is being incorporated herein by this specific reference.

FIELD OF THE INVENTION

The invention relates generally to compositions and methods for wound healing, and particularly to the use of EP4 agonists for treatment in wound healing, scar reduction, and skin repair.

BACKGROUND OF THE INVENTION

Prostanoid EP4 receptor is a G protein-coupled receptor that mediates the actions of prostaglandin E2 (PGE2) and is characterized by the longest intracellular C terminus loop when compared to other prostanoid receptors. The EP4 receptor is one of four receptor subtypes of prostaglandin E2 receptors. Mainly, EP4 receptors couple to G proteins and mediate elevations in cyclic-adenosine monophosphate ("cAMP") concentration, although they do participate in other pathways as well. There are some redundancies in function between EP2 and EP4 receptors. For example, both receptors induce PGE2-mediated RANKL through cAMP. However, EP2 is involved in cumulus expansion in ovulation and fertilization, whereas EP4 regulates closure of the ductus arteriosus. Expression of EP4 receptors is controlled by various physiological and pathophysiological processes as these receptors participate in ovulation and fertilization, induce bone formation, protect against inflammatory bowel disease, facilitate Langerhans cell migration and maturation and mediate joint inflammation in a model of collagen-induced arthritis, among others.

PGE2 represents the major prostaglandin in human and rat skin (Jonsson and Änggård, Scand J Clin Lab Invest, 29, 289-296, 1972; Jouvenaz et al, Biochim Biophys Acta, 202, 231-234, 1970). Studies of keratinocyte proliferation modulation indicate that PGE2 is a growth-promoting autocoid for the epidermis, and that epidermal PGE2 synthesis may be enhanced in wound healing and disease states characterized by the disruption of epidermal continuity (Pentland and Needleman, J Clin Invest, 77(1), 246-251, 1986). Moreover, endogenous PGE2 has been shown to modulate human skin keratinocyte differentiation (Evans et al, Prostaglandins Leukot Essent Fatty Acid 49: 777-781, 1993). The observed differential expression of EP4 receptor mRNA in fetal and adult rabbit skin before and after wounding, with EP4 mRNA up-regulation in fetal skin, supports a role for PGE2 in the regulation of intracellular signal transduction via binding to EP4 receptor during fetal wound repair (Li et al, Arch Otolaryngol Head Neck Surg 126, 1337-1343, 2000). At least the preceding findings indicate that PGE2 production is essential for cutaneous wound healing.

Skin blemishes such as flesh wounds, scars and wrinkles can occur on any area of the body. Scarring may occur in all parts of the adult body, following local or systemic traumas such as mechanical injury, surgery, burn, radiation and poisoning, and represents a failure of homeostatic processes to restore normal structure at the wound sites. Wrinkles occur for a variety of reasons and are a common sign of aging. Both scars and signs of aging can typically be considered undesirable.

Accordingly, an agent that safely and effectively treats or prevents such skin blemishes is highly desirable.

SUMMARY OF THE INVENTION

The present invention is directed in part to EP4 agonists and their use in treating a variety of conditions associated with activity of the EP4 receptors. The invention provides compositions and methods for wound healing and scar reduction. The compositions and methods of the invention include at least one EP4 agonist set forth herein. Wounds and/or scars that can be treated by the compositions and methods of the invention can arise from events such as surgery, trauma, disease, mechanical injury, burn, radiation, poisoning, and the like.

Disclosed herein are compositions and methods for treating skin blemishes, healing wounds healing, and reducing scars.

In one embodiment of the invention, there are provided compounds of Formula I:

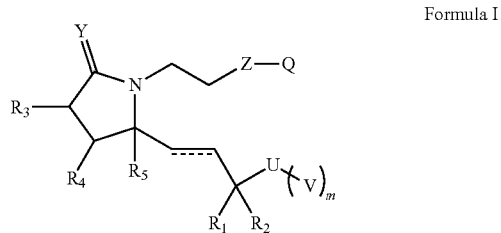

Formula I wherein:
Y is O or S:
Z is $CH_2$, O or S:
Q is aryl or heteroaryl, wherein said aryl and heteroaryl groups are optionally substituted with one or more $R^6$:
U is aryl or heteroaryl, wherein said aryl and heteroaryl groups are optionally substituted with one or more $R^7$:
V is aryl or heteroaryl; wherein said aryl and heteroaryl groups are optionally substituted with one or more $R^8$:
$R^1$ is H, $-OR^a$ or $-SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^c$, wherein $R^c$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from $-CO_2R^e$, $-CH_2OR^e$, $-CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
each $R^7$ is independently selected from H, $C_1$-$C_6$alkyl, haloalkyl, halo, hydroxyl, nitro, cyano and amino:
each $R^8$ is independently selected from H, $C_1$-$C_6$alkyl, haloalkyl, hydroxyalkyl, hydroxyl, halo, aryl and heteroaryl; and
m is 0 or 1:
wherein the dashed line represents the presence or absence of a bond; and when the dashed line is a bond, the resulting olefin geometry is cis or trans:

each aryl is $C_6$-$C_{14}$aryl; and each heteroaryl comprises 5 to 14 ring atoms:

with the provision that when Q is thiopheneyl, then m is 1;

or a pharmaceutically acceptable salt thereof.

In another embodiment of the invention, there are provided compounds of Formula I, wherein m is 0 and V is absent.

In another embodiment of the invention, there are provided compounds of Formula I, wherein m is 1.

In another embodiment of the invention, there are provided pharmaceutical compositions including at least one compound of the invention in a pharmaceutically acceptable carrier therefor.

In another embodiment of the invention, there are provided methods of treating a skin blemish, healing a wound, or reducing a scar. Such methods can be performed for example, by administering to a subject in need thereof a therapeutically effective amount of a composition of the invention.

DRAWINGS

FIG. 1 shows the structure of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used above, and throughout this disclosure, the following terms, unless otherwise indicated, shall be understood to have the following meanings.

"Patient" or "subject" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, heterocyclyl, heteroaryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)— cycloalkyl, —SF$_5$, carboxy, —C(O)O-alkyl, —C(O)NH(alkyl) and —C(O)N(alkyl)$_2$. Non-limiting examples of suitable alkyl groups include methyl, ethyl, n-propyl, isopropyl, n-butyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain: and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain: and more preferably about 2 to about 4 carbon atoms in the chain. Branched means that one or more lower alkyl groups such as methyl, ethyl or propyl, are attached to a linear alkynyl chain.

"Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thiopheneyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred halogens are fluorine, chlorine and bromine. "Halo" means —F, —Cl, —Br or —I.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —O—C(O)— alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like: such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl, morpholinoethyl and the like.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl, hydroxyethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with one or more of the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

The present invention further includes the compound of Formula I in all its isolated forms. Thus, for example, the compound of Formula I is intended to encompass all forms of the compound such as, for example, any solvates, hydrates, stereoisomers, tautomers, etc.

The present invention further includes the compound of Formula I in its purified form.

It should also be noted that any carbon as well as heteroatom with unsatisfied valences in the text, schemes, examples and Tables herein is assumed to have the sufficient number of hydrogen atom(s) to satisfy the valences, and that any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy) ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1-C_{10}$) alkyl, ($C_3-C_7$) cycloalkyl, benzyl, or R-carbonyl is a natural α-aminoacyl or natural α-aminoacyl, —$C(OH)C(O)OY_1$ wherein $Y_1$ is H, ($C_1-C_6$)alkyl or benzyl, —$C(OY_2)Y_3$ wherein $Y_2$ is ($C_1-C_4$)alkyl and $Y_3$ is ($C_1-C_6$)alkyl, carboxy ($C_1-C_6$)alkyl, amino($C_1-C_4$)alkyl or mono-N— or di-N,N—($C_1-C_6$)alkylaminoalkyl, —$C(Y_4)Y_5$ wherein $Y_4$ is H or methyl and $Y_5$ is mono-N— or di-N,N—($C_1-C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004): and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I, Ia, Ib, Ic and Id contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986)¬ 33 201-217; Anderson et al, The Practice of Medicinal Chemistry (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_1-C_4$alkyl, or $C_1-C_4$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_1-C_{20}$ alcohol or reactive derivative thereof, or by a 2,3-di ($C_6-C_{24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

In particular, a skilled person will realize that even if the absolute stereochemistry of a particular stereoisomer (e.g. an enantiomer or diastereomer) of a molecule is not known, that particular stereoisomer can be distinguished from the other stereoisomers by use of other techniques (e.g. polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography, such as flash chromatography, medium pressure chromatography, or high pressure liquid chromatography (HPLC). In particular, two or more stereoisomers such as diastereomers can be separated and characterized by their retention times, which would be expected to be replicable by using the same chromatographic conditions (e.g. flow rate, column material, solvent systems/gradient profiles, and/or others identifiable to a skilled person). In particular, a skilled person will realize that even when the exact relative retention times of one or more stereoisomers is not replicated (e.g. due to slight variations in the chromatographic parameters and/or chromatographic equipment), a stereoisomer with a shorter retention time can be said to be "faster eluting,", "earlier eluting" or having a "high Rf," and a stereoisomer with a longer retention time can be said to be "slower eluting," "later eluting or having a "low Rf." A skilled person will realize that once two or more stereoisomers are distinguished by a technique such as chromatography, the absolute stereochemistry of the stereoisomers can be determined by techniques or combinations of techniques identifiable to a skilled person (e.g. x-ray crystallography, vibrational circular dichroism, nuclear magnetic resonance, total synthesis, and others identifiable to a skilled person).

It is also possible that the compound of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

Certain isotopically-labelled compounds of Formula (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula I can be useful for medical imaging purposes. For example, those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula I, in particular those containing isotopes with longer half lives ($T_{1/2}$>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs thereof, are intended to be included in the present invention.

Disclosed herein are compositions and methods for treating skin blemishes, wound healing, and scar reduction.

The following are non-limiting embodiments of the invention.

In embodiment (1), there are provided compounds of Formula I:

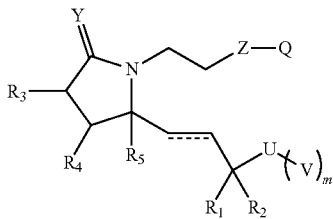

Formula I wherein:
Y is O or S:
Z is $CH_2$, O or S:
Q is aryl or heteroaryl, wherein said aryl and heteroaryl groups are optionally substituted with one or more $R^6$:
U is aryl or heteroaryl, wherein said aryl and heteroaryl groups are optionally substituted with one or more $R^7$:
V is aryl or heteroaryl; wherein said aryl and heteroaryl groups are optionally substituted with one or more $R^8$:
$R^1$ is H, $-OR^a$ or $-SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from $-CO_2R^e$, $-CH_2OR^e$, $-CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
each $R^7$ is independently selected from H, $C_1$-$C_6$alkyl, haloalkyl, halo, hydroxyl, nitro, cyano and amino:
each $R^8$ is independently selected from H, $C_1$-$C_6$alkyl, haloalkyl, hydroxyalkyl, hydroxyl, halo, aryl and heteroaryl; and
m is 0 or 1:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
with the provision that when Q is thiopheneyl, then m is 1:
or a pharmaceutically acceptable salt thereof.

In embodiment (2), there are provided compounds of embodiment (1) wherein:
Y is O:
Z is $CH_2$:
$R^1$ is $-OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (3), there are provided compounds of embodiment (2) wherein:
Q is aryl, wherein said aryl is optionally substituted with one $R^6$; and
$R^6$ is $-CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (4), there are provided compounds of embodiment (3), wherein:
Q is:

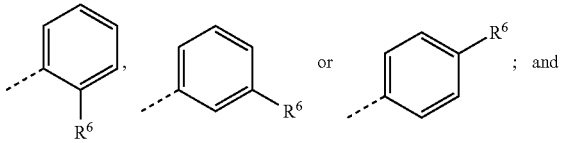

$R^6$ is $-CO_2R^e$, wherein $R^e$ is selected from H, $C_1$-$C_6$alkyl, haloalkyl, hydroxyalkyl and aryl:
or a pharmaceutically acceptable salt thereof.

In embodiment (5), there are provided compounds of embodiment (1) wherein:
Q is heteroaryl, wherein said heteroaryl is optionally substituted with one $R^6$; and
$R^6$ is $-CO_2R^e$, wherein $R^e$ is independently selected from H, $C_1$-$C_6$alkyl, haloalkyl, hydroxyalkyl and aryl:
with the provision that when Q is thiopheneyl, then m is 1:
or a pharmaceutically acceptable salt thereof.

In embodiment (6), there are provided compounds of embodiment (5) wherein:
Y is O:
Z is $CH_2$:
Q is furanyl, thiopheneyl or thiazolyl, wherein each furanyl, thiopheneyl and thiazolyl group is substituted with one $R^6$:
$R^1$ is $-OR^a$, wherein $R^a$ is H:
$R^2$ is H:
each of $R^3$, $R^4$ and $R^5$ is H:
$R^6$ is $-CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
with the provision that when Q is thiopheneyl, then m is 1:
or a pharmaceutically acceptable salt thereof.

In some embodiments there are provided compounds of Formula I, wherein m is 0 and V is absent.

In one such embodiment, which is embodiment (7), there are provided compounds of embodiment (1) having the structure of Formula Ia:

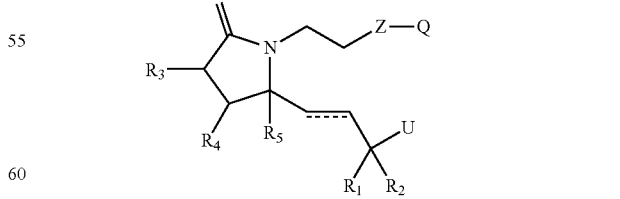

Formula Ia wherein:
Y is O or S:
Z is $CH_2$, O or S:
Q is aryl or heteroaryl, wherein said aryl and heteroaryl groups are optionally substituted with one or more $R^6$:

U is aryl or heteroaryl, wherein said aryl and heteroaryl groups are optionally substituted with one or more $R^7$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (8), there are provided compounds of embodiment (7) wherein:
Y is O:
Z is $CH_2$:
$R^1$ is —$OR^a$, wherein $R^a$ is H:
$R^2$ is H:
each of $R^3$, $R^4$, and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (9), there are provided compounds of embodiment (8) wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (10), there are provided compounds of embodiment (9) wherein:
Q is:

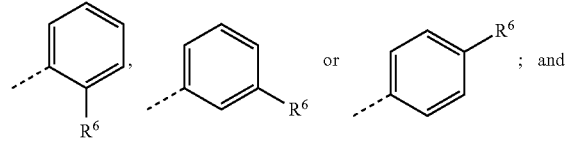

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (11), there are provided compounds of embodiment (7), wherein:
Q is heteroaryl, wherein said heteroaryl is substituted with one $R^6$; and
$R^6$ is —$CO_2R^e$, wherein $R^e$ is independently selected from H, $C_1$-$C_6$alkyl, haloalkyl, hydroxyalkyl and aryl:
or a pharmaceutically acceptable salt thereof.

In embodiment (12), there are provided compounds of embodiment (11), wherein:

Y is O:
Z is $CH_2$:
Q is furanyl or thiazolyl, wherein each furanyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ia, wherein U is an optionally substituted aryl.

In one such embodiment, which is embodiment (13), there are provided compounds of embodiment (7) wherein:
Y is O or S:
Z is $CH_2$, O or S:
Q is aryl or heteroaryl, wherein said aryl and heteroaryl groups are optionally substituted with one or more $R^6$:
U is aryl, wherein said aryl group is optionally substituted with one or more $R^7$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$, and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (14), there are provided compounds of embodiment (13) wherein:
Y is O:
Z is $CH_2$:
$R^1$ is —$OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (15), there are provided compounds of embodiment (14), wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (16), there are provided compounds of embodiment (15) wherein:

Q is:

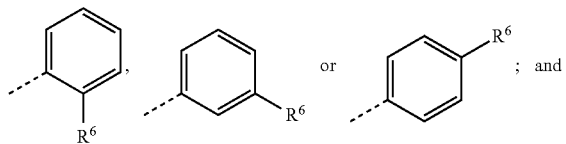

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (17), there are provided compounds of embodiment (13), wherein:
Q is heteroaryl, wherein said heteroaryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (18), there are provided compounds of embodiment (17), wherein:
Y is O:
Z is $CH_2$:
Q is furanyl or thiazolyl, wherein each furanyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ia, wherein U is an optionally substituted phenyl.
In one such embodiment, which is embodiment (19), there are provided compounds of embodiment (7) wherein:
Y is O or S:
Z is $CH_2$, O or S:
Q is aryl or heteroaryl, wherein said aryl and heteroaryl groups are optionally substituted with one or more $R^6$:
U is:

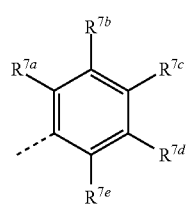

wherein:
$R^{7a}$ is H, $C_1$-$C_6$alkyl, haloalkyl, halo, hydroxyl, nitro, cyano or amino:
$R^{7b}$ is H, $C_1$-$C_6$alkyl, haloalkyl, halo, hydroxyl, nitro, cyano or amino:
$R^{7c}$ is H, $C_1$-$C_6$alkyl, haloalkyl, halo, hydroxyl, nitro, cyano or amino:
$R^{7d}$ is H, $C_1$-$C_6$alkyl, haloalkyl, halo, hydroxyl, nitro, cyano or amino:
$R^{7e}$ is H, $C_1$-$C_6$alkyl, haloalkyl, halo, hydroxyl, nitro, cyano or amino:

$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl; and
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (20), there are provided compounds of embodiment (19) wherein:
Y is O:
Z is $CH_2$:
$R^1$ is —$OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (21), there are provided compounds of embodiment (20), wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (22), there are provided compounds of embodiment (21) wherein:
Q is:

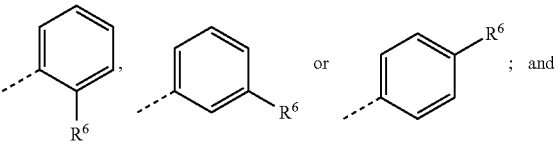

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (23), there are provided compounds of embodiment (19), wherein:
Q is heteroaryl, wherein said heteroaryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (24), there are provided compounds of embodiment (23), wherein:
Y is O:
Z is $CH_2$:
Q is furanyl or thiazolyl, wherein each furanyl or thiazolyl group is substituted with one $R^6$:

$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ia, wherein U is an optionally substituted heteroaryl.

In one such embodiment, which is embodiment (25), there are provided compounds of embodiment (7), wherein:
Y is O or S:
Z is $CH_2$, O or S:
Q is aryl or heteroaryl, wherein said aryl and heteroaryl groups are optionally substituted with one or more $R^6$:
U is heteroaryl, wherein said heteroaryl group is optionally substituted with one or more $R^7$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$, and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (26), there are provided compounds of embodiment (25), wherein:
Y is O:
Z is $CH_2$:
$R^1$ is —$OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (27), there are provided compounds of embodiment (26) wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (28), there are provided compounds of embodiment (27) wherein:

Q is:

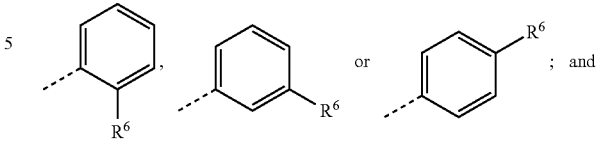

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (29), there are provided compounds of embodiment (25) wherein:
Q is heteroaryl, wherein said heteroaryl is substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (30), there are provided compounds of embodiment (29) wherein:
Y is O:
Z is $CH_2$:
Q is furanyl or thiazolyl, wherein each furanyl or thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ia, wherein U is an optionally substituted thiopheneyl or furanyl.

In embodiment (31), there are provided compounds of embodiment (7) wherein:
Y is O or S:
Z is $CH_2$, O or S:
Q is aryl or heteroaryl, wherein said aryl and heteroaryl groups are optionally substituted with one or more $R^6$:
U is thiopheneyl or furanyl, wherein said thiopheneyl and furanyl groups are optionally substituted with one or more $R^7$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$, and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (32), there are provided compounds of embodiment (31), wherein:
Y is O:
Z is $CH_2$:
U is thiopheneyl or furanyl, wherein said thiophenyl and furanyl groups are optionally substituted with one or more $R^7$:
$R^1$ is —$OR^a$, wherein $R^a$ is H:
$R^2$ is H:
each $R^3$, $R^4$, and $R^5$ is H:
each $R^7$ is independently selected from H, $C_1$-$C_6$alkyl, haloalkyl, halo, hydroxyl, nitro, cyano and amino:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (33), there are provided compounds of embodiment (32), wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (34), there are provided compounds of embodiment (33), wherein:
Q is:

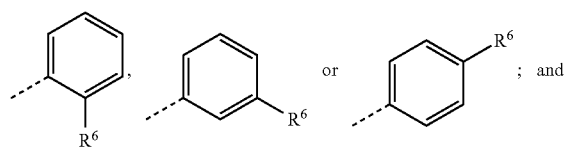

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (35), there are provided compounds of embodiment (31), wherein:
Q is heteroaryl, wherein said heteroaryl is substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (36), there are provided compounds of embodiment (35), wherein:
Y is O:
Z is $CH_2$:
Q is furanyl or thiazolyl, wherein each furanyl or thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments there are provided compounds of Formula I, wherein m is 1.

In one such embodiment, which is embodiment (37), there are provided compounds of embodiment (1) having the structure of Formula Ib:

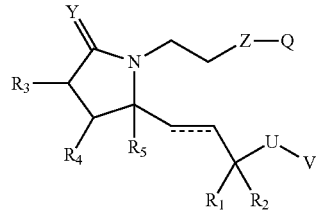

Formula Ib wherein:
Y is O or S:
Z is $CH_2$, O or S:
Q is aryl or heteroaryl, wherein said aryl and heteroaryl groups are optionally substituted with one or more $R^6$:
U is aryl or heteroaryl, wherein said aryl and heteroaryl groups are optionally substituted with one or more $R^7$:
V is aryl or heteroaryl; wherein said aryl and heteroaryl groups are optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each of $R^3$, $R^4$ and $R^5$ is independently selected from H, $C_1$-$C_6$alkyl, $CF_3$, halo, or $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
each $R^7$ is independently selected from H, $C_1$-$C_6$alkyl, haloalkyl, halo, hydroxyl, nitro, cyano and amino; and
each $R^8$ is independently selected from H, $C_1$-$C_6$alkyl, haloalkyl, hydroxyalkyl, hydroxyl, halo, aryl and heteroaryl:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (38), there are provided compounds of embodiment (37) wherein:
Y is O:
Z is $CH_2$:
$R^1$ is —$OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (39), there are provided compounds of embodiment (38), wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (40), there are provided compounds of embodiment (39) wherein:

Q is:

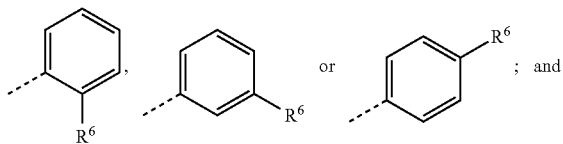

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (41), there are provided compounds of embodiment (37), wherein:
Q is heteroaryl, wherein said heteroaryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (42), there are provided compounds of embodiment (41), wherein:
Y is O:
Z is $CH_2$:
Q is furanyl, thiopheneyl or thiazolyl, wherein each furanyl, thiopheneyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ib wherein U is optionally substituted aryl.

In one such embodiment, which is embodiment (43), there are provided compounds of embodiment (37) wherein:
Y is O or S:
Z is $CH_2$, O or S:
Q is aryl or heteroaryl, wherein said aryl and heteroaryl groups are optionally substituted with one or more $R^6$:
U is aryl, wherein said aryl group is optionally substituted with one or more $R^7$:
V is aryl or heteroaryl; wherein said aryl and heteroaryl groups are optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
each $R^7$ is independently selected from H, $C_1$-$C_6$alkyl, haloalkyl, halo, hydroxyl, nitro, cyano and amino; and
each $R^8$ is independently selected from H, $C_1$-$C_6$alkyl, haloalkyl, hydroxyalkyl, hydroxyl, halo, aryl and heteroaryl:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (44), there are provided compounds of embodiment (43) wherein:
Y is O:
Z is $CH_2$:
$R^1$ is —$OR^a$, wherein $R^a$ is H:
$R^2$ is H:
each of $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (45), there are provided compounds of embodiment (44) wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (46), there are provided compounds of embodiment (45), wherein:
Q is:

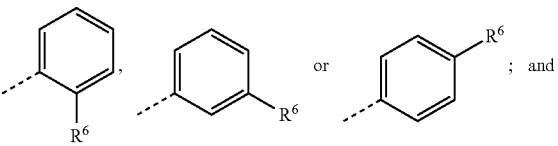

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (47), there are provided compounds of embodiment (43) wherein:
Q is heteroaryl, wherein said heteroaryl is substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (48), there are provided compounds of embodiment (47), wherein:
Y is O:
Z is $CH_2$:
Q is furanyl, thiopheneyl or thiazolyl, wherein each furanyl, thiopheneyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ib, wherein U is an optionally substituted phenyl.

In one such embodiment, which is embodiment (49), there are provided compounds of embodiment (37) wherein:
Y is O or S:
Z is CH$_2$, O or S:
Q is aryl or heteroaryl, wherein said aryl and heteroaryl groups are optionally substituted with one or more R$^6$:
U is:

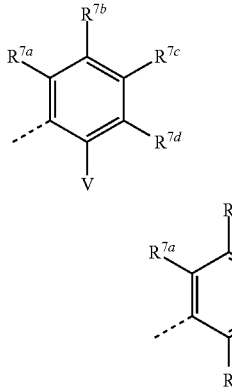
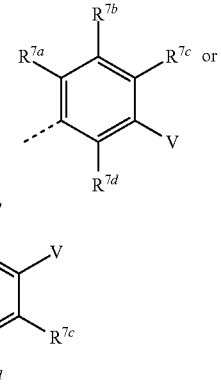
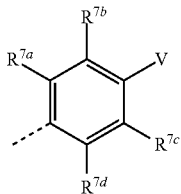

wherein:
R$^{7a}$ is H, C$_1$-C$_6$alkyl, haloalkyl, halo, hydroxyl, nitro, cyano or amino:
R$^{7b}$ is H, C$_1$-C$_6$alkyl, haloalkyl, halo, hydroxyl, nitro, cyano or amino:
R$^{7c}$ is H, C$_1$-C$_6$alkyl, haloalkyl, halo, hydroxyl, nitro, cyano or amino:
R$^{7d}$ is H, C$_1$-C$_6$alkyl, haloalkyl, halo, hydroxyl, nitro, cyano or amino:
V is aryl or heteroaryl; wherein said aryl and heteroaryl groups are optionally substituted with one or more R$^8$:
R$^1$ is H, —OR$^a$ or —SR$^a$, wherein R$^a$ is H or C$_1$-C$_6$alkyl:
R$^2$ is H, halo or C$_1$-C$_6$alkyl:
each of R$^3$, R$^4$ and R$^5$ is independently selected from H, C$_1$-C$_6$alkyl, CF$_3$, halo, or OR$^e$, wherein R$^e$ is H, C$_1$-C$_6$alkyl, C(O)R$^d$ or SO$_2$R$^d$, wherein R$^d$ is C$_1$-C$_6$ alkyl, CF$_3$, aryl or heteroaryl:
each R$^6$ is independently selected from —CO$_2$R$^e$, —CH$_2$OR$^e$, —CONR$^e$R$^f$ and tetrazol-5-yl; wherein each R$^e$ is independently selected from H, C$_1$-C$_6$alkyl, haloalkyl, hydroxyalkyl and aryl, and each R$^f$ is independently selected from H, C$_1$-C$_6$alkyl, C(O)R$^g$ and SO$_2$R$^g$, wherein R$^g$ is C$_1$-C$_6$ alkyl, CF$_3$, aryl or heteroaryl; and
each R$^8$ is independently selected from H, C$_1$-C$_6$alkyl, haloalkyl, hydroxyalkyl, hydroxyl, halo, aryl and heteroaryl:
wherein the dashed line represents the presence or absence of a bond; and when the dashed line is a bond, the resulting olefin geometry is cis or trans:
each aryl is C$_6$-C$_{14}$aryl; and
each heteroaryl comprises 5 to 14 ring atoms:
or a pharmaceutically acceptable salt thereof.

In embodiment (50), there are provided compounds of embodiment (49) wherein:
Y is O:
Z is CH$_2$:
R$^1$ is —OR$^a$, wherein R$^a$ is H:
R$^2$ is H:
each R$^3$, R$^4$ and R$^5$ is H:
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In embodiment (51), there are provided compounds of embodiment (50) wherein:
Q is aryl, wherein said aryl is optionally substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (52), there are provided compounds of embodiment (51) wherein
Q is:

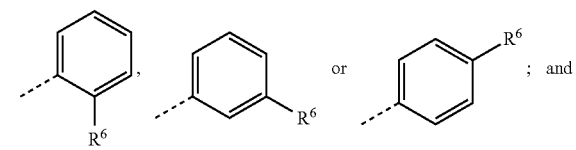

R$^6$ is —CO$_2$R$^e$, wherein R$^e$ is selected from H, C$_1$-C$_6$alkyl, haloalkyl, hydroxyalkyl and aryl:
or a pharmaceutically acceptable salt thereof.

In embodiment (53), there are provided compounds of embodiment (49) wherein:
Q is heteroaryl, wherein said heteroaryl is substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (54), there are provided compounds of embodiment (53), wherein:
Y is O:
Z is CH$_2$:
Q is furanyl, thiopheneyl or thiazolyl, wherein each furanyl, thiopheneyl and thiazolyl group is substituted with one R$^6$:
R$^1$ is —OR$^a$, wherein R$^a$ is H:
R$^2$ is H:
each of R$^3$, R$^4$ and R$^5$ is H:
R$^6$ is —CO$_2$R$^e$, wherein R$^e$ is selected from H, C$_1$-C$_6$alkyl, haloalkyl, hydroxyalkyl and aryl; and
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In some embodiments, there are provided compounds of Formula Ib, wherein U is optionally substituted heteroaryl.
In one such embodiment, which is embodiment (55), there are provided compounds of embodiment (37) wherein:
Y is O or S:
Z is CH$_2$, O or S:
Q is aryl or heteroaryl, wherein said aryl and heteroaryl groups are optionally substituted with one or more R$^6$:
U is heteroaryl, wherein said heteroaryl group is optionally substituted with one or more R$^7$:
V is aryl or heteroaryl; wherein said aryl and heteroaryl groups are optionally substituted with one or more R$^8$:
R$^1$ is H, —OR$^a$ or —SR$^a$, wherein R$^a$ is H or C$_1$-C$_6$alkyl:
R$^2$ is H, halo or C$_1$-C$_6$alkyl:
each R$^3$, R$^4$ and R$^5$ is independently selected from H, C$_1$-C$_6$alkyl, CF$_3$, halo and OR$^e$, wherein R$^e$ is H, $C_1$-$C_6$alkyl, $C(O)R^d$ or $SO_2R^d$, wherein $R^d$ is $C_1$-$C_6$ alkyl, $CF_3$, aryl or heteroaryl:

each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:

each $R^7$ is independently selected from H, $C_1$-$C_6$alkyl, haloalkyl, halo, hydroxyl, nitro, cyano and amino; and each $R^8$ is independently selected from H, $C_1$-$C_6$alkyl, haloalkyl, hydroxyalkyl, hydroxyl, halo, aryl and heteroaryl:

wherein the dashed line represents the presence or absence of a bond; and when the dashed line is a bond, the resulting olefin geometry is cis or trans:

each aryl is $C_6$-$C_{14}$aryl; and each heteroaryl comprises 5 to 14 ring atoms:

or a pharmaceutically acceptable salt thereof.

In embodiment (56), there are provided compounds of embodiment (55) wherein:

Y is O:
Z is $CH_2$:
$R^1$ is —$OR^a$, wherein $R^a$ is H:
$R^2$ is H:
each $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (57), there are provided compounds of embodiment (56), wherein:

Q is aryl, wherein said aryl is optionally substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (58), there are provided compounds of embodiment (57), wherein:

Q is:

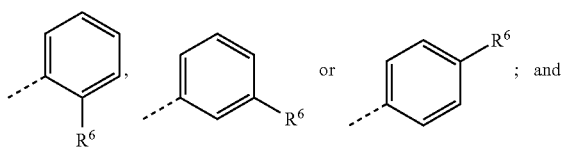

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (59), there are provided compounds of embodiment (55), wherein:

Q is heteroaryl, wherein said heteroaryl is substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (60), there are provided compounds of any one of embodiments (59) through (59) wherein:

Y is O:
Z is $CH_2$:
Q is furanyl, thiopheneyl or thiazolyl, wherein each furanyl, thiopheneyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ib. wherein U is optionally substituted thiopheneyl or furanyl.

In one such embodiment, which is embodiment (61), there are provided compounds of embodiment (37) wherein:

Y is O or S:
Z is $CH_2$, O or S:
Q is aryl or heteroaryl, wherein said aryl and heteroaryl groups are optionally substituted with one or more $R^6$:
U is thiopheneyl or furanyl, wherein said thiophenyl and furanyl groups are optionally substituted with one or more $R^7$:
V is aryl or heteroaryl; wherein said aryl and heteroaryl groups are optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (62), there are provided compounds of embodiment (61), wherein:

Y is O:
Z is $CH_2$:
$R^1$ is —$OR^a$, wherein $R^a$ is H:
$R^2$ is H:
each $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (63), there are provided compounds of embodiment (62) wherein:

Q is aryl, wherein said aryl group is optionally substituted with one $R^6$; and $R^6$ is —$CO_2R^e$, wherein $R^e$ is independently selected from H, $C_1$-$C_6$alkyl, haloalkyl, hydroxyalkyl and aryl:
or a pharmaceutically acceptable salt thereof.

In embodiment (64), there are provided compounds of embodiment (63) wherein:

Q is:

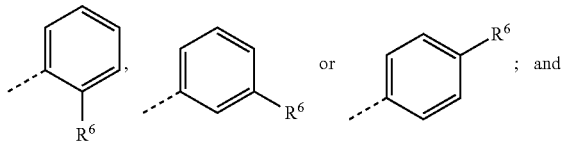

$R^6$ is —$CO_2R^e$, wherein $R^e$ is selected from H, $C_1$-$C_6$alkyl, haloalkyl, hydroxyalkyl and aryl:

or a pharmaceutically acceptable salt thereof.

In embodiment (65), there are provided compounds of embodiment (61) wherein:

Q is heteroaryl, wherein said heteroaryl is optionally substituted with one $R^6$; and $R^6$ is —$CO_2R^e$, wherein $R^e$ is independently selected from H, $C_1$-$C_6$alkyl, haloalkyl, hydroxyalkyl and aryl:

or a pharmaceutically acceptable salt thereof.

In embodiment (66), there are provided compounds of embodiment (65), wherein:

Y is O:

Z is $CH_2$:

Q is furanyl, thiopheneyl or thiazolyl, wherein each furanyl, thiopheneyl and thiazolyl group is substituted with one $R^6$:

$R^1$ is —$OR^a$, wherein $R^a$ is H:

$R^2$ is H:

each of $R^3$, $R^4$ and $R^5$ is H:

$R^6$ is —$CO_2R^e$, wherein $R^e$ is selected from H, $C_1$-$C_6$alkyl, haloalkyl, hydroxyalkyl and aryl:

the dashed line represents the presence of a bond, wherein the resulting olefin geometry is trans:

each aryl is $C_6$aryl; and each heteroaryl comprises 5 or 6 ring atoms:

or a pharmaceutically acceptable salt thereof.

In some embodiments, there are provided compounds of Formula Ib, wherein U and V are each an optionally substituted aryl.

In one such embodiment, which is embodiment (67), there are provided compounds of embodiment (37) wherein:

Y is O or S:

Z is $CH_2$, O or S:

Q is aryl or heteroaryl, wherein said aryl and heteroaryl groups are optionally substituted with one or more $R^6$:

U is aryl, wherein said aryl group is optionally substituted with one or more $R^7$:

V is aryl; wherein said aryl group is optionally substituted with one or more $R^8$:

$R^1$ is H, —$OR^a$ or —$SR^a$, wherein $R^a$ is H or $C_1$-$C_6$alkyl:

$R^2$ is H, halo or $C_1$-$C_6$alkyl:

each $R^3$, $R^4$ and $R^5$ is independently selected from H, $C_1$-$C_6$alkyl, $CF_3$, halo or $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:

each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:

each $R^7$ is independently selected from H, $C_1$-$C_6$alkyl, haloalkyl, halo, hydroxyl, nitro, cyano and amino; and each $R^8$ is independently selected from H, $C_1$-$C_6$alkyl, haloalkyl, hydroxyalkyl, hydroxyl, halo, aryl and heteroaryl:

wherein the dashed line represents the presence or absence of a bond; and when the dashed line is a bond, the resulting olefin geometry is cis or trans:

each aryl is $C_6$-$C_{14}$aryl; and each heteroaryl comprises 5 to 14 ring atoms:

or a pharmaceutically acceptable salt thereof.

In embodiment (68), there are provided compounds of embodiment (67), wherein:

Y is O:

Z is $CH_2$:

$R^1$ is —$OR^a$, wherein $R^a$ is H:

$R^2$ is H:

each $R^3$, $R^4$ and $R^5$ is H:

the dashed line represents the presence of a bond, wherein the resulting olefin geometry is trans:

each aryl is $C_6$aryl; and each heteroaryl comprises 5 or 6 ring atoms:

or a pharmaceutically acceptable salt thereof.

In embodiment (69), there are provided compounds of embodiment (68) wherein:

Q is aryl, wherein said aryl is optionally substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (70), there are provided compounds of embodiment (69) wherein:

Q is:

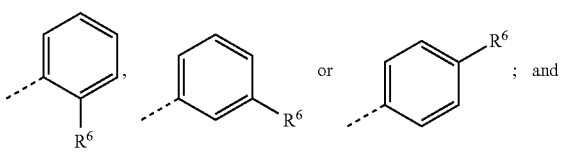

$R^6$ is —$CO_2R^e$, wherein $R^e$ is selected from H, $C_1$-$C_6$alkyl, haloalkyl, hydroxyalkyl and aryl:

or a pharmaceutically acceptable salt thereof.

In embodiment (71), there are provided compounds of embodiment (67) wherein:

Q is heteroaryl, wherein said heteroaryl is optionally substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (72), there are provided compounds of embodiment (71), wherein:

Y is O:

Z is $CH_2$:

Q is furanyl, thiopheneyl or thiazolyl, wherein each furanyl, thiopheneyl and thiazolyl group is substituted with one $R^6$:

$R^1$ is —$OR^a$, wherein $R^a$ is H:

$R^2$ is H:

each of $R^3$, $R^4$ and $R^5$ is H:

$R^6$ is —$CO_2R^e$, wherein $R^e$ is selected from H, $C_1$-$C_6$alkyl, haloalkyl, hydroxyalkyl and aryl:

the dashed line represents the presence of a bond, wherein the resulting olefin geometry is trans:

each aryl is $C_6$aryl; and each heteroaryl comprises 5 or 6 ring atoms:

or a pharmaceutically acceptable salt thereof.

In some embodiments, there are provided compounds of Formula Ib, wherein U is an optionally substituted phenyl, and V is an optionally substituted aryl.

In one such embodiment, which is embodiment (73), there are provided compounds of embodiment (37) wherein:
Y is O or S:
Z is $CH_2$, O or S:
Q is aryl or heteroaryl, wherein said aryl and heteroaryl groups are optionally substituted with one or more $R^6$:
U is:

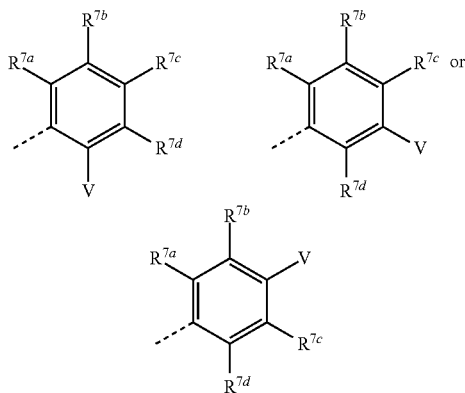

wherein:
$R^{7a}$ is H, $C_1$-$C_6$alkyl, haloalkyl, halo, hydroxyl, nitro, cyano or amino:
$R^{7b}$ is H, $C_1$-$C_6$alkyl, haloalkyl, halo, hydroxyl, nitro, cyano or amino:
$R^{7c}$ is H, $C_1$-$C_6$alkyl, haloalkyl, halo, hydroxyl, nitro, cyano or amino:
$R^{7d}$ is H, $C_1$-$C_6$alkyl, haloalkyl, halo, hydroxyl, nitro, cyano or amino:
V is aryl, wherein said aryl group is optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^8$ is independently selected from H, $C_1$-$C_6$alkyl, haloalkyl, hydroxyalkyl, hydroxyl, halo, aryl and heteroaryl:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (74), there are provided compounds of embodiment (73) wherein:
Y is O:
Z is $CH_2$:
$R^1$ is —$OR^a$, wherein $R^a$ is H:
$R^2$ is H:
each $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (75), there are provided compounds of embodiment (74) wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (76), there are provided compounds of embodiment (75), wherein:
Q is:

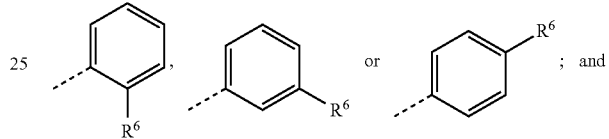

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (77), there are provided compounds of embodiment (73) wherein:
Q is heteroaryl, wherein said heteroaryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (78), there are provided compounds of embodiment (77) wherein:
Y is O:
Z is $CH_2$:
Q is furanyl, thiopheneyl or thiazolyl, wherein each furanyl, thiopheneyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ib, wherein U is an optionally substituted heteroaryl, and V is an optionally substituted aryl.

In one such embodiment, which is embodiment (79), there are provided compounds of embodiment (37) wherein:
Y is O or S:
Z is $CH_2$, O or S:
Q is aryl or heteroaryl, wherein said aryl and heteroaryl groups are optionally substituted with one or more $R^6$:
U is heteroaryl, wherein said heteroaryl group is optionally substituted with one or more $R^7$:

V is aryl, wherein said aryl group is optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$, and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl:
each $R^7$ is independently selected from H, $C_1$-$C_6$alkyl, haloalkyl, halo, hydroxyl, nitro, cyano and amino; and
each $R^8$ is independently selected from H, $C_1$-$C_6$alkyl, haloalkyl, hydroxyalkyl, hydroxyl, halo, aryl and heteroaryl:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (80), there are provided compounds of embodiment (79), wherein:
Y is O:
Z is $CH_2$:
$R^1$ is —$OR^a$, wherein $R^a$ is H:
$R^2$ is H:
each $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (81), there are provided compounds of embodiment (80) wherein:
Q is aryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (82), there are provided compounds of embodiment (81) wherein:
Q is:

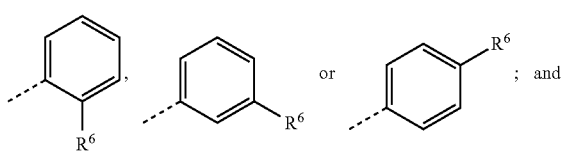

$R^6$ is —$CO_2R^e$, wherein $R^e$ is selected from H, $C_1$-$C_6$alkyl, haloalkyl, hydroxyalkyl and aryl:
or a pharmaceutically acceptable salt thereof.

In embodiment (83), there are provided compounds of embodiment (79) wherein:
Q is heteroaryl, wherein said aryl is optionally substituted with one $R^6$; and
$R^6$ is —$CO_2R^e$, wherein $R^e$ is independently selected from H, $C_1$-$C_6$alkyl, haloalkyl, hydroxyalkyl and aryl; and
or a pharmaceutically acceptable salt thereof.

In embodiment (84), there are provided compounds of embodiment (83), wherein:
Y is O:
Z is $CH_2$:
Q is furanyl, thiopheneyl or thiazolyl, wherein each furanyl, thiopheneyl and thiazolyl group is substituted with one $R^6$:
$R^1$ is —$OR^a$, wherein $R^a$ is H:
$R^2$ is H:
each of $R^3$, $R^4$ and $R^5$ is H:
$R^6$ is —$CO_2R^e$, wherein $R^e$ is selected from H, $C_1$-$C_6$alkyl, haloalkyl, hydroxyalkyl and aryl:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In some embodiments, there are provided compounds of Formula Ib, wherein U is an optionally substituted thiopheneyl or furanyl, and V is optionally substituted aryl.

In embodiment (85), there are provided compounds of embodiment (37) wherein:
Y is O or S:
Z is $CH_2$, O or S:
Q is aryl or heteroaryl, wherein said aryl and heteroaryl groups are optionally substituted with one or more $R^6$:
U is thiopheneyl or furanyl, wherein said thiophenyl and furanyl groups are optionally substituted with one or more $R^7$:
V is aryl, wherein said aryl group is optionally substituted with one or more $R^8$:
$R^1$ is H, —$OR^a$ or —$SR^a$, wherein $R^a$ is H or $C_1$-$C_6$alkyl:
$R^2$ is H, halo or $C_1$-$C_6$alkyl:
each $R^3$, $R^4$, and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:
each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and
each $R^7$ is independently selected from H, $C_1$-$C_6$alkyl, haloalkyl, halo, hydroxyl, nitro, cyano and amino:
wherein the dashed line represents the presence or absence of a bond; and when the dashed line is a bond, the resulting olefin geometry is cis or trans:
each aryl is $C_6$-$C_{14}$aryl; and
each heteroaryl comprises 5 to 14 ring atoms:
or a pharmaceutically acceptable salt thereof.

In embodiment (86), there are provided compounds of embodiment (85), wherein:
Y is O:
Z is $CH_2$:
$R^1$ is —$OR^a$, wherein $R^a$ is H:
$R^2$ is H:
each $R^3$, $R^4$ and $R^5$ is H:
the dashed line represents the presence of a bond, wherein the resulting olefin geometry is trans:
each aryl is $C_6$aryl; and
each heteroaryl comprises 5 or 6 ring atoms:
or a pharmaceutically acceptable salt thereof.

In embodiment (87), there are provided compounds of embodiment (86) wherein:

Q is aryl, wherein said aryl is optionally substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (88), there are provided compounds of embodiment (87) wherein:

Q is:

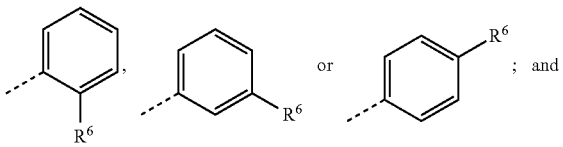

$R^6$ is —$CO_2R^e$, wherein $R^e$ is selected from H, $C_1$-$C_6$alkyl, haloalkyl, hydroxyalkyl and aryl:

or a pharmaceutically acceptable salt thereof.

In embodiment (89), there are provided compounds of embodiment (85) wherein:

Q is heteroaryl, wherein said heteroaryl is optionally substituted with one $R^6$; and $R^6$ is —$CO_2R^e$, wherein $R^e$ is independently selected from H, $C_1$-$C_6$alkyl, haloalkyl, hydroxyalkyl and aryl; and or a pharmaceutically acceptable salt thereof.

In embodiment (90), there are provided compounds of embodiment (85), wherein:

Y is O:

Z is $CH_2$:

Q is furanyl, thiopheneyl or thiazolyl, wherein each furanyl, thiopheneyl and thiazolyl group is substituted with one $R^6$:

$R^1$ is —$OR^a$, wherein $R^a$ is H:

$R^2$ is H:

each of $R^3$, $R^4$ and $R^5$ is H:

$R^6$ is —$CO_2R^e$, wherein $R^e$ is selected from H, $C_1$-$C_6$alkyl, haloalkyl, hydroxyalkyl and aryl:

the dashed line represents the presence of a bond, wherein the resulting olefin geometry is trans:

each aryl is $C_6$aryl; and each heteroaryl comprises 5 or 6 ring atoms:

or a pharmaceutically acceptable salt thereof.

In embodiment (91), there are provided compounds of embodiment (37) wherein:

Y is O or S:

Z is $CH_2$, O or S:

Q is aryl or heteroaryl, wherein said aryl and heteroaryl groups are optionally substituted with one or more $R^6$:

U is:

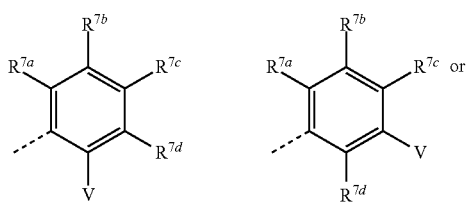

-continued

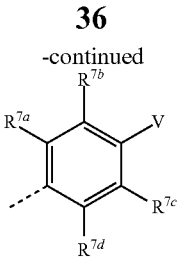

wherein:

$R^{7a}$ is H, $C_1$-$C_6$alkyl, haloalkyl, halo, hydroxyl, nitro, cyano or amino:

$R^{7b}$ is H, $C_1$-$C_6$alkyl, haloalkyl, halo, hydroxyl, nitro, cyano or amino:

$R^{7c}$ is H, $C_1$-$C_6$alkyl, haloalkyl, halo, hydroxyl, nitro, cyano or amino:

$R^{7d}$ is H, $C_1$-$C_6$alkyl, haloalkyl, halo, hydroxyl, nitro, cyano or amino:

V is

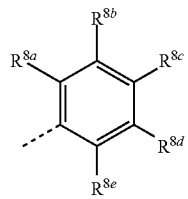

wherein:

$R^{8a}$ is H, $C_1$-$C_6$alkyl, haloalkyl, halo, hydroxyl, hydroxyalkyl, aryl or heteroaryl:

$R^{8b}$ is H, $C_1$-$C_6$alkyl, haloalkyl, halo, hydroxyl, hydroxyalkyl, aryl or heteroaryl:

$R^{8c}$ is H, $C_1$-$C_6$alkyl, haloalkyl, halo, hydroxyl, hydroxyalkyl, aryl or heteroaryl:

$R^{8d}$ is H, $C_1$-$C_6$alkyl, haloalkyl, halo, hydroxyl, hydroxyalkyl, aryl or heteroaryl:

$R^{8e}$ is H, $C_1$-$C_6$alkyl, haloalkyl, halo, hydroxyl, hydroxyalkyl, aryl or heteroaryl:

$R^1$ is H, —$OR^a$ or —$SR^a$, wherein $R^a$ is H or $C_1$-$C_6$alkyl:

$R^2$ is H, halo or $C_1$-$C_6$alkyl:

each $R^3$, $R^4$ and $R^5$ is independently selected from H, $C_1$-$C_6$alkyl, $CF_3$, halo and $OR^e$, wherein $R^e$ is H, $C_1$-$C_6$alkyl, $C(O)R^d$ or $SO_2R^d$, wherein $R^d$ is $C_1$-$C_6$ alkyl, $CF_3$, aryl or heteroaryl:

each $R^6$ is independently selected from —$CO_2R^e$, —$CH_2OR^e$, —$CONR^eR^f$ and tetrazol-5-yl; wherein each $R^e$ is independently selected from H, $C_1$-$C_6$alkyl, haloalkyl, hydroxyalkyl and aryl, and each $R^f$ is independently selected from H, $C_1$-$C_6$alkyl, $C(O)R^g$ and $SO_2R^g$, wherein $R^g$ is $C_1$-$C_6$ alkyl, $CF_3$, aryl or heteroaryl; and each $R^8$ is independently selected from H, $C_1$-$C_6$alkyl, haloalkyl, hydroxyalkyl, hydroxyl, halo, aryl and heteroaryl:

wherein the dashed line represents the presence or absence of a bond; and when the dashed line is a bond, the resulting olefin geometry is cis or trans:

each aryl is $C_6$-$C_{14}$aryl; and each heteroaryl comprises 5 to 14 ring atoms:

or a pharmaceutically acceptable salt thereof.

In embodiment (92), there are provided compounds of embodiment (91) wherein:

Y is O:
Z is CH$_2$:
R$^1$ is —OR$^a$, wherein R$^a$ is H:
R$^2$ is H:
each R$^3$, R$^4$ and R$^5$ is H:
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In embodiment (93), there are provided compounds of embodiment (92) wherein:
Q is aryl, wherein said aryl is optionally substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (94), there are provided compounds of embodiment (93), wherein:
Q is:

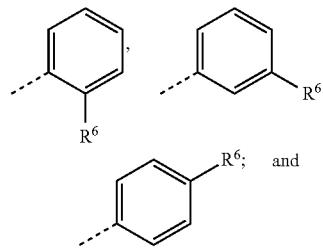

R$^6$ is —CO$_2$R$^e$, wherein R$^e$ is selected from H, C$_1$-C$_6$alkyl, haloalkyl, hydroxyalkyl and aryl:
or a pharmaceutically acceptable salt thereof.

In embodiment (95), there are provided compounds of embodiment (91) wherein:
Q is heteroaryl, wherein said heteroaryl is optionally substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (96), there are provided compounds of embodiment (95) wherein:
Y is O:
Z is CH$_2$:
Q is furanyl, thiopheneyl or thiazolyl, wherein each furanyl, thiopheneyl and thiazolyl group is substituted with one R$^6$:
R$^1$ is —OR$^a$, wherein R$^a$ is H:
R$^2$ is H:
each of R$^3$, R$^4$ and R$^5$ is H:
R$^6$ is —CO$_2$R$^e$, wherein R$^e$ is selected from H, C$_1$-C$_6$alkyl, haloalkyl, hydroxyalkyl and aryl:
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In one such embodiment, which is embodiment (97), there are provided compounds of embodiment (37) wherein:
Y is O or S:
Z is CH$_2$, O or S:
Q is aryl or heteroaryl, wherein said aryl and heteroaryl groups are optionally substituted with one or more R$^6$:

U is:

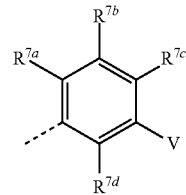

wherein:
R$^{7a}$ is H, C$_1$-C$_6$alkyl, haloalkyl, halo, hydroxyl, nitro, cyano or amino:
R$^{7b}$ is H, C$_1$-C$_6$alkyl, haloalkyl, halo, hydroxyl, nitro, cyano or amino:
R$^{7c}$ is H, C$_1$-C$_6$alkyl, haloalkyl, halo, hydroxyl, nitro, cyano or amino:
R$^{7d}$ is H, C$_1$-C$_6$alkyl, haloalkyl, halo, hydroxyl, nitro, cyano or amino:
V is

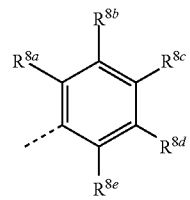

wherein:
R$^{8a}$ is H, C$_1$-C$_6$alkyl, haloalkyl, halo, hydroxyl, hydroxyalkyl, aryl or heteroaryl:
R$^{8b}$ is H, C$_1$-C$_6$alkyl, haloalkyl, halo, hydroxyl, hydroxyalkyl, aryl or heteroaryl:
R$^{8c}$ is H, C$_1$-C$_6$alkyl, haloalkyl, halo, hydroxyl, hydroxyalkyl, aryl or heteroaryl:
R$^{8d}$ is H, C$_1$-C$_6$alkyl, haloalkyl, halo, hydroxyl, hydroxyalkyl, aryl or heteroaryl:
R$^{8e}$ is H, C$_1$-C$_6$alkyl, haloalkyl, halo, hydroxyl, hydroxyalkyl, aryl or heteroaryl:
R$^1$ is H, —OR$^a$ or —SR$^a$, wherein R$^a$ is H or C$_1$-C$_6$alkyl:
R$^2$ is H, halo or C$_1$-C$_6$alkyl:
each R$^3$, R$^4$ and R$^5$ is independently selected from H, C$_1$-C$_6$alkyl, CF$_3$, halo and OR$^e$, wherein R$^e$ is H, C$_1$-C$_6$alkyl, C(O)R$^d$ or SO$_2$R$^d$, wherein R$^d$ is C$_1$-C$_6$ alkyl, CF$_3$, aryl or heteroaryl:
each R$^6$ is independently selected from —CO$_2$R$^e$, —CH$_2$OR$^e$, —CONR$^e$R$^f$ and tetrazol-5-yl; wherein each R$^e$ is independently selected from H, C$_1$-C$_6$alkyl, haloalkyl, hydroxyalkyl and aryl, and each R$^f$ is independently selected from H, C$_1$-C$_6$alkyl, C(O)R$^g$ and SO$_2$R$^g$, wherein R$^g$ is C$_1$-C$_6$ alkyl, CF$_3$, aryl or heteroaryl; and
wherein the dashed line represents the presence or absence of a bond; and when the dashed line is a bond, the resulting olefin geometry is cis or trans:
each aryl is C$_6$-C$_{14}$aryl; and
each heteroaryl comprises 5 to 14 ring atoms:
or a pharmaceutically acceptable salt thereof.

In embodiment (98), there are provided compounds of embodiment (97) wherein:

Y is O:
Z is CH$_2$:
R$^1$ is —OR$^a$, wherein R$^a$ is H:
R$^2$ is H:
each R$^3$, R$^4$ and R$^5$ is H:
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In embodiment (99), there are provided compounds of embodiment (97) wherein:
Q is aryl, wherein said aryl is optionally substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (100), there are provided compounds of embodiment (99), wherein:
Q is:

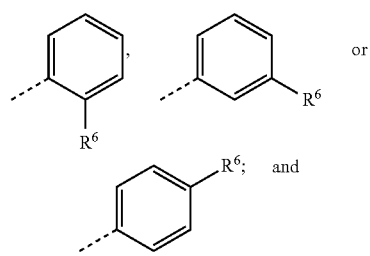

R$^6$ is —CO$_2$R$^e$, wherein R$^e$ is selected from H, C$_1$-C$_6$alkyl, haloalkyl, hydroxyalkyl and aryl:
or a pharmaceutically acceptable salt thereof.

In embodiment (101), there are provided compounds of embodiment (97) wherein:
Q is heteroaryl, wherein said heteroaryl is optionally substituted with one R$^6$; and
R$^6$ is —CO$_2$R$^e$, wherein R$^e$ is independently selected from H, C$_1$-C$_6$alkyl, haloalkyl, hydroxyalkyl and aryl; and
or a pharmaceutically acceptable salt thereof.

In embodiment (102), there are provided compounds of embodiment (101) wherein:
Y is O:
Z is CH$_2$:
Q is furanyl, thiopheneyl or thiazolyl, wherein each furanyl, thiopheneyl and thiazolyl group is substituted with one R$^6$:
R$^1$ is —OR$^a$, wherein R$^a$ is H:
R$^2$ is H:
each of R$^3$, R$^4$ and R$^5$ is H:
R$^6$ is —CO$_2$R$^e$, wherein R$^e$ is selected from H, C$_1$-C$_6$alkyl, haloalkyl, hydroxyalkyl and aryl:
the dashed line represents the presence of a bond, wherein the resulting olefin geometry is trans:
each aryl is C$_6$aryl; and
each heteroaryl comprises 5 or 6 ring atoms:
or a pharmaceutically acceptable salt thereof.

In embodiment (103), there are provided compounds of embodiment (1) having the structure of Formula 1c:

Formula Ic

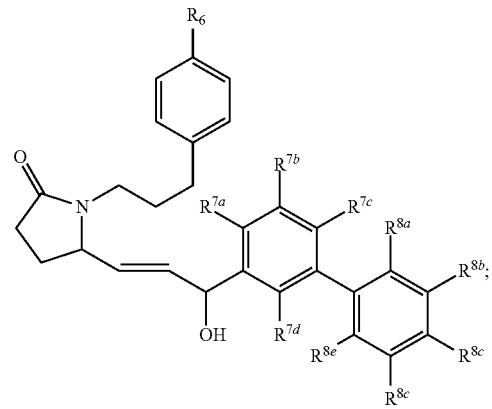

wherein:
R$^6$ is —CO$_2$R$^e$, wherein R$^e$ is independently selected from H, C$_1$-C$_6$alkyl, haloalkyl, hydroxyalkyl and aryl; and
R$^{7a}$ is H, C$_1$-C$_6$alkyl, haloalkyl, halo, hydroxyl, nitro, cyano or amino:
R$^{7b}$ is H, C$_1$-C$_6$alkyl, haloalkyl, halo, hydroxyl, nitro, cyano or amino:
R$^{7c}$ is H, C$_1$-C$_6$alkyl, haloalkyl, halo, hydroxyl, nitro, cyano or amino:
R$^{7d}$ is H, C$_1$-C$_6$alkyl, haloalkyl, halo, hydroxyl, nitro, cyano or amino:
R$^{8a}$ is H, C$_1$-C$_6$alkyl, haloalkyl, halo, hydroxyl, hydroxyalkyl, aryl or heteroaryl:
R$^{8b}$ is H, C$_1$-C$_6$alkyl, haloalkyl, halo, hydroxyl, hydroxyalkyl, aryl or heteroaryl:
R$^{8c}$ is H, C$_1$-C$_6$alkyl, haloalkyl, halo, hydroxyl, hydroxyalkyl, aryl or heteroaryl:
R$^{8d}$ is H, C$_1$-C$_6$alkyl, haloalkyl, halo, hydroxyl, hydroxyalkyl, aryl or heteroaryl; and
R$^{83}$ is H, C$_1$-C$_6$alkyl, haloalkyl, halo, hydroxyl, hydroxyalkyl, aryl or heteroaryl:
or a pharmaceutically acceptable salt thereof.

In embodiment (103), there are provided compounds of embodiment (1) having the structure of Formula 1d:

Formula Id

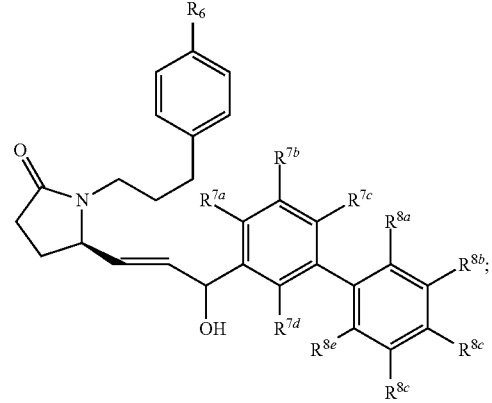

wherein:
R$^6$ is —CO$_2$R$^e$, wherein R$^e$ is independently selected from H, C$_1$-C$_6$alkyl, haloalkyl, hydroxyalkyl and aryl; and $R^{7a}$ is H, $C_1$-$C_6$alkyl, haloalkyl, halo, hydroxyl, nitro, cyano or amino:

$R^{7b}$ is H, $C_1$-$C_6$alkyl, haloalkyl, halo, hydroxyl, nitro, cyano or amino:

$R^{7c}$ is H, $C_1$-$C_6$alkyl, haloalkyl, halo, hydroxyl, nitro, cyano or amino:

$R^{7d}$ is H, $C_1$-$C_6$alkyl, haloalkyl, halo, hydroxyl, nitro, cyano or amino:

$R^{8a}$ is H, $C_1$-$C_6$alkyl, haloalkyl, halo, hydroxyl, hydroxyalkyl, aryl or heteroaryl:

$R^{8b}$ is H, $C_1$-$C_6$alkyl, haloalkyl, halo, hydroxyl, hydroxyalkyl, aryl or heteroaryl:

$R^{8c}$ is H, $C_1$-$C_6$alkyl, haloalkyl, halo, hydroxyl, hydroxyalkyl, aryl or heteroaryl:

$R^{8d}$ is H, $C_1$-$C_6$alkyl, haloalkyl, halo, hydroxyl, hydroxyalkyl, aryl or heteroaryl; and $R^{8d}$ is H, $C_1$-$C_6$alkyl, haloalkyl, halo, hydroxyl, hydroxyalkyl, aryl or heteroaryl:

or a pharmaceutically acceptable salt thereof.

In another embodiment, there are provided compounds of any one of the preceding or following embodiments, wherein:

when $R^1$ is —$OR^a$ and $R^a$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^2$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^3$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^4$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^5$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^7$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

embodiments wherein:

when $R^8$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^e$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^f$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding or following embodiments, wherein:

when $R^g$ is $C_1$-$C_6$alkyl, said $C_1$-$C_6$alkyl is selected from methyl, ethyl, n-propyl, isopropyl, n-butyl, and t-butyl.

In another embodiment, there are provided compounds of any one of the preceding embodiments, wherein at least one —H is replaced with —F.

In another embodiment, there are provided compounds of the preceding embodiment, wherein at least one of $R^2$, $R^3$, $R^4$, $R^5$ and $R^7$ is —F.

In another embodiment, there are provided compounds of any one of the preceding or following embodiments, wherein at least one —H is replaced with —$^2$H.

In another embodiment, there are provided compounds of Formula I, wherein the compounds have the structures and IUPAC names shown in Table 1.

TABLE 1

Structures and IUPAC Names of Exemplary Compounds of the Invention. IUPAC names of compounds were generated with ACD version 12.5.

| Structure | IUPAC Name |
|---|---|
| 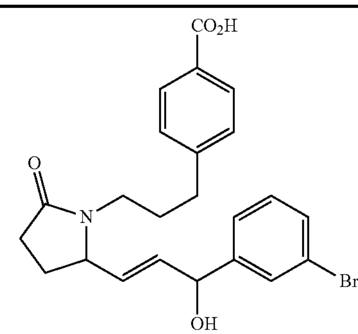 | 4-(3-{2-[(1E)-3-(3-bromophenyl)-3-hydroxyprop-1-en-1-yl]-5-oxopyrrolidin-1-yl}propyl)benzoic acid |
| 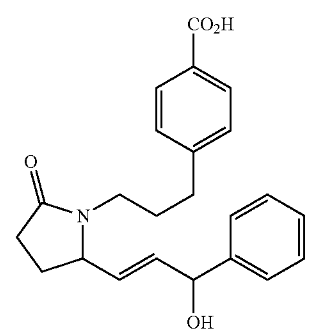 [SMILES: O=C(O)c1ccc(CCCN2C(=O)CCC2/C=C/C(O)c2ccccc2)cc1] | 4-(3-{2-[(1E)-3-hydroxy-3-phenylprop-1-en-1-yl]-5-oxopyrrolidin-1-yl}propyl)benzoic acid |
| 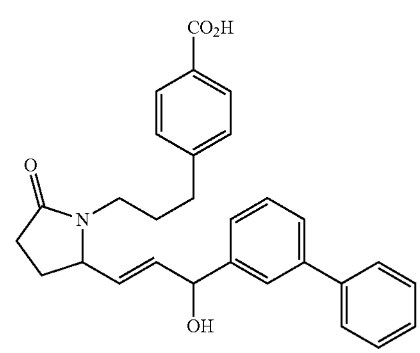 [SMILES: O=C(O)c1ccc(CCCN2C(=O)CCC2/C=C/C(O)c2cccc(-c3ccccc3)c2)cc1] | 4-(3-{2-[(1E)-3-(biphenyl-3-yl)-3-hydroxyprop-1-en-1-yl]-5-oxopyrrolidin-1-yl}propyl)benzoic acid |

TABLE 1-continued

Structures and IUPAC Names of Exemplary Compounds of the Invention. IUPAC names of compounds were generated with ACD version 12.5.

| Structure | IUPAC Name |
|---|---|
| | 4-(3-{2-[(1E)-3-hydroxy-3-(2'-methyl-biphenyl-3-yl)prop-1-en-1-yl]-5-oxo-pyrrolidin-1-yl}propyl)benzoic acid |
| | 4-(3-{2-[(1E)-3-hydroxy-3-(4'-hydroxy-2'-methyl-biphenyl-3-yl)prop-1-en-1-yl]-5-oxo-pyrrolidin-1-yl}propyl)benzoic acid |
| | 4-(3-{2-[(1E)-3-(4'-fluoro-2'-methyl-biphenyl-3-yl)-3-hydroxy-prop-1-en-1-yl]-5-oxo-pyrrolidin-1-yl}propyl)benzoic acid |
| | 4-(3-{2-[(1E)-3-(4'-chloro-2'-methyl-biphenyl-3-yl)-3-hydroxy-prop-1-en-1-yl]-5-oxo-pyrrolidin-1-yl}propyl)benzoic acid |
| | 4-(3-{2-[(1E)-3-(4'-chloro-2'-ethyl-biphenyl-3-yl)-3-hydroxy-prop-1-en-1-yl]-5-oxo-pyrrolidin-1-yl}propyl)benzoic acid |
| | 4-[3-(2-{(1E)-3-[4'-chloro-2'-(trifluoro-methyl)biphenyl-3-yl]-3-hydroxy-prop-1-en-1-yl}-5-oxo-pyrrolidin-1-yl)propyl]benzoic acid |
| | 4-[3-(2-{(1E)-3-[4'-chloro-2'-(hydroxy-methyl)biphenyl-3-yl]-3-hydroxy-prop-1-en-1-yl}-5-oxo-pyrrolidin-1-yl)propyl]benzoic acid |
| | 4-(3-{2-[(1E)-3-(4'-chloro-2',6'-dimethyl-biphenyl-3-yl)-3-hydroxy-prop-1-en-1-yl]-5-oxo-pyrrolidin-1-yl}propyl)benzoic acid |

TABLE 1-continued

Structures and IUPAC Names of Exemplary Compounds of the Invention. IUPAC names of compounds were generated with ACD version 12.5.

| Structure | IUPAC Name |
|---|---|
| | 4-(3-{2-[(1E)-3-(3',4'-dichloro-2'-methyl-biphenyl-3-yl)-3-hydroxy-prop-1-en-1-yl]-5-oxo-pyrrolidin-1-yl}propyl)benzoic acid |
| | 4-(3-{2-[(1E)-3-(4'-chloro-2'-propyl-biphenyl-3-yl)-3-hydroxy-prop-1-en-1-yl]-5-oxo-pyrrolidin-1-yl}propyl)benzoic acid |
| | 4-(3-{2-[(1E)-3-(2'-tert-butyl-4'-chloro-biphenyl-3-yl)-3-hydroxy-prop-1-en-1-yl]-5-oxo-pyrrolidin-1-yl}propyl)benzoic acid |
| | 4-(3-{2-[(1E)-3-(2'-butyl-4'-chloro-biphenyl-3-yl)-3-hydroxy-prop-1-en-1-yl]-5-oxo-pyrrolidin-1-yl}propyl)benzoic acid |
| | 4-[3-(2-{(1E)-3-hydroxy-3-[4'-hydroxy-2'-(propan-2-yl)biphenyl-3-yl]prop-1-en-1-yl}-5-oxo-pyrrolidin-1-yl)propyl]benzoic acid |
| | 4-[3-(2-{(1E)-3-[5-(4-chloro-2-methyl-phenyl)thiophen-2-yl]-3-hydroxy-prop-1-en-1-yl}-5-oxo-pyrrolidin-1-yl)propyl]benzoic acid |
| | 4-(3-{2-[(1E)-3-(4'-chloro-5-fluoro-2'-methyl-biphenyl-3-yl)-3-hydroxy-prop-1-en-1-yl]-5-oxo-pyrrolidin-1-yl}propyl)benzoic acid |
| | 4-(3-{2-[(1E)-3-(4'-chloro-6-fluoro-2'-methyl-biphenyl-3-yl)-3-hydroxy-prop-1-en-1-yl]-5-oxo-pyrrolidin-1-yl}propyl)benzoic acid |

In another embodiment, there is provided a pharmaceutical composition comprising a compound of Formula I, or a pharmaceutically acceptable salt thereof.

In another embodiment, there is provided a pharmaceutical composition comprising a compound of Formula I, or a pharmaceutically acceptable salt thereof, in a pharmaceutically acceptable carrier.

In another embodiment, there is provided a pharmaceutical composition comprising a compound selected from the compounds of Table 1 and Table 2, and pharmaceutically acceptable salts thereof.

In another embodiment, there is provided a pharmaceutical composition comprising a compound selected from the compounds of Table 1 and Table 2, and pharmaceutically acceptable salts thereof, in a pharmaceutically acceptable carrier.

In another embodiment, there is provided a method of treating a wound, reducing a scar, or repairing skin in a subject in need of such treatment, reduction, or repair, the method comprising administering to the subject a compound of Formula I or a pharmaceutically acceptable salt thereof.

In another embodiment, there is provided a method of treating a wound, reducing a scar, or repairing skin in a subject in need of such treatment, reduction, or repair, the method comprising administering to the subject an effective amount of a compound of Formula I or a pharmaceutically acceptable salt thereof.

Compounds of the invention may be synthesized in a variety of ways known to those skilled in the art. Scheme 1 set forth below outlines one synthetic route to compounds of the invention.

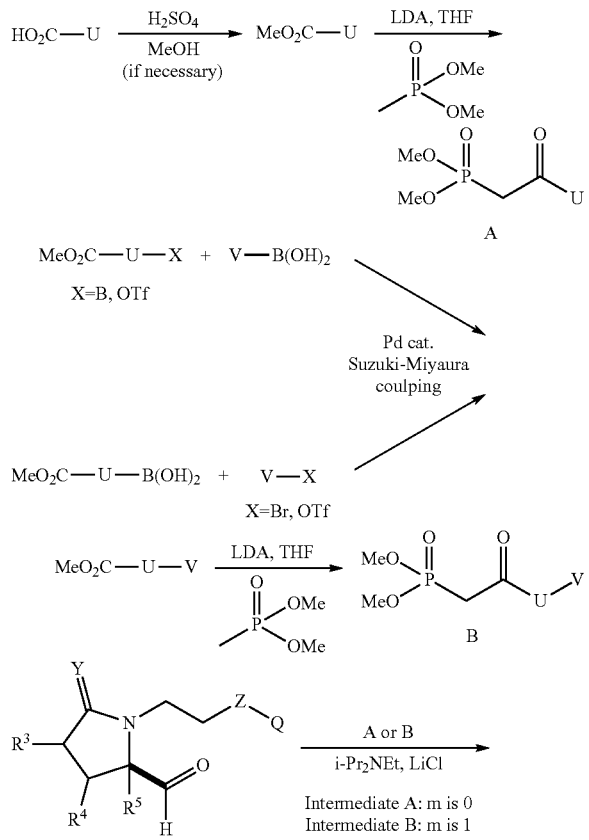

Scheme 1.

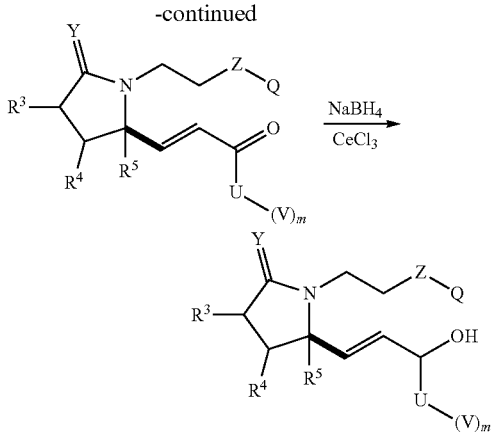

As used herein, the term "skin blemish" includes a flesh wound, scar, or wrinkle on any region of the skin of a body.

A "flesh wound" can be any area in which the structural integrity of the exterior surface of the skin is compromised. A flesh wound can be due to incision, laceration, abrasion, thermal burn, chemical burn, radiation or puncture of the skin. The wound can be superficial or extend to the deeper layers of the dermis, subcutaneous, deep fascia, muscle, bone or other internal organs.

A "scar" is an area of fibrous tissue (fibrosis) that replaces normal skin (or other tissue) after injury or disease. Scar types include hypertrophic scars, recessed scars, and stretch marks.

Hypertrophic scars occur when the body overproduces collagen, which causes the scar to be raised above the surrounding skin. An example of a hypertrophic scar is a keloid scar. Atrophic, or recessed scars, have a sunken appearance and result when underlying support structure in the skin is lost. Stretch marks (striae) occur when skin is stretched rapidly (i.e., due to significant weight gain or growth spurt), or when skin is put under tension during the healing process, typically near a joint. As used herein, the term "scar" encompasses any type of scar in the skin due to any cause.

As used herein, the term "wrinkle" is a fold, ridge, crease, furrow, pit, crater, or sunken area in the skin that can be caused by habitual facial expressions, loss of collagen and/or elasticity due to aging, sun damage, smoking, poor hydration, and various other factors. A wrinkle can range from a deep crease to a fine line. Wrinkles occurring on any part of a body, in particular, wrinkles on head or neck of a subject are contemplated herein. Wrinkles that can be treated in accordance with the disclosure include, but are not limited to, a brow furrow, crows feet, nasolabial fold, one or more lines under the eyes or between the eye brows, and combinations thereof.

As used herein, "treatment" means to alleviate (or to eliminate) one or more features of a skin blemish either temporarily or permanently. When the compositions are administered to treat a wound, the compositions promote normal healing compared to a wound without the administration. That is, the size (length, depth, height and/or width), character, color and/or texture of the treated wound more closely resemble normal, non-wounded tissue. In this regard, treatment of a wound with the disclosed compositions can prevent, minimize or improve the appearance of a scar formation resulting from healing of the wound. Further, when the disclosed compositions are administered to treat a wrinkle, the wrinkle is treated if the appearance or prominence of the wrinkle is visibly or clinically diminished. That is the length and/or depth is decreased compared to the wrinkle prior to treatment. Alternatively, treatment can comprise prevention of a wrinkle. In this regard, the disclosed compositions can be applied to a region of the skin that typically develops a wrinkle, such as a forehead, lips, eyelids, nasolabial fold, skin under an eye, or between the eye brows in order to prevent the development of a wrinkle.

The disclosed compositions can be administered to prevent scar formation not associated with a wound, such as a stretch mark, or scars resulting from acne, chicken pox, measles or other disease states. In certain embodiments, the disclosed compositions are administered to the area of skin expansion in order to prevent formation of such scars. In these embodiments, the composition can be administered to any region of a face, abdomen, breasts, arms, legs, buttocks, back, or any other area where the skin is susceptible to developing a scar.

The compositions can be administered prior to, concurrently with, and/or after the development of the skin blemish. For instance, the disclosed compositions can be administered prior to an incision, during a surgical procedure, and/or any time post-operatively, and then additionally administered after the procedure as the healing process occurs. In another example, the compositions can be administered during pregnancy to prevent stretch marks. Alternately, the compositions can be administered after the development of a blemish.

The compositions may be administered between 1 and 7 days a week, for a period of time necessary to achieve the desired results, which may be several days to several months. The compositions can be administered once or several times (2, 3, 4, or more times) a day depending on the desired effect. In certain embodiments, the compositions can be administered every 1, 2, 3, 4, 5, 6, or 7 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or more. In certain embodiments, the compositions can be administered on an ongoing basis to maintain a desired result.

The disclosed compounds can be administered as part of a composition. As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed compounds in order to provide a desired composition. Those of ordinary skill in the art will recognize a number of carriers that are well known for making specific pharmaceutical and/or cosmetic compositions. Desirably, the carrier is suitable for application to keratinous surfaces or other areas of the body. Upon application, acceptable carriers are substantially free of adverse reactions with skin and other keratinous surfaces. For example, the carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks. In accordance with one embodiment, the composition includes a dermatologically compatible vehicle or carrier. The vehicle which may be employed for preparing compositions may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

Examples of additional agents which can be included in the present compositions are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anesthetic agents can include lidocaine, benzocaine, butamben, dibucaine, oxybuprocaine, pramoxine, proparacaine, proxymetacaine, tetracaine, and combinations thereof. Anti-scarring agents can include IFN-gamma., fluorouracil, poly (lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and derivatives and combinations thereof. Additionally, active agents such as epinephrine, thymidine, cytidine, uridine, antiypyrin, aminocaproic acid, tranexamic acid, eucalyptol, allantoin, glycerin, and sodium selenite, can be included. Formulations can further comprise degradation inhibitors. Degradation inhibitors, include but are not limited to, glycosaminoglycans (e.g., heparin, heparin sulfate, dermatan sulfate, chrondroitin sulfate, o-sulfated HA, lnamarin, and amygdalin), antioxidants (e.g. ascorbic acid, melatonin, vitamin C, vitamin E), proteins (e.g., serum hyaluronidase inhibitor), and fatty acids (e.g. saturated $C_{10}$ to $C_{22}$ fatty acids). In certain embodiments, additional active agent is an antioxidant. In certain embodiments, the antioxidant comprises a vitamin C and/or a vitamin E such as D-alpha-tocopheryl polyethylene glycol 1000 succinate (TPGS).

The disclosed compositions are well suited for topical, subcutaneous, intradermal, subdermal, subcutaneous, and transdermal administration. Topical administration relates to the use of a composition applied to the surface of the skin at the site of a skin blemish for exertion of local action. Accordingly, such topical compositions include those pharmaceutical or cosmetic forms in which the composition is applied externally by direct contact with the skin surface to be treated, such as the face, neck, arms, legs, and/or torso. Conventional pharmaceutical or cosmetic forms for this purpose include ointments, liniments, creams, shampoos, lotions, pastes, jellies, sprays, aerosols, and the like, and may further be applied directly or in patches or impregnated dressings depending on blemish and skin region to be treated. The term "ointment" embraces formulations (including creams) having oleaginous, water-soluble and emulsion-type bases, e.g., petrolatum, lanolin, polyethylene glycols, as well as mixtures of these.

The compositions are appropriate for mesotherapy applications as well. Mesotherapy is a non-surgical cosmetic treatment technique involving intra-epidermal, intra-dermal, and/or subcutaneous injection of a composition. The compositions are administered in the form of small multiple droplets into the epidermis, dermo-epidermal junction, and/or the dermis.

In accordance with the disclosure, a pharmaceutical or cosmetic composition can optionally include one or more agents such as, without limitation, emulsifying agents, wetting agents, sweetening or flavoring agents, tonicity adjusters, preservatives, buffers, antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the pharmaceutical compositions described herein include, without limitation, benzalkonium chloride, chlorobutanol, thimerosal, phenyl mercuric acetate, and phenyl mercuric nitrate. Various buffers and means for adjusting pH can be used to prepare a pharmaceutical composition, including but not limited to, acetate buffers, citrate buffers, phosphate buffers and borate buffers. Similarly, antioxidants useful in pharmaceutical compositions are well known in the art and include for example, sodium metabisulfite, sodium thiosulfate, acetylcysteine, butylated hydroxyanisole and butylated hydroxytoluene. Flavonoids are compounds found in plants that are well known to have diverse beneficial biochemical and antioxidant effects. Subcategories of flavonoids include: flavones, flavonols, flavanonse and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, and hydrolysable tannis. It is understood that these and other substances known in the art can be included in a pharmaceutical or cosmetic composition disclosed herein.

As used herein, the term "therapeutically effective amount" means the amount of the pharmaceutical or cosmetic composition that will elicit the biological, medical, or cosmetic response of a subject in need thereof that is being sought by the researcher, veterinarian, medical doctor or other clinician. In some embodiments, the subject in need thereof is a mammal. In certain embodiments, the mammal is human. Effective amounts of the compound may be determined by one of ordinary skill in the art but will vary depending on the compound employed, frequency of application and desired result, and will generally range from about 0.0000001% to about 50%, by weight, of the composition, preferably from about 0.001% to about 50%, by weight, of total composition, more preferably from about 0.001% to about 30%, by weight of the composition. In certain embodiments, the compound is about 0.004% by weight of the composition.

The compounds described herein may be administered at least in the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.0001 mg/kg/day to about 100 mg/kg/day or about 0.01 mg/kg/day to about 100 mg/kg/day. However, the actual amount of the compound to be administered in any given case will be determined by a physician taking into account the relevant circumstances, such as the age and weight of a patient, patient's general physical condition, severity of the skin blemish, and route of administration. In some instances, dosing is evaluated on a case-by-case basis.

Additionally, compositions may be designed to delay release of the compound over a given period of time, or to carefully control the amount of compound released at a given time during the course of treatment.

The pH of the disclosed compositions can be about 3 to about 8.0, or about 6.5 to about 7.5. In certain embodiments, the pH of the formulation is about 7.0 to about 7.4 or about 7.1 to about 7.3.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

All the reagents, solvents, catalysts for which the synthesis is not described, including compounds of the structure U—C(O)OMe (or U—C(O)OH) and X—U—C(O)OMe (Schemes 1 and 2), were purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

NMR spectra were obtained on a Varian 600 MHz NMR instrument, using $CDCl_3$ as the solvent and internal reference at room temperature unless otherwise noted. Mass spectra were obtained using a Shimadzu Liquid Chromatograph Mass Spectrometer Ion Trap Time of Flight (LCMS-IT-TOF) instrument in electrospray positive and negative modes; samples were direct injected with methanol as sample diluent.

The following Examples and Schemes 1 and 2 illustrate how compounds according to the invention can be made. Those skilled in the art will be routinely able to modify and/or adapt the methods of the Schemes and the following Examples to synthesize any compound of the invention covered by Formula I.

Example A (R)-methyl 4-(3-(2-formyl-5-oxopyrrolidin-1-yl)propyl)benzoate (R)-methyl 4-(3-(2-formyl-5-oxopyrrolidin-1-yl)propyl) benzoate was prepared essentially as described in WO 2002/042268 (incorporated in its entirety herein by reference).

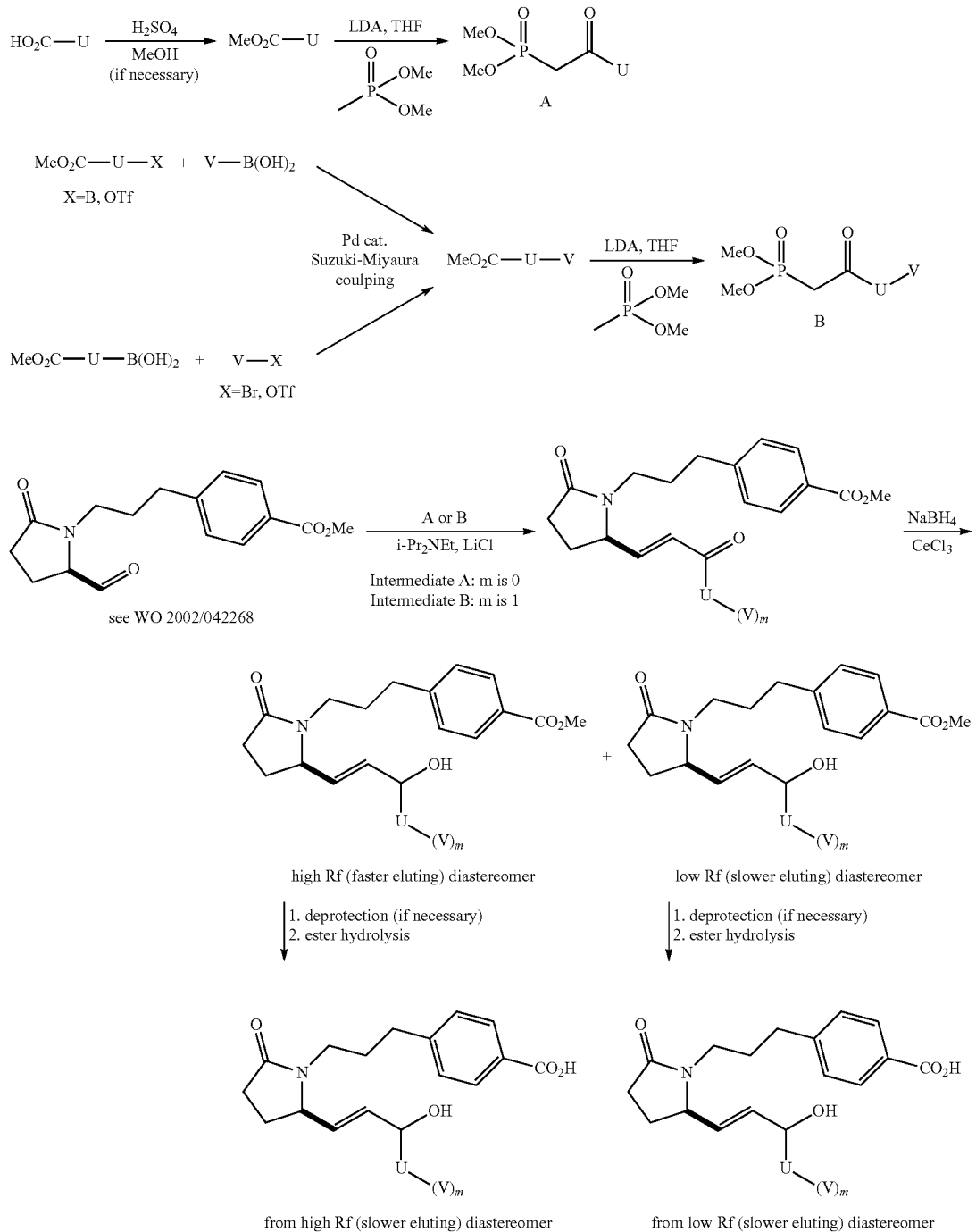

Example B

Separation of Diastereomers

As shown in Scheme 2, the synthesis of compounds of the invention involves the coupling of (R)-methyl 4-(3-(2-formyl-5-oxopyrrolidin-1-yl)propyl)benzoate (from Example A) with intermediate A or B (Scheme 2) to give the corresponding ketone, which is subsequently reduced to give a mixture of "high Rf" and "low Rf" diastereomeric benzoate esters. Thereafter (or after further modifications, according to the following examples), the diasteromeric mixture is separated using chromatography on silica gel. Then, each diastereomer is converted to the corresponding carboxylic acid to obtain the final product. Examples 1-37 and Table 2 make reference to the relative retention times of the benzoate ester intermediates used to prepare the corresponding carboxylic acids. For example, conversion of the earlier eluting (high Rf) benzoate ester to the corresponding carboxylic acid gives the product obtained "from high $R^f$ ester." Similarly, conversion of the later eluting benzoate ester to the corresponding carboxylic acid gives the product obtained "from low Rf ester."

Example 1

4-(3-{2(R)-[(1E)-3-(3-bromophenyl)-3-hydroxy-prop-1-en-1-yl]-5-oxopyrrolidin-1-yl}propyl)benzoic acid (from High $R^f$ Ester)

Step 1. Dimethyl (2-(3-bromophenyl)-2-oxoethyl)phosphonate. Lithium diisopropylamide (1.86 mL of a 2.0 M solution in tetrahydrofuran (THF, 3.72 mmol) was added to a solution of dimethyl methylphosphonate (300 mg, 2.42 mmol) and methyl 3-bromobenzoate (400 mg, 1.86 mmol) in THF (4.65 mL) at −5° C. The mixture was stirred at approximately 0° C. until complete consumption of the ester was observed by mass spectrometry analysis. Upon completion, the reaction mixture was quenched with 5 M HCl, adjusting to approximately pH 7. The mixture was extracted with ethyl acetate (EtOAc; 2×), then the extracts were dried (MgSO$_4$), filtered and concentrated in vacuo. The resulting crude residue was purified on silica gel using a Teledyne-Isco Combiflash machine (4 g column, hexanes to 100% EtOAc, gradient), to afford 234 mg (41%) of dimethyl (2-(3-bromophenyl)-2-oxoethyl)phosphonate.

Step 2. (R,E)-methyl 4-(3-(2-(3-(3-bromophenyl)-3-oxoprop-1-en-1-yl)-5-oxopyrrolidin-1-yl)propyl)benzoate. N,N-Diisopropylethylamine (98 mg, 0.76 mmol) was added to a mixture of (R)-methyl 4-(3-(2-formyl-5-oxopyrrolidin-1-yl)propyl)benzoate (200 mg, 0.69 mmol), dimethyl (2-(3-bromophenyl)-2-oxoethyl)phosphonate (234 mg, 0.76 mmol) and lithium chloride (32 mg, 0.76 mmol) in MeCN (1 mL) at room temperature. The reaction mixture was maintained at room temperature overnight, then was diluted with water (50 mL) and extracted with EtOAc (50 mL). The organic phase was washed with brine (100 mL), dried (MgSO$_4$), filtered and concentrated in vacuo. The resulting crude residue was purified on silica gel using a Teledyne-Isco Combiflash machine (4 g column, hexanes to 100% EtOAc, gradient), to afford 121 mg (37%) of (R,E)-methyl 4-(3-(2-(3-(3-bromophenyl)-3-oxoprop-1-en-1-yl)-5-oxopyrrolidin-1-yl)propyl)benzoate.

Step 3. Methyl 4-(3-((2R)-2-((E)-3-(3-bromophenyl)-3-hydroxyprop-1-en-1-yl)-5-oxopyrrolidin-1-yl)propyl)benzoate. Cerium trichloride heptahydrate (201 mg, 0.26 mmol) and sodium borohydride (9.7 mg, 0.26 mmol) were added sequentially to a solution of (R,E)-methyl 4-(3-(2-(3-(3-bromophenyl)-3-oxoprop-1-en-1-yl)-5-oxopyrrolidin-1-yl)propyl)benzoate (121 mg, 0.26 mmol) in methanol (0.65 mL). After 5 minutes, the reaction mixture was concentrated in vacuo and quenched by drop-wise addition of saturated aqueous NH$_4$Cl (5 mL). The mixture was extracted with EtOAc. The organic phase was dried (MgSO$_4$), filtered and concentrated in vacuo. The resulting crude residue was purified on silica gel using a Teledyne-Isco Combiflash machine (4 g column, hexanes to 100% EtOAc, 90 minute gradient), to afford 44 mg (36%) of high $R^f$ methyl 4-(3-((2R)-2-((E)-3-(3-bromophenyl)-3-hydroxyprop-1-en-1-yl)-5-oxopyrrolidin-1-yl)propyl)benzoate and 22 mg (18%) of low $R^f$ methyl 4-(3-((2R)-2-((E)-3-(3-bromophenyl)-3-hydroxyprop-1-en-1-yl)-5-oxopyrrolidin-1-yl)propyl)benzoate.

Step 4. 4-(3-{2(R)-[(1E)-3-(3-bromophenyl)-3-hydroxyprop-1-en-1-yl]-5-oxopyrrolidin-1-yl}propyl)benzoic acid (from high $R^f$ ester). Rabbit liver esterase (Sigma, 12 units), was added to a mixture of methyl 4-(3-((2R)-2-((E)-3-(3-bromophenyl)-3-hydroxyprop-1-en-1-yl)-5-oxopyrrolidin-1-yl)propyl)benzoate (high Rf, 22 mg, 0.047 mmol), MeCN (0.2 mL) and pH 7.2 buffer (2 mL). The reaction was stirred vigorously for 1 day at room temperature, then 2 g of silica gel was added and the mixture was concentrated in vacuo. The resulting crude residue was purified on silica gel using a Teledyne-Isco Combiflash machine (4 g column, CH$_2$Cl$_2$ to 15% methanol/CH$_2$Cl$_2$, 120 minute gradient), to afford 15 mg (quant.) of 4-(3-{2(R)-[(1E)-3-(3-bromophenyl)-3-hydroxyprop-1-en-1-yl]-5-oxopyrrolidin-1-yl}propyl)benzoic acid.

Example 2

4-(3-{2(R)-[(1E)-3-(3-bromophenyl)-3-hydroxyprop-1-en-1-yl]-5-oxopyrrolidin-1-yl}propyl)benzoic acid (from Low $R^f$ Ester)

In accordance with the procedure of Example 1, step 4, methyl 4-(3-((2R)-2-((E)-3-(3-bromophenyl)-3-hydroxyprop-1-en-1-yl)-5-oxopyrrolidin-1-yl)propyl)benzoate (low Rf, 11 mg, 0.023 mmol), was converted into 5 mg (68%) of 4-(3-{2(R)-[(1E)-3-(3-bromophenyl)-3-hydroxyprop-1-en-1-yl]-5-oxopyrrolidin-1-yl}propyl)benzoic acid.

Example 3

4-(3-{2(R)-[(1E)-3-hydroxy-3-phenylprop-1-en-1-yl]-5-oxopyrrolidin-1-yl}propyl)benzoic acid (from High $R^f$ Ester)

Step 1. Dimethyl (2-oxo-2-phenylethyl)phosphonate. In accordance with the procedure of Example 1, step 1, methyl benzoate (500 mg, 3.67 mmol) was converted into 173 mg (21%) of dimethyl (2-oxo-2-phenylethyl)phosphonate.

Step 2. (R,E)-Methyl 4-(3-(2-oxo-5-(3-oxo-3-phenylprop-1-en-1-yl)pyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-oxo-2-phenylethyl)phosphonate (174 mg, 0.76 mmol) were converted into 81 mg (30%) of (R,E)-methyl 4-(3-(2-oxo-5-(3-oxo-3-phenylprop-1-en-1-yl)pyrrolidin-1-yl)propyl)benzoate.

Step 3. Methyl 4-(3-((2R)-2-((E)-3-hydroxy-3-phenylprop-1-en-1-yl)-5-oxopyrrolidin-1-yl)propyl)benzoate. In accordance with the procedure of Example 1, step 3, (R,E)-methyl 4-(3-(2-oxo-5-(3-oxo-3-phenylprop-1-en-1-yl)pyrrolidin-1-yl)propyl)benzoate (81 mg, 0.21 mmol) was converted into 50 mg (61%) of high R$^f$ methyl 4-(3-((2R)-2-((E)-3-hydroxy-3-phenylprop-1-en-1-yl)-5-oxopyrrolidin-1-yl)propyl)benzoate and 8 mg (10%) of low R$^f$ methyl 4-(3-((2R)-2-((E)-3-hydroxy-3-phenylprop-1-en-1-yl)-5-oxopyrrolidin-1-yl)propyl)benzoate.

Step 4. 4-(3-{2(R)-[(1E)-3-hydroxy-3-phenylprop-1-en-1-yl]-5-oxopyrrolidin-1-yl}propyl)benzoic acid (from high R$^f$ ester). In accordance with the procedure of Example 1, step 4, of methyl 4-(3-((2R)-2-((E)-3-hydroxy-3-phenylprop-1-en-1-yl)-5-oxopyrrolidin-1-yl)propyl)benzoate (high Rf, 25 mg, 0.059 mmol) was converted into 17 mg (90%) of 4-(3-{2(R)-[(1E)-3-hydroxy-3-phenylprop-1-en-1-yl]-5-oxopyrrolidin-1-yl}propyl)benzoic acid.

Example 4

4-(3-{2(R)-[(1E)-3-hydroxy-3-phenylprop-1-en-1-yl]-5-oxopyrrolidin-1-yl}propyl)benzoic acid (from Low R$^f$ Ester)

In accordance with the procedure of Example 1, step 4, of methyl 4-(3-((2R)-2-((E)-3-hydroxy-3-phenylprop-1-en-1-yl)-5-oxopyrrolidin-1-yl)propyl)benzoate (low Rf, 4 mg, 0.009 mmol) was converted into 2 mg (66%) of 4-(3-{2(R)-[(1E)-3-hydroxy-3-phenylprop-1-en-1-yl]-5-oxopyrrolidin-1-yl}propyl)benzoic acid.

Example 5

4-(3-{2(R)-[(1E)-3-(biphenyl-3-yl)-3-hydroxyprop-1-en-1-yl]-5-oxopyrrolidin-1-yl}propyl)benzoic acid (from High R$^f$ Ester)

Step 1. Methyl [1,1'-biphenyl]-3-carboxylate. Concentrated H$_2$SO$_4$ (1.26 mL, 15.1 mmol) was added slowly to a 0° C. solution of [1,1'-biphenyl]-3-carboxylic acid (1.0 g, 5.0 mmol) in methanol (25 mL). The reaction mixture was warmed to room temperature, then was heated at 50° C. overnight. The mixture was then cooled and carefully quenched with saturated aqueous sodium bicarbonate until the pH of the mixture was less than 7. The mixture was extracted with EtOAc (2×200 mL). The combined extracts were washed with water (50 mL) and brine (50 mL), then dried (MgSO$_4$), filtered and concentrated in vacuo. The resulting crude residue was purified on silica gel using a Teledyne-Isco Combiflash machine (40 g column, hexanes to 100% EtOAc, gradient over 45 minutes), to afford 1.07 g (quant.) of methyl [1,1'-biphenyl]-3-carboxylate.

Step 2. Dimethyl (2-([1,1'-biphenyl]-3-yl)-2-oxoethyl)phosphonate. In accordance with the procedure of Example 1, step 1, methyl [1,1'-biphenyl]-3-carboxylate (150 mg, 0.71 mmol) was converted into 215 mg (quant.) of dimethyl (2-([1,1'-biphenyl]-3-yl)-2-oxoethyl)phosphonate.

Step 3. (R,E)-Methyl 4-(3-(2-(3-([1,1'-biphenyl]-3-oxoprop-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-([1,1'-biphenyl]-3-yl)-2-oxoethyl)phosphonate (210 mg, 0.69 mmol) were converted into 119 mg (37%) of (R,E)-methyl 4-(3-(2-(3-([1,1'-biphenyl]-3-yl)-3-oxoprop-1-en-1-yl)-5-oxopyrrolidin-1-yl)propyl)benzoate.

Step 5. Methyl 4-(3-((2R)-2-((E)-3-([1,1'-biphenyl]-3-yl)-3-hydroxyprop-1-en-1-yl)-5-oxopyrrolidin-1-yl)propyl)benzoate. In accordance with the procedure of Example 1, step 3 (R,E)-methyl 4-(3-(2-(3-([1,1'-biphenyl]-3-yl)-3-oxoprop-1-en-1-yl)-5-oxopyrrolidin-1-yl)propyl)benzoate (119 mg, 0.25 mmol) was converted into 19 mg (16%) of high R$^f$ methyl 4-(3-((2R)-2-((E)-3-([1,1'-biphenyl]-3-yl)-3-hydroxyprop-1-en-1-yl)-5-oxopyrrolidin-1-yl)propyl)benzoate and 7 mg (6%) of low R$^f$ methyl 4-(3-((2R)-2-((E)-3-([1,1'-biphenyl]-3-yl)-3-hydroxyprop-1-en-1-yl)-5-oxopyrrolidin-1-yl)propyl)benzoate.

Step 6. 4-(3-{2(R)-[(1E)-3-(biphenyl-3-yl)-3-hydroxyprop-1-en-1-yl]-5-oxopyrrolidin-1-yl}propyl)benzoic acid (from high R$^f$ ester). In accordance with the procedure of Example 1, step 4, methyl 4-(3-((2R)-2-((E)-3-([1,1'-biphenyl]-3-yl)-3-hydroxyprop-1-en-1-yl)-5-oxopyrrolidin-1-yl)propyl)benzoate (high Rf, 19 mg, 0.040 mmol) was converted into 14 mg (76%) of 4-(3-{2(R)-[(1E)-3-(biphenyl-3-yl)-3-hydroxyprop-1-en-1-yl]-5-oxopyrrolidin-1-yl}propyl)benzoic acid.

Example 6

4-(3-{2(R)-[(1E)-3-(biphenyl-3-yl)-3-hydroxyprop-1-en-1-yl]-5-oxopyrrolidin-1-yl}propyl)benzoic acid (from Low R$^f$ Ester)

In accordance with the procedure of Example 1, step 4, methyl 4-(3-((2R)-2-((E)-3-([1,1'-biphenyl]-3-yl)-3-hydroxyprop-1-en-1-yl)-5-oxopyrrolidin-1-yl)propyl)benzoate (low Rf, 7 mg, 0.015 mmol) was converted into 3 mg (44%) of 4-(3-{2(R)-[(1E)-3-(biphenyl-3-yl)-3-hydroxyprop-1-en-1-yl]-5-oxopyrrolidin-1-yl}propyl)benzoic acid.

Example 7

4-(3-{2(R)-[(1E)-3-hydroxy-3-(2'-methylbiphenyl-3-yl)prop-1-en-1-yl]-5-oxopyrrolidin-1-yl}propyl)benzoic acid (from High R$^f$ Ester)

Step 1. Methyl 2'-methyl-[1,1'-biphenyl]-3-carboxylate. A 100 mL round-bottomed flask was charged with methyl 3-bromobenzoate (400 mg, 1.81 mmol), cesium carbonate (1.18 g, 3.62 mmol) and o-tolylboronic acid (492 mg, 3.62 mmol) and purged with nitrogen. Toluene (20 mL) was added and then tetrakis(triphenylphosphine) palladium (0) (21 mg, 0.18 mmol) was added to the mixture. The reaction was heated at 80° C. Upon completion (followed by TLC analysis), the reaction was cooled, diluted with toluene and filtered through celite. The filtrate was concentrated in vacuo. The resulting crude residue was purified on silica gel using a Teledyne-Isco Combiflash machine (80 g column, hexanes to 100% EtOAc, gradient), to afford an inseparable mixture of methyl 2'-methyl-[1,1'-biphenyl]-3-carboxylate and starting ester, which was used in the next step without further purification.

Step 2. Dimethyl (2-(2'-methyl-[1,1'-biphenyl]-3-yl)-2-oxoethyl)phosphonate. In accordance with the procedure of Example 1, step 1, impure methyl 2'-methyl-[1,1'-biphenyl]-3-carboxylate (~1.81 mmol) was converted into 484 mg (84% for 2 steps) of dimethyl (2-(2'-methyl-[1,1'-biphenyl]-3-yl)-2-oxoethyl)phosphonate.

Step 3. (R,E)-methyl 4-(3-(2-(3-(2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol), of dimethyl (2-(2'-methyl-[1,1'-biphenyl]-3-yl)-2-oxoethyl)phosphonate (242 mg, 0.76 mmol) were converted into 200 mg (60%) of (R,E)-methyl 4-(3-(2-(3-(2'-methyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-hydroxy-3-(2'-methyl-[1,1'-biphenyl]-3-yl)prop-1-en-1-yl)-5-oxopyrrolidin-1-yl)propyl)benzoic acid. In accordance with the procedure of Example 1, step 3, (R,E)-methyl 4-(3-(2-(3-(2'-methyl-[1,1'-biphenyl]-3-yl)-3-oxoprop-1-en-1-yl)-5-oxopyrrolidin-1-yl)propyl)benzoate (200 mg, 0.42 mmol) was converted into 62 mg (31%) of high $R^f$ methyl 4-(3-((2R)-2-((E)-3-hydroxy-3-(2'-methyl-[1,1'-biphenyl]-3-yl)prop-1-en-1-yl)-5-oxopyrrolidin-1-yl)propyl)benzoic acid and 28 mg (14%) of low $R^f$ methyl 4-(3-((2R)-2-((E)-3-hydroxy-3-(2'-methyl-[1,1'-biphenyl]-3-yl)prop-1-en-1-yl)-5-oxopyrrolidin-1-yl)propyl)benzoic acid.

Step 5. 4-(3-{2(R)-[(1E)-3-hydroxy-3-(2'-methylbiphenyl-3-yl)prop-1-en-1-yl]-5-oxopyrrolidin-1-yl}propyl)benzoic acid (from high $R^f$ ester). Lithium hydroxide (0.064 mL of a 1.0 M aqueous solution, 0.064 mmol) was added to a solution of methyl 4-(3-((2R)-2-((E)-3-hydroxy-3-(2'-methyl-[1,1'-biphenyl]-3-yl)prop-1-en-1-yl)-5-oxopyrrolidin-1-yl)propyl)benzoic acid (high Rf, 31 mg, 0.064 mmol) in THF (1.0 mL). The reaction was stirred at 35° C. overnight. The cooled reaction was acidified with aqueous 1 N HCl and extracted with EtOAc (50 mL). The organic phase was dried (MgSO$_4$), filtered and concentrated to afford 17 mg (56%) of 4-(3-{2(R)-[(1E)-3-hydroxy-3-(2'-methylbiphenyl-3-yl)prop-1-en-1-yl]-5-oxopyrrolidin-1-yl}propyl)benzoic acid.

Example 8

4-(3-{2(R)-[(1E)-3-hydroxy-3-(2'-methylbiphenyl-3-yl)prop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-hydroxy-3-(2'-methyl-[1,1'-biphenyl]-3-yl)prop-1-en-1-yl)-5-oxopyrrolidin-1-yl)propyl)benzoic acid (low Rf, 14 mg, 0.029 mmol) was converted into 7 mg (52%) of 4-(3-{2(R)-[(1E)-3-hydroxy-3-(2'-methylbiphenyl-3-yl)prop-1-en-1-yl]-5-oxopyrrolidin-1-yl}propyl)benzoic acid.

Example 9

4-(3-{2(R)-[(1E)-3-hydroxy-3-(4'-hydroxy-2'-methylbiphenyl-3-yl)prop-1-en-1-yl]-5-oxopyrrolidin-1-yl}propyl)benzoic acid (from High $R^f$ Ester)

Step 1. (R,E)-Methyl 4-(3-(2-(3-(4'-hydroxy-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-hydroxy-2'-methyl-[1,1'-biphenyl]-3-yl)-2-oxoethyl)phosphonate (253 mg, 0.76 mmol; prepared according to Elworthy, US 2004/0142969, and Elworthy et al., Lactams as EP4 prostanoid receptor subtype selective agonists. Part 1: 2-Pyrrolidinones—stereochemical and lower side chain optimization; *Bioorg. Med Chem. Lett.*, 2004, 14, pp. 1655-1659, each of which is incorporated herein by reference in its entirety) were converted into 191 mg (56%) of (R,E)-methyl 4-(3-(2-(3-(4'-hydroxy-2'-methyl-[1,1'-biphenyl]-3-yl)-3-oxoprop-1-en-1-yl)-5-oxopyrrolidin-1-yl)propyl)benzoate.

Step 2. Methyl 4-(3-((2R)-2-((E)-3-hydroxy-3-(4'-hydroxy-2'-methyl-[1,1'-biphenyl]-3-yl)prop-1-en-1-yl)-5-oxopyrrolidin-1-yl)propyl)benzoate. In accordance with procedure of Example 1, step 3, (R,E)-methyl 4-(3-(2-(3-(4'-hydroxy-2'-methyl-[1,1'-biphenyl]-3-yl)-3-oxoprop-1-en-1-yl)-5-oxopyrrolidin-1-yl)propyl)benzoate (191 mg, 0.38 mmol) was converted into 41 mg (21%) of high $R^f$ methyl 4-(3-((2R)-2-((E)-3-hydroxy-3-(4'-hydroxy-2'-methyl-[1,1'-biphenyl]-3-yl)prop-1-en-1-yl)-5-oxopyrrolidin-1-yl)propyl)benzoate and 137 mg (71%) of low $R^f$ methyl 4-(3-((2R)-2-((E)-3-hydroxy-3-(4'-hydroxy-2'-methyl-[1,1'-biphenyl]-3-yl)prop-1-en-1-yl)-5-oxopyrrolidin-1-yl)propyl)benzoate.

Step 3. 4-(3-{2(R)-[(1E)-3-hydroxy-3-(4'-hydroxy-2'-methylbiphenyl-3-yl)prop-1-en-1-yl]-5-oxopyrrolidin-1-yl}propyl)benzoic acid (from high $R^f$ ester). In accordance with the procedure of Example 1, step 4, methyl 4-(3-((2R)-2-((E)-3-hydroxy-3-(4'-hydroxy-2'-methyl-[1,1'-biphenyl]-3-yl)prop-1-en-1-yl)-5-oxopyrrolidin-1-yl)propyl)benzoate (high Rf, 19 mg, 0.038 mmol) was converted into 11 mg (60%) of 4-(3-{2(R)-[(1E)-3-hydroxy-3-(4'-hydroxy-2'-methylbiphenyl-3-yl)prop-1-en-1-yl]-5-oxopyrrolidin-1-yl}propyl)benzoic acid.

Example 10

4-(3-{2(R)-[(1E)-3-hydroxy-3-(4'-hydroxy-2'-methylbiphenyl-3-yl)prop-1-en-1-yl]-5-oxopyrrolidin-1-yl}propyl)benzoic acid (from Low $R^f$ Ester)

In accordance with the procedure of Example 1, step 4, methyl 4-(3-((2R)-2-((E)-3-hydroxy-3-(4'-hydroxy-2'-methyl-[1,1'-biphenyl]-3-yl)prop-1-en-1-yl)-5-oxopyrrolidin-1-yl)propyl)benzoate (low Rf, 5 mg, 0.010 mmol) was converted into 3 mg (62%) of 4-(3-{2(R)-[(1E)-3-hydroxy-3-(4'-hydroxy-2'-methylbiphenyl-3-yl)prop-1-en-1-yl]-5-oxopyrrolidin-1-yl}propyl)benzoic acid.

Example 11

4-(3-{2(R)-[(1E)-3-(4'-fluoro-2'-methylbiphenyl-3-yl)-3-hydroxyprop-1-en-1-yl]-5-oxopyrrolidin-1-yl}propyl)benzoic acid (from High $R^f$ Ester)

Step 1. Methyl 4'-fluoro-2'-methyl-[1,1'-biphenyl]-3-carboxylate. In accordance with the procedure of Example 7, step 1, methyl 3-bromobenzoate (400 mg, 1.81 mmol) and (4-fluoro-2-methylphenyl)boronic acid (557 mg, 3.62 mmol) were converted into an inseparable mixture of methyl 4'-fluoro-2'-methyl-[1,1'-biphenyl]-3-carboxylate and methyl 3-bromobenzoate, which was used in the next step without further purification.

Step 2. Dimethyl (2-(4'-fluoro-2'-methyl-[1,1'-biphenyl]-3-yl)-2-oxoethyl)phosphonate. In accordance with the procedure of Example 1, step 1, impure methyl 2'-methyl-[1,1'-biphenyl]-3-carboxylate (~1.81 mmol) was converted into 255 mg (42% for 2 steps) of dimethyl (2-(4'-fluoro-2'-methyl-[1,1'-biphenyl]-3-yl)-2-oxoethyl)phosphonate.

Step 3. (R,E)-Methyl 4-(3-(2-(3-(4'-fluoro-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol), dimethyl (2-(4'-fluoro-2'-methyl-[1,1'-biphenyl]-3-yl)-2-oxoethyl)phosphonate (255 mg, 0.76 mmol) were converted into 84 mg (24%) of (R,E)-methyl 4-(3-(2-(3-(4'-fluoro-2'-methyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-fluoro-2'-methyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-fluoro-2'-methyl-[1,1'-biphenyl]-3-yl)-3-oxoprop-1-en-1-yl)-5-oxopyrrolidin-1-yl)propyl)benzoate (84 mg, 0.17 mmol) was converted into 41 mg (49%) of high $R^f$ methyl 4-(3-((2R)-2-((E)-3-(4'-fluoro-2'-methyl-[1,1'-biphenyl]-3-yl)-3-hydroxyprop-1-en-1-yl)-5-oxopyrrolidin-1-yl)propyl)benzoate and 17 mg (20%) of low $R^f$ methyl 4-(3-((2R)-2-((E)-3-(4'-fluoro-2'-methyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(4'-fluoro-2'-methylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-fluoro-2'-methyl-[1,1'-biphenyl]-3-yl)-3-hydroxyprop-1-en-1-yl)-5-oxopyrrolidin-1-yl)propyl)benzoate (high Rf, 41 mg, 0.082 mmol) was converted into 27 mg (68%) of 4-(3-{2(R)-[(1E)-3-(4'-fluoro-2'-methylbiphenyl-3-yl)-3-hydroxyprop-1-en-1-yl]-5-oxopyrrolidin-1-yl}propyl)benzoic acid after purification on silica gel using a Teledyne-Isco Combiflash machine (4 g column, $CH_2Cl_2$ to 15% methanol/$CH_2Cl_2$, 120 minute gradient).

Example 12

4-(3-{2(R)-[(1E)-3-(4'-fluoro-2'-methylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(4'-fluoro-2'-methyl-[1,1'-biphenyl]-3-yl)-3-hydroxyprop-1-en-1-yl)-5-oxopyrrolidin-1-yl)propyl)benzoate (low Rf, 17 mg, 0.034 mmol) was converted into 11 mg (67%) of 4-(3-{2(R)-[(1E)-3-(4'-fluoro-2'-methylbiphenyl-3-yl)-3-hydroxyprop-1-en-1-yl]-5-oxopyrrolidin-1-yl}propyl)benzoic acid after purification on silica gel using a Teledyne-Isco Combiflash machine (4 g column, $CH_2Cl_2$ to 15% methanol/$CH_2Cl_2$, 120 minute gradient).

Example 13

4-(3-{2(R)-[(1E)-3-(4'-chloro-2'-methylbiphenyl-3-yl)-3-hydroxyprop-1-en-1-yl]-5-oxopyrrolidin-1-yl}propyl)benzoic acid (from Low $R^f$ Ester)

Step 1. (R,E)-Methyl 4-(3-(2-(3-(4'-chloro-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-2'-methyl-[1,1'-biphenyl]-3-yl)-2-oxoethyl)phosphonate (268 mg, 0.76 mmol; prepared according to Colucci et al., WO 2007/014454, which is incorporated by reference herein in its entirety) were converted into 41 mg (11%) of (R,E)-methyl 4-(3-(2-(3-(4'-chloro-2'-methyl-[1,1'-biphenyl]-3-yl)-3-oxoprop-1-en-1-yl)-5-oxopyrrolidin-1-yl)propyl)benzoate.

Step 2. Methyl 4-(3-((2R)-2-((E)-3-(4'-chloro-2'-methyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-2'-methyl-[1,1'-biphenyl]-3-yl)-3-oxoprop-1-en-1-yl)-5-oxopyrrolidin-1-yl)propyl)benzoate (41 mg, 0.079 mmol) was converted into 14 mg (34%) of high $R^f$ methyl 4-(3-((2R)-2-((E)-3-(4'-chloro-2'-methyl-[1,1'-biphenyl]-3-yl)-3-hydroxyprop-1-en-1-yl)-5-oxopyrrolidin-1-yl)propyl)benzoate and 7 mg (17%) of low $R^f$ methyl 4-(3-((2R)-2-((E)-3-(4'-chloro-2'-methyl-[1,1'-biphenyl]-3-yl)-3-hydroxyprop-1-en-1-yl)-5-oxopyrrolidin-1-yl)propyl)benzoate.

Step 3. 4-(3-{2(R)-[(1E)-3-(4'-chloro-2'-methylbiphenyl-3-yl)-3-hydroxyprop-1-en-1-yl]-5-oxopyrrolidin-1-yl}propyl)benzoic acid (from low $R^f$ ester). In accordance with the procedure of Example 1, step 4, methyl 4-(3-((2R)-2-((E)-3-(4'-chloro-2'-methyl-[1,1'-biphenyl]-3-yl)-3-hydroxyprop-1-en-1-yl)-5-oxopyrrolidin-1-yl)propyl)benzoate (low Rf, 7 mg, 0.014 mmol) was converted into 3 mg (44%) of 4-(3-{2(R)-[(1E)-3-(4'-chloro-2'-methylbiphenyl-3-yl)-3-hydroxyprop-1-en-1-yl]-5-oxopyrrolidin-1-yl}propyl)benzoic acid.

Example 14

4-(3-{2(R)-[(1E)-3-(4'-chloro-2'-ethylbiphenyl-3-yl)-3-hydroxyprop-1-en-1-yl]-5-oxopyrrolidin-1-yl}propyl)benzoic acid (from High $R^f$ Ester)

Step 1. Methyl 4'-chloro-2'-ethyl-[1,1'-biphenyl]-3-carboxylate. In accordance with the procedure of Example 7, step 1, (3-(methoxycarbonyl)phenyl)boronic acid (400 mg, 2.22 mmol) and 1-bromo-4-chloro-2-ethylbenzene (976 mg, 4.45 mmol) were converted into 500 mg (~80%) of impure methyl 4'-chloro-2'-ethyl-[1,1'-biphenyl]-3-carboxylate, which was used in the next step without further purification.

Step 2. Dimethyl (2-(4'-chloro-2'-ethyl-[1,1'-biphenyl]-3-yl)-2-oxoethyl)phosphonate. In accordance with the procedure of Example 1, step 1, impure methyl 4'-chloro-2'-ethyl-[1,1'-biphenyl]-3-carboxylate (~1.8 mmol) was converted into 279 mg (34% for 2 steps) of dimethyl (2-(4'-chloro-2'-ethyl-[1,1'-biphenyl]-3-yl)-2-oxoethyl)phosphonate.

Step 3. (R,E)-Methyl 4-(3-(2-(3-(4'-chloro-2'-ethyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-2'-ethyl-[1,1'-biphenyl]-3-yl)-2-oxoethyl)phosphonate (279 mg, 0.76 mmol) were converted into 60 mg (11%) of (R,E)-methyl 4-(3-(2-(3-(4'-chloro-2'-ethyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-chloro-2'-ethyl-[1,1'-biphenyl]-3-yl)-3-hydroxyprop-1-en-1-yl)-5-oxopyrrolidin-1-yl)propyl)benzoate. In accordance with the procedure of Example 1, step 3 (R,E)-methyl 4-(3-(2-(3-(4'-chloro-2'-ethyl-[1,1'-biphenyl]-3-yl)-3-oxoprop-1-en-1-yl)-5-oxopyrrolidin-1-yl)propyl)benzoate (60 mg, 0.11 mmol) was converted into 19 mg (32%) of high $R^f$ methyl 4-(3-((2R)-2-((E)-3-(4'-chloro-2'-ethyl-[1,1'-biphenyl]-3-yl)-3-hydroxyprop-1-en-1-yl)-5-oxopyrrolidin-1-yl)propyl)benzoate and 11 mg (18%) of low $R^f$ methyl 4-(3-((2R)-2-((E)-3-(4'-chloro-2'-ethyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(4'-chloro-2'-ethylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-chloro-2'-ethyl-[1,1'-biphenyl]-3-yl)-3-hydroxyprop-1-en-1-yl)-5-oxopyrrolidin-1-yl)propyl)benzoate (high Rf, 19 mg, 0.036 mmol) was converted into 11 mg (59%) of 4-(3-{2(R)-[(1E)-3-(4'-chloro-2'-ethylbiphenyl-3-yl)-3-hydroxyprop-1-en-1-yl]-5-oxopyrrolidin-1-yl}propyl)benzoic acid after purification on silica gel using a Teledyne-Isco Combiflash machine (4 g column, CH$_2$Cl$_2$ to 15% methanol/CH$_2$Cl$_2$, 120 minute gradient). $^1$H NMR (600 MHz, CDCl$_3$) δ 7.84 (d, J=8.2 Hz, 2H), 7.04-7.35 (m, 8H), 6.93-7.04 (m, 1H), 5.80 (dd, J=15.2, 5.6 Hz, 1H), 5.50 (dd, J=15.7, 8.1 Hz, 1H), 5.13 (d, J=5.9 Hz, 1H), 3.93-4.04 (m, 1H), 3.33-3.49 (m, 1H), 2.75-2.96 (m, 1H), 2.38-2.53 (m, 4H), 2.04-2.34 (m, 3H), 1.61-1.76 (m, 4H), 0.97 (t, J=7.6 Hz, 3H).

Example 15

4-(3-{2(R)-[(1E)-3-(4'-chloro-2'-ethylbiphenyl-3-yl)-3-hydroxyprop-1-en-1-yl]-5-oxopyrrolidin-1-yl}propyl)benzoic acid (from Low R$^f$ Ester)

In accordance with the procedure of Example 7, step 5, methyl 4-(3-((2R)-2-((E)-3-(4'-chloro-2'-ethyl-[1,1'-biphenyl]-3-yl)-3-hydroxyprop-1-en-1-yl)-5-oxopyrrolidin-1-yl)propyl)benzoate (low Rf, 11 mg, 0.021 mmol) was converted into 7 mg (65%) of 4-(3-{2(R)-[(1E)-3-(4'-chloro-2'-ethylbiphenyl-3-yl)-3-hydroxyprop-1-en-1-yl]-5-oxopyrrolidin-1-yl}propyl)benzoic acid after purification on silica gel using a Teledyne-Isco Combiflash machine (4 g column, CH$_2$Cl$_2$ to 15% methanol/CH$_2$Cl$_2$, 120 minute gradient). $^1$H NMR (600 MHz, CDCl$_3$) δ 7.84 (d, J=8.2 Hz, 2H), 6.94-7.18 (m, 8H), 6.76-6.87 (m, 1H), 5.76 (dd, J=15.4, 6.0 Hz, 1H), 5.47-5.58 (m, 1H), 5.11 (d, J=5.6 Hz, 1H), 3.96-4.03 (m, 1H), 3.41 (m, 1H), 2.79-2.91 (m, 1H), 2.48 (t, J=7.3 Hz, 3H), 2.19-2.34 (m, 4H), 1.68 (d, J=5.6 Hz, 4H), 0.74-0.84 (m, 3H).

Example 16

4-[3-(2(R)-{(1E)-3-[4'-chloro-2'-(trifluoromethyl)biphenyl-3-yl]-3-hydroxyprop-1-en-1-yl}-5-oxopyrrolidin-1-yl)propyl]benzoic acid (from High R$^f$ Ester)

Step 1. Methyl 4'-chloro-2'-(trifluoromethyl)-[1,1'-biphenyl]-3-carboxylate. In accordance with the procedure of Example 7, step 1, methyl 3-bromobenzoate (400 mg, 1.81 mmol) and (4-chloro-2-(trifluoromethyl)phenyl)boronic acid (812 mg, 3.62 mmol) were converted into 500 mg an inseparable mixture of methyl 4'-chloro-2'-(trifluoromethyl)-[1,1'-biphenyl]-3-carboxylate and methyl 3-bromobenzoate, which was used in the next step without further purification.

Step 2. Dimethyl (2-(4'-chloro-2'-(trifluoromethyl)-[1,1'-biphenyl]-3-yl)-2-oxoethyl)phosphonate. In accordance with the procedure of Example 1, step 1, impure methyl 4'-chloro-2'-(trifluoromethyl)-[1,1'-biphenyl]-3-carboxylate (~1.59 mmol) was converted into 309 mg (42% for 2 steps) of dimethyl (2-(4'-chloro-2'-(trifluoromethyl)-[1,1'-biphenyl]-3-yl)-2-oxoethyl)phosphonate.

Step 3. (R,E)-Methyl 4-(3-(2-(3-(4'-chloro-2'-(trifluoromethyl)-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-2'-(trifluoromethyl)-[1,1'-biphenyl]-3-yl)-2-oxoethyl)phosphonate (309 mg, 0.76 mmol) were converted into 84 mg (21%) of (R,E)-methyl 4-(3-(2-(3-(4'-chloro-2'-(trifluoromethyl)-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-chloro-2'-(trifluoromethyl)-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-2'-(trifluoromethyl)-[1,1'-biphenyl]-3-yl)-3-oxoprop-1-en-1-yl)-5-oxopyrrolidin-1-yl)propyl)benzoate (84 mg, 0.16 mmol) was converted into 44 mg (49%) of high R$^f$ methyl 4-(3-((2R)-2-((E)-3-(4'-chloro-2'-(trifluoromethyl)-[1,1'-biphenyl]-3-yl)-3-hydroxyprop-1-en-1-yl)-5-oxopyrrolidin-1-yl)propyl)benzoate and 22 mg (24%) of low R$^f$ methyl 4-(3-((2R)-2-((E)-3-(4'-chloro-2'-(trifluoromethyl)-[1,1'-biphenyl]-3-yl)-3-hydroxyprop-1-en-1-yl)-5-oxopyrrolidin-1-yl)propyl)benzoate.

Step 5. 4-[3-(2(R)-{(1E)-3-[4'-chloro-2'-(trifluoromethyl)biphenyl-3-yl]-3-hydroxyprop-1-en-1-yl}-5-oxopyrrolidin-1-yl)propyl]benzoic acid (from high R$^f$ ester). In accordance with the procedure of Example 7, step 5, methyl 4-(3-((2R)-2-((E)-3-(4'-chloro-2'-(trifluoromethyl)-[1,1'-biphenyl]-3-yl)-3-hydroxyprop-1-en-1-yl)-5-oxopyrrolidin-1-yl)propyl)benzoate (high Rf, 22 mg, 0.038 mmol) was converted into 15 mg (70%) of 4-[3-(2(R)-{(1E)-3-[4'-chloro-2'-(trifluoromethyl)biphenyl-3-yl]-3-hydroxyprop-1-en-1-yl}-5-oxopyrrolidin-1-yl)propyl]benzoic acid after purification on silica gel using a Teledyne-Isco Combiflash machine (4 g column, CH$_2$Cl$_2$→15% methanol/CH$_2$Cl$_2$, 120 minute gradient).

Example 17

4-[3-(2(R)-{(1E)-3-[4'-chloro-2'-(trifluoromethyl)biphenyl-3-yl]-3-hydroxyprop-1-en-1-yl}-5-oxopyrrolidin-1-yl)propyl]benzoic acid (from Low R$^f$ Ester)

In accordance with the procedure of Example 7, step 5, methyl 4-(3-((2R)-2-((E)-3-(4'-chloro-2'-(trifluoromethyl)-[1,1'-biphenyl]-3-yl)-3-hydroxyprop-1-en-1-yl)-5-oxopyrrolidin-1-yl)propyl)benzoate (low Rf, 11 mg, 0.019 mmol) was converted into 7 mg (65%) of 4-[3-(2(R)-{(1E)-3-[4'-chloro-2'-(trifluoromethyl)biphenyl-3-yl]-3-hydroxyprop-1-en-1-yl}-5-oxopyrrolidin-1-yl)propyl]benzoic acid after purification on silica gel using a Teledyne-Isco Combiflash machine (4 g column, CH$_2$Cl$_2$ to 15% methanol/CH$_2$Cl$_2$, 120 minute gradient).

Example 18

4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid (from High R$^f$ Ester)

Step 1. ((2-Bromo-5-chlorobenzyl)oxy)(tert-butyl)dimethylsilane. Triethylamine (0.30 mL, 2.15 mmol), DMAP (97 mg, 0.79 mmol) and tert-butyldimethylsilyl chloride (TBSCl; 698 mg, 4.63 mmol) were added to a solution of (2-bromo-5-chlorophenyl)methanol (500 mg, 2.26 mmol) in CH$_2$Cl$_2$ (11.3 mL) at room temperature. After stirring overnight, the reaction mixture was partitioned between saturated aqueous sodium bicarbonate (50 mL) and CH$_2$Cl$_2$ (200 mL). The phases were separated and the aqueous phase was extracted with CH$_2$Cl$_2$ (2×100 mL). The combined organic phase was washed with brine, dried (MgSO$_4$), filtered and concentrated in vacuo. The resulting crude residue was purified on silica gel using a Teledyne-Isco Combiflash machine (40 g column, hexanes to 100% EtOAc, gradient) to afford 561 mg (74%) of ((2-bromo-5-chlorobenzyl)oxy)(tert-butyl)dimethylsilane Step 2. Methyl 2'-(((tert-butyldimethylsilyl)oxy)methyl)-4'-chloro-[1,1'-biphenyl]-3-carboxylate. In accordance with the procedure of Example 7, step 1, (3-(methoxycarbonyl)

phenyl)boronic acid (400 mg, 2.22 mmol) and ((2-bromo-5-chlorobenzyl)oxy)(tert-butyl)dimethylsilane (895 mg, 2.67 mmol) were converted into 500 mg (~55%) of impure methyl 2'-(((tert-butyldimethylsilyl)oxy)methyl)-4'-chloro-[1,1'-biphenyl]-3-carboxylate, which was used in the next step without further purification.

Step 3. Dimethyl (2-(2'-(((tert-butyldimethylsilyl)oxy)methyl)-4'-chloro-[1,1'-biphenyl]-3-yl)-2-oxoethyl)phosphonate. In accordance with the procedure of Example 1, step 1, impure methyl 2'-(((tert-butyldimethylsilyl)oxy)methyl)-4'-chloro-[1,1'-biphenyl]-3-carboxylate (~1.28 mmol) was converted into 367 mg (34% for 2 steps) of dimethyl (2-(2'-(((tert-butyldimethylsilyl)oxy)methyl)-4'-chloro-[1,1'-biphenyl]-3-yl)-2-oxoethyl)phosphonate.

Step 4. (R,E)-Methyl 4-(3-(2-(3-(2'-(((tert-butyldimethylsilyl)oxy)methyl)-4'-chloro-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(2'-(((tert-butyldimethylsilyl)oxy)methyl)-4'-chloro-[1,1'-biphenyl]-3-yl)-2-oxoethyl)phosphonate (367 mg, 0.76 mmol) were converted into 114 mg (26%) of (R,E)-methyl 4-(3-(2-(3-(2'-(((tert-butyldimethylsilyl)oxy)methyl)-4'-chloro-[1,1'-biphenyl]-3-yl)-3-oxoprop-1-en-1-yl)-5-oxopyrrolidin-1-yl)propyl)benzoate.

Step 5. Methyl 4-(3-((2R)-2-((E)-3-(2'-(((tert-butyldimethylsilyl)oxy)methyl)-4'-chloro-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(2'-(((tert-butyldimethylsilyl)oxy)methyl)-4'-chloro-[1,1'-biphenyl]-3-yl)-3-oxoprop-1-en-1-yl)-5-oxopyrrolidin-1-yl)propyl)benzoate (114 mg, 0.18 mmol) was converted into 60 mg (52%) of high $R^f$ methyl 4-(3-((2R)-2-((E)-3-(2'-(((tert-butyldimethylsilyl)oxy)methyl)-4'-chloro-[1,1'-biphenyl]-3-yl)-3-hydroxyprop-1-en-1-yl)-5-oxopyrrolidin-1-yl)propyl)benzoate and 40 mg (35%) of low $R^f$ methyl 4-(3-((2R)-2-((E)-3-(2'-(((tert-butyldimethylsilyl)oxy)methyl)-4'-chloro-[1,1'-biphenyl]-3-yl)-3-hydroxyprop-1-en-1-yl)-5-oxopyrrolidin-1-yl)propyl)benzoate.

Step 6. Methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate (from high $R^f$ ester). A solution of tetrabutylammonium fluoride (93 microliters of a 1.0 M solution in THF, 0.093 mmol) was added to a solution of methyl 4-(3-((2R)-2-((E)-3-(2'-(((tert-butyldimethylsilyl)oxy)methyl)-4'-chloro-[1,1'-biphenyl]-3-yl)-3-hydroxyprop-1-en-1-yl)-5-oxopyrrolidin-1-yl)propyl)benzoate (high $R^f$ ester, 60 mg, 0.093 mmol) in THF (3 mL) at 0° C. The solution was stirred for 5 hours and allowed to warm to room temperature. The reaction was partitioned between EtOAc (20 mL) and saturated aqueous sodium bicarbonate (10 mL). The phases were separated and the aqueous phase was extracted with EtOAc (2×50 mL). The combined organic phase was washed with brine, dried (MgSO$_4$), filtered and concentrated in vacuo. The resulting crude residue was purified on silica gel using a Teledyne-Isco Combiflash machine (4 g column, hexanes to 100% EtOAc, gradient) to afford 28 mg (57%) of methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate.

Step 7. 4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid (from high $R^f$ ester). In accordance with the procedure of Example 7, step 5, methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate (from high Rf ester, 28 mg, 0.052 mmol) was converted into 19 mg (70%) of 4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid.

Example 19

4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid (from Low $R^f$ Ester)

Step 1. Methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate (from low $R^f$ ester). In accordance with the procedure of Example 18, step 6, methyl 4-(3-((2R)-2-((E)-3-(2'-(((tert-butyldimethylsilyl)oxy)methyl)-4'-chloro-[1,1'-biphenyl]-3-yl)-3-hydroxyprop-1-en-1-yl)-5-oxopyrrolidin-1-yl)propyl)benzoate (low $R^f$ ester, 40 mg, 0.062 mmol) was converted into 17 mg (52%) of methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate.

Step 2. 4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid (from low $R^f$ ester). In accordance with the procedure of Example 7, step 5, methyl 4-(3-((2R)-2-((E)-3-(4'-chloro-2'-(hydroxymethyl)-[1,1'-biphenyl]-3-yl)-3-hydroxyprop-1-en-1-yl)-5-oxopyrrolidin-1-yl)propyl)benzoate (from low Rf ester, 17 mg, 0.032 mmol) was converted into 8 mg (48%) of 4-[3-(2(R)-{(1E)-3-[4'-chloro-2'-(hydroxymethyl)biphenyl-3-yl]-3-hydroxyprop-1-en-1-yl}-5-oxopyrrolidin-1-yl)propyl]benzoic acid.

Example 20

4-(3-{2(R)-[(1E)-3-(4'-chloro-2',6'-dimethylbiphenyl-3-yl)-3-hydroxyprop-1-en-1-yl]-5-oxopyrrolidin-1-yl}propyl)benzoic acid (from High $R^f$ Ester)

Step 1. Methyl 4'-chloro-2',6'-dimethyl-[1,1'-biphenyl]-3-carboxylate. In accordance with the procedure of Example 7, step 1, methyl 3-bromobenzoate (400 mg, 1.81 mmol) and (4-chloro-2,6-dimethylphenyl)boronic acid (667 mg, 3.62 mmol) were converted into 500 mg impure methyl 4'-chloro-2',6'-dimethyl-[1,1'-biphenyl]-3-carboxylate, which was used in the next step without further purification.

Step 2. Dimethyl (2-(4'-chloro-2',6'-dimethyl-[1,1'-biphenyl]-3-yl)-2-oxoethyl)phosphonate. In accordance with the procedure of Example 1, step 1, impure methyl 4'-chloro-2',6'-dimethyl-[1,1'-biphenyl]-3-carboxylate (~1.81 mmol) was converted into 278 mg (42% for 2 steps) of dimethyl (2-(4'-chloro-2',6'-dimethyl-[1,1'-biphenyl]-3-yl)-2-oxoethyl)phosphonate.

Step 3. (R,E)-Methyl 4-(3-(2-(3-(4'-chloro-2',6'-dimethyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-2',6'-dimethyl-[1,1'-biphenyl]-3-yl)-2-oxoethyl)phosphonate (278 mg, 0.76 mmol) were converted into 200 mg (55%) of (R,E)-methyl 4-(3-(2-(3-(4'-chloro-2',6'-dimethyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-chloro-2',6'-dimethyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-2',6'-dimethyl-[1,1'-biphenyl]-3-yl)-3-oxoprop-1-en-1-yl)-5-oxopyrrolidin-1-yl)propyl)benzoate (200 mg, 0.37 mmol) was converted into 17 mg (8%) of high $R^f$ methyl 4-(3-((2R)-2-((E)-3-(4'-chloro-2',6'-dimethyl-[1,1'-biphenyl]-3-yl)-3-hydroxyprop-1-en-1-yl)-5-oxopyrrolidin-1-yl)propyl)benzoate and 9 mg (4%) of low $R^f$ methyl 4-(3-((2R)-2-((E)-3-(4'-chloro-2',6'-dimethyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(4'-chloro-2',6'-dimethylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-chloro-2',6'-dimethyl-[1,1'-biphenyl]-3-yl)-3-hydroxyprop-1-en-1-yl)-5-oxopyrrolidin-1-yl)propyl)benzoate (high Rf, 17 mg, 0.032 mmol) was converted into 9 mg (54%) of 4-(3-{2(R)-[(1E)-3-(4'-chloro-2',6'-dimethylbiphenyl-3-yl)-3-hydroxyprop-1-en-1-yl]-5-oxopyrrolidin-1-yl}propyl)benzoic acid.

Example 21

4-(3-{2(R)-[(1E)-3-(4'-chloro-2',6'-dimethylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(4'-chloro-2',6'-dimethyl-[1,1'-biphenyl]-3-yl)-3-hydroxyprop-1-en-1-yl)-5-oxopyrrolidin-1-yl)propyl)benzoate (low Rf, 9 mg, 0.017 mmol) was converted into 3 mg (34%) of 4-(3-{2(R)-[(1E)-3-(4'-chloro-2',6'-dimethylbiphenyl-3-yl)-3-hydroxyprop-1-en-1-yl]-5-oxopyrrolidin-1-yl}propyl)benzoic acid.

Example 22

4-(3-{2(R)-[(1E)-3-(3',4'-dichloro-2'-methylbiphenyl-3-yl)-3-hydroxyprop-1-en-1-yl]-5-oxopyrrolidin-1-yl}propyl)benzoic acid (from High $R^f$ Ester)

Step 1. Methyl 3',4'-dichloro-2'-methyl-[1,1'-biphenyl]-3-carboxylate. In accordance with the procedure of Example 7, step 1, methyl 3-bromobenzoate (400 mg, 1.81 mmol) (812 mg, 3.62 mmol) were converted into 500 mg an inseparable mixture of methyl 3',4'-dichloro-2'-methyl-[1,1'-biphenyl]-3-carboxylate and methyl 3-bromobenzoate, which was used in the next step without further purification.

Step 2. Dimethyl (2-(3',4'-dichloro-2'-methyl-[1,1'-biphenyl]-3-yl)-2-oxoethyl)phosphonate. In accordance with the procedure of Example 1, step 1, impure methyl 3',4'-dichloro-2'-methyl-[1,1'-biphenyl]-3-carboxylate (~1.69 mmol) was converted into 294 mg (42% for 2 steps) of dimethyl (2-(3',4'-dichloro-2'-methyl-[1,1'-biphenyl]-3-yl)-2-oxoethyl)phosphonate.

Step 3. (R,E)-Methyl 4-(3-(2-(3-(3',4'-dichloro-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(3',4'-dichloro-2'-methyl-[1,1'-biphenyl]-3-yl)-2-oxoethyl)phosphonate (294 mg, 0.76 mmol) were converted into 200 mg (53%) of (R,E)-methyl 4-(3-(2-(3-(3',4'-dichloro-2'-methyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(3',4'-dichloro-2'-methyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(3',4'-dichloro-2'-methyl-[1,1'-biphenyl]-3-yl)-3-oxoprop-1-en-1-yl)-5-oxopyrrolidin-1-yl)propyl)benzoate (200 mg, 0.36 mmol) was converted into 42 mg (21%) of high $R^f$ methyl 4-(3-((2R)-2-((E)-3-(3',4'-dichloro-2'-methyl-[1,1'-biphenyl]-3-yl)-3-hydroxyprop-1-en-1-yl)-5-oxopyrrolidin-1-yl)propyl)benzoate and 42 mg (21%) of low $R^f$ methyl 4-(3-((2R)-2-((E)-3-(3',4'-dichloro-2'-methyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(3',4'-dichloro-2'-methylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(3',4'-dichloro-2'-methyl-[1,1'-biphenyl]-3-yl)-3-hydroxyprop-1-en-1-yl)-5-oxopyrrolidin-1-yl)propyl)benzoate (high Rf, 21 mg, 0.038 mmol) was converted into 16 mg (78%) of 4-(3-{2(R)-[(1E)-3-(3',4'-dichloro-2'-methylbiphenyl-3-yl)-3-hydroxyprop-1-en-1-yl]-5-oxopyrrolidin-1-yl}propyl)benzoic acid.

Example 23

4-(3-{2(R)-[(1E)-3-(3',4'-dichloro-2'-methylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(3',4'-dichloro-2'-methyl-[1,1'-biphenyl]-3-yl)-3-hydroxyprop-1-en-1-yl)-5-oxopyrrolidin-1-yl)propyl)benzoate (low Rf, 21 mg, 0.038 mmol) was converted into 12 mg (59%) of 4-(3-{2(R)-[(1E)-3-(3',4'-dichloro-2'-methylbiphenyl-3-yl)-3-hydroxyprop-1-en-1-yl]-5-oxopyrrolidin-1-yl}propyl)benzoic acid.

Example 24

4-(3-{2(R)-[(1E)-3-(4'-chloro-2'-propylbiphenyl-3-yl)-3-hydroxyprop-1-en-1-yl]-5-oxopyrrolidin-1-yl}propyl)benzoic acid (from High $R^f$ Ester)

Step 1. 2-Bromo-5-chlorobenzaldehyde. Dimethyl sulfoxide (472 μL, 6.10 mmol) was added to a −78° C. solution of oxalyl chloride (1.47 mL of a 2.0 M solution in $CH_2Cl_2$, 2.94 mmol) and $CH_2Cl_2$ (4 mL). After 30 min at −78° C., a solution of (2-bromo-5-chlorophenyl)methanol (500 mg, 2.26 mmol) in $CH_2Cl_2$ (2 mL) was added. After 5 min, triethylamine (2.52 mL, 18.0 mmol) was added and the mixture was allowed to warm to 0° C. After 1 hour, the mixture was allowed to warm to room temperature. After 3 hours, the reaction was quenched with saturated aqueous $NaHCO_3$ (60 mL) and extracted with $CH_2Cl_2$ (3×50 mL). The combined extracts were dried ($Na_2SO_4$), filtered and concentrated in vacuo to afford 400 mg of crude 2-bromo-5-chlorobenzaldehyde that was used in the next step without further purification.

Step 2. 1-Bromo-4-chloro-2-(prop-1-en-1-yl)benzene. A solution of crude 2-bromo-5-chlorobenzaldehyde (~400 mg, ~1.82 mmol) in THF (5 mL) was added to a mixture of ethyl triphenylphosphonium bromide (dried overnight under vacuum, 744 mg, 2.00 mmol) in THF (25 mL) at room temperature. Potassium tert-butoxide (750 mg, 6.74 mmol)

was added and the reaction mixture was stirred overnight. The mixture was quenched with saturated aqueous NH4Cl and extracted with EtOAc (2×50 mL). The combined extracts were washed with brine (10 mL), dried ($Na_2SO_4$), filtered and concentrated in vacuo. The resulting crude residue was purified on silica gel using a Teledyne-Isco Combiflash machine (80 g gold column, hexanes to 100% EtOAc, gradient), to afford 170 mg (32% for 2 steps) of 1-bromo-4-chloro-2-(prop-1-en-1-yl)benzene as a mixture of alkene isomers.

Step 3. Methyl 4'-chloro-2'-(prop-1-en-1-yl)-[1,1'-biphenyl]-3-carboxylate. A Schlenk tube was charged with palladium acetate (4.1 mg, 0.018 mmol), dicyclohexyl(2',6'-dimethoxy-[1,1'-biphenyl]-2-yl)phosphine (SPhos, 15 mg, 0.036 mmol), (3-(methoxycarbonyl)phenyl)boronic acid (110 mg, 0.61 mmol) and 1-bromo-4-chloro-2-(prop-1-en-1-yl)benzene (110 mg, 0.61 mmol). Potassium phosphate (freshly ground under nitrogen using a mortar and pestle, 169 mg, 0.79 mmol) was added to the tube. Toluene (2.0 mL) was added and the reaction mixture was purged with nitrogen. The tube was sealed under nitrogen and heated at 100° C. overnight. The reaction mixture was then cooled and filtered through celite, washing with excess toluene. The filtrate was concentrated in vacuo and the resulting crude residue was purified on silica gel using a Teledyne-Isco Combiflash machine (12 g column, hexanes to 100% EtOAc, gradient) to afford 141 mg (80%) of methyl 4'-chloro-2'-(prop-1-en-1-yl)-[1,1'-biphenyl]-3-carboxylate.

Step 4. Methyl 4'-chloro-2'-propyl-[1,1'-biphenyl]-3-carboxylate. Palladium on carbon (10 wt. %, 10 mg, 0.1 mmol) was added to a solution of methyl 4'-chloro-2'-(prop-1-en-1-yl)-[1,1'-biphenyl]-3-carboxylate (141 mg, 0.49 mmol) in EtOAc (3.8 mL). A hydrogen atmosphere was established by evacuating and refilling with hydrogen (3×) and then the reaction mixture was stirred under a balloon of nitrogen overnight. The mixture was then diluted with EtOAc and filtered through celite. The filtrate was concentrated in vacuo to afford 141 mg (99%) of methyl 4'-chloro-2'-propyl-[1,1'-biphenyl]-3-carboxylate.

Step 5. Dimethyl (2-(4'-chloro-2'-propyl-[1,1'-biphenyl]-3-yl)-2-oxoethyl)phosphonate. In accordance with the procedure of Example 1, step 1, methyl 4'-chloro-2'-propyl-[1,1'-biphenyl]-3-carboxylate (141 mg, 0.49 mmol) was converted into 144 mg (77%) of dimethyl (2-(4'-chloro-2'-propyl-[1,1'-biphenyl]-3-yl)-2-oxoethyl)phosphonate.

Step 6. (R,E)-Methyl 4-(3-(2-(3-(4'-chloro-2'-propyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (100 mg, 0.35 mmol) and dimethyl (2-(4'-chloro-2'-propyl-[1,1'-biphenyl]-3-yl)-2-oxoethyl)phosphonate (144 mg, 0.38 mmol) were converted into 60 mg (32%) of (R,E)-methyl 4-(3-(2-(3-(4'-chloro-2'-propyl-[1,1'-biphenyl]-3-yl)-3-oxoprop-1-en-1-yl)-5-oxopyrrolidin-1-yl)propyl)benzoate.

Step 7. Methyl 4-(3-((2R)-2-((E)-3-(4'-chloro-2'-propyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-2'-propyl-[1,1'-biphenyl]-3-yl)-3-oxoprop-1-en-1-yl)-5-oxopyrrolidin-1-yl)propyl)benzoate (60 mg, 0.11 mmol) was converted into 14 mg (23%) of high $R^f$ methyl 4-(3-((2R)-2-((E)-3-(4'-chloro-2'-propyl-[1,1'-biphenyl]-3-yl)-3-hydroxyprop-1-en-1-yl)-5-oxopyrrolidin-1-yl)propyl)benzoate and 7 mg (12%) of low $R^f$ methyl 4-(3-((2R)-2-((E)-3-(4'-chloro-2'-propyl-[1,1'-biphenyl]-3-yl)-3-hydroxyprop-1-en-1-yl)-5-oxopyrrolidin-1-yl)propyl)benzoate.

Step 8. 4-(3-{2(R)-[(1E)-3-(4'-chloro-2'-propylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-chloro-2'-propyl-[1,1'-biphenyl]-3-yl)-3-hydroxyprop-1-en-1-yl)-5-oxopyrrolidin-1-yl)propyl)benzoate (high Rf, 14 mg, 0.026 mmol) was converted into 9 mg (66%) of 4-(3-{2(R)-[(1E)-3-(4'-chloro-2'-propylbiphenyl-3-yl)-3-hydroxyprop-1-en-1-yl]-5-oxopyrrolidin-1-yl}propyl)benzoic acid.

Example 25

4-(3-{2(R)-[(1E)-3-(4'-chloro-2'-propylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(4'-chloro-2'-propyl-[1,1'-biphenyl]-3-yl)-3-hydroxyprop-1-en-1-yl)-5-oxopyrrolidin-1-yl)propyl)benzoate (low Rf, 7 mg, 0.013 mmol) was converted into 3 mg (44%) of 4-(3-{2(R)-[(1E)-3-(4'-chloro-2'-propylbiphenyl-3-yl)-3-hydroxyprop-1-en-1-yl]-5-oxopyrrolidin-1-yl}propyl)benzoic acid.

Example 26

4-(3-{2(R)-[(1E)-3-(2'-tert-butyl-4'-chlorobiphenyl-3-yl)-3-hydroxyprop-1-en-1-yl]-5-oxopyrrolidin-1-yl}propyl)benzoic acid (from High $R^f$ Ester)

Step 1. 2-(tert-Butyl)-4-chlorophenyl trifluoromethanesulfonate. N, N-Diisopropylethylamine (1.56 mL, 8.94 mmoL) and trifluoromethanesulfonic anhydride (1.68 mL, 4.17 mmol) were added sequentially to a −78° C. solution of 2-(tert-butyl)-4-chlorophenol (550 mg, 2.98 mmol) in $CH_2Cl_2$ (40 mL). After 1 hour at −78° C., the reaction mixture was poured into saturated aqueous $NH_4Cl$ (30 mL). The mixture was extracted with $CH_2Cl_2$ (3×50 mL). The combined organic phase was washed with brine (20 mL), dried ($MgSO_4$), filtered and concentrated in vacuo. The resulting crude residue was purified on silica gel using a Teledyne-Isco Combiflash machine (12 g column, hexanes to 100% EtOAc, gradient), to afford 943 mg (quant.) of 2-(tert-butyl)-4-chlorophenyl trifluoromethanesulfonate.

Step 2. Methyl 2'-(tert-butyl)-4'-chloro-[1,1'-biphenyl]-3-carboxylate. A Schlenk tube was charged with palladium acetate (4.1 mg, 0.018 mmol), dicyclohexyl(2',6'-dimethoxy-[1,1'-biphenyl]-2-yl)phosphine (SPhos, 15 mg, 0.036 mmol), (3-(methoxycarbonyl)phenyl)boronic acid (110 mg, 0.61 mmol) and 2-(tert-butyl)-4-chlorophenyl trifluoromethanesulfonate (204 mg, 0.64 mmol). Potassium phosphate (freshly ground under nitrogen using a mortar and pestle, 169 mg, 0.79 mmol) was added to the tube. Toluene (2.0 mL) was added and the reaction mixture was purged with nitrogen. The tube was sealed under nitrogen and heated at 100° C. overnight. The reaction mixture was then cooled and filtered through celite, washing with excess toluene. The filtrate was concentrated in vacuo and the resulting crude residue was purified on silica gel using a Teledyne-Isco Combiflash machine (12 g column, hexanes to 100% EtOAc, gradient) to afford 110 mg (59%) of methyl 2'-(tert-butyl)-4'-chloro-[1,1'-biphenyl]-3-carboxylate.

Step 3. Dimethyl (2-(2'-(tert-butyl)-4'-chloro-[1,1'-biphenyl]-3-yl)-2-oxoethyl)phosphonate. In accordance with the procedure of Example 1, step 1, methyl 2'-(tert-butyl)-4'-chloro-[1,1'-biphenyl]-3-carboxylate (~110 mg, 0.36 mmol) was converted into 139 mg (97%) of dimethyl (2-(2'-(tert-butyl)-4'-chloro-[1,1'-biphenyl]-3-yl)-2-oxoethyl)phosphonate.

Step 4. (R,E)-Methyl 4-(3-(2-(3-(2'-(tert-butyl)-4'-chloro-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (100 mg, 0.35 mmol) and dimethyl (2-(2'-(tert-butyl)-4'-chloro-[1,1'-biphenyl]-3-yl)-2-oxoethyl)phosphonate (139 mg, 0.35 mmol) were converted into 60 mg (16%) of (R,E)-methyl 4-(3-(2-(3-(2'-(tert-butyl)-4'-chloro-[1,1'-biphenyl]-3-yl)-3-oxoprop-1-en-1-yl)-5-oxopyrrolidin-1-yl)propyl)benzoate.

Step 5. Methyl 4-(3-((2R)-2-((E)-3-(2'-(tert-butyl)-4'-chloro-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(2'-(tert-butyl)-4'-chloro-[1,1'-biphenyl]-3-yl)-3-oxoprop-1-en-1-yl)-5-oxopyrrolidin-1-yl)propyl)benzoate (60 mg, 0.11 mmol) was converted into 18 mg (30%) of high $R^f$ methyl 4-(3-((2R)-2-((E)-3-(2'-(tert-butyl)-4'-chloro-[1,1'-biphenyl]-3-yl)-3-hydroxyprop-1-en-1-yl)-5-oxopyrrolidin-1-yl)propyl)benzoate and 4 mg (7%) of low $R^f$ methyl 4-(3-((2R)-2-((E)-3-(2'-(tert-butyl)-4'-chloro-[1,1'-biphenyl]-3-yl)-3-hydroxyprop-1-en-1-yl)-5-oxopyrrolidin-1-yl)propyl)benzoate.

Step 6. 4-(3-{2(R)-[(1E)-3-(2'-tert-butyl-4'-chlorobiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(2'-(tert-butyl)-4'-chloro-[1,1'-biphenyl]-3-yl)-3-hydroxyprop-1-en-1-yl)-5-oxopyrrolidin-1-yl)propyl)benzoate (high Rf, 18 mg, 0.032 mmol) was converted into 9 mg (51%) 4-(3-{2(R)-[(1E)-3-(2'-tert-butyl-4'-chlorobiphenyl-3-yl)-3-hydroxyprop-1-en-1-yl]-5-oxopyrrolidin-1-yl}propyl)benzoic acid.

Example 27

4-(3-{2(R)-[(1E)-3-(2'-tert-butyl-4'-chlorobiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5 methyl 4-(3-((2R)-2-((E)-3-(2'-(tert-butyl)-4'-chloro-[1,1'-biphenyl]-3-yl)-3-hydroxyprop-1-en-1-yl)-5-oxopyrrolidin-1-yl)propyl)benzoate (low Rf, 4 mg, 0.007 mmol) was converted into 3 mg (77%) of 4-(3-{2(R)-[(1E)-3-(2'-tert-butyl-4'-chlorobiphenyl-3-yl)-3-hydroxyprop-1-en-1-yl]-5-oxopyrrolidin-1-yl}propyl)benzoic acid.

Example 28

4-(3-{2(R)-[(1E)-3-(2'-butyl-4'-chlorobiphenyl-3-yl)-3-hydroxyprop-1-en-1-yl]-5-oxopyrrolidin-1-yl}propyl)benzoic acid (from High $R^f$ Ester)

Step 1. 1-Bromo-2-(but-1-en-1-yl)-4-chlorobenzene. A solution of crude 2-bromo-5-chlorobenzaldehyde (~1.0 g, ~4.56 mmol) in THF (25 mL) was added to a mixture of propyl triphenylphosphonium bromide (dried overnight under vacuum, 6.5 g, 16.86 mmol) in THF (25 mL) at room temperature. Sodium tert-butoxide (1.6 g, 16.65 mmol) was added and the reaction mixture was stirred overnight. The mixture was quenched with saturated aqueous NH$_4$Cl and extracted with EtOAc (2×50 mL). The combined extracts were washed with brine (10 mL), dried (Na$_2$SO$_4$), filtered and concentrated in vacuo. The resulting crude residue was purified on silica gel using a Teledyne-Isco Combiflash machine (80 g gold column, hexanes→100% EtOAc, gradient), to afford 617 mg (55% for 2 steps) of 1-bromo-2-(but-1-en-1-yl)-4-chlorobenzene as a mixture of alkene isomers.

Step 2. methyl 2'-(but-1-en-1-yl)-4'-chloro-[1,1'-biphenyl]-3-carboxylate. In accordance with the procedure of Example 7, step 1, (3-(methoxycarbonyl)phenyl)boronic acid (400 mg, 2.22 mmol) and 1-bromo-2-(but-1-en-1-yl)-4-chlorobenzene (618 mg, 2.51 mmol) were converted into 400 mg (~60%) of impure methyl 2'-(but-1-en-1-yl)-4'-chloro-[1,1'-biphenyl]-3-carboxylate, which was used in the next step without further purification.

Step 3. Methyl 2'-butyl-4'-chloro-[1,1'-biphenyl]-3-carboxylate. In accordance with the procedure of Example 24, step 4, impure methyl 2'-(but-1-en-1-yl)-4'-chloro-[1,1'-biphenyl]-3-carboxylate (~400 mg, ~1.39 mmol) was converted into 400 mg (59% for 2 steps) of methyl 2'-butyl-4'-chloro-[1,1'-biphenyl]-3-carboxylate.

Step 4. Dimethyl (2-(2'-butyl-4'-chloro-[1,1'-biphenyl]-3-yl)-2-oxoethyl)phosphonate. In accordance with the procedure of Example 1, step 1, methyl 2'-butyl-4'-chloro-[1,1'-biphenyl]-3-carboxylate (400 mg, 1.32 mmol) was converted into 300 mg (58%) of dimethyl (2-(2'-butyl-4'-chloro-[1,1'-biphenyl]-3-yl)-2-oxoethyl)phosphonate.

Step 5. (R,E)-Methyl 4-(3-(2-(3-(2'-butyl-4'-chloro-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(2'-butyl-4'-chloro-[1,1'-biphenyl]-3-yl)-2-oxoethyl)phosphonate (300 mg, 0.76 mmol) were converted into 83 mg (22%) of (R,E)-methyl 4-(3-(2-(3-(2'-butyl-4'-chloro-[1,1'-biphenyl]-3-yl)-3-oxoprop-1-en-1-yl)-5-oxopyrrolidin-1-yl)propyl)benzoate.

Step 6. methyl 4-(3-((2R)-2-((E)-3-(2'-butyl-4'-chloro-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(2'-butyl-4'-chloro-[1,1'-biphenyl]-3-yl)-3-oxoprop-1-en-1-yl)-5-oxopyrrolidin-1-yl)propyl)benzoate (83 mg, 0.15 mmol) was converted into 41 mg (49%) of high $R^f$ methyl 4-(3-((2R)-2-((E)-3-(2'-butyl-4'-chloro-[1,1'-biphenyl]-3-yl)-3-hydroxyprop-1-en-1-yl)-5-oxopyrrolidin-1-yl)propyl)benzoate and 35 mg (42%) of low $R^f$ methyl 4-(3-((2R)-2-((E)-3-(2'-butyl-4'-chloro-[1,1'-biphenyl]-3-yl)-3-hydroxyprop-1-en-1-yl)-5-oxopyrrolidin-1-yl)propyl)benzoate.

Step 7. 4-(3-{2(R)-[(1E)-3-(2'-butyl-4'-chlorobiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(2'-butyl-4'-chloro-[1,1'-biphenyl]-3-yl)-3-hydroxyprop-1-en-1-yl)-5-oxopyrrolidin-1-yl)propyl)benzoate (high Rf, 41 mg, 0.073 mmol) was converted into 21 mg (53%) of 4-(3-{2(R)-[(1E)-3-(2'-butyl-4'-chlorobiphenyl-3-yl)-3-hydroxyprop-1-en-1-yl]-5-oxopyrrolidin-1-yl}propyl)benzoic acid.

Example 29

4-(3-{2(R)-[(1E)-3-(2'-butyl-4'-chlorobiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(2'-butyl-4'-chloro-[1,1'-biphenyl]-3-yl)-3-hydroxyprop-1-en-1-yl)-5-oxopyrrolidin-1-yl)propyl)benzoate (low Rf, 35 mg, 0.062 mmol) was converted into 11 mg (32%) of 4-(3-{2(R)-[(1E)-3-(2'-butyl-4'-chlorobiphenyl-3-yl)-3-hydroxyprop-1-en-1-yl]-5-oxopyrrolidin-1-yl}propyl)benzoic acid.

Example 30

4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid (from High $R^f$ Ester)

Step 1. (4-Bromo-3-isopropylphenoxy)(tert-butyl)dimethylsilane. Imidazole (791 mg, 11.6 mmol) and TBSCl (1.05 g, 6.97 mmol) were added to a solution of 4-bromo-3-isopropylphenol (1.0 g, 4.65 mmol) in N,N dimethylformamide (25 mL) at room temperature. The reaction mixture was purged with nitrogen and heated at 60° C. After 2 hours of heating, the reaction mixture was cooled to room temperature, diluted with $CH_2Cl_2$ (100 mL). The mixture was washed with saturated aqueous $NH_4Cl$ (50 mL) and water (10×50 mL), then dried ($MgSO_4$), filtered and concentrated in vacuo. The resulting crude residue was purified by flash chromatography on silica gel, eluting with hexane/EtOAc (30/1) to afford 1.53 g (quant.) of (4-bromo-3-isopropylphenoxy)(tert-butyl)dimethylsilane.

Step 2. Methyl 4'-((tert-butyldimethylsilyl)oxy)-2'-isopropyl-[1,1'-biphenyl]-3-carboxylate. In accordance with the procedure of Example 26, step 2, (3-(methoxycarbonyl)phenyl)boronic acid (110 mg, 0.061 mmol) and (4-bromo-3-isopropylphenoxy)(tert-butyl)dimethylsilane (221 mg, 0.67 mmol) were converted into 200 mg (85%) of methyl 4'-((tert-butyldimethylsilyl)oxy)-2'-isopropyl-[1,1'-biphenyl]-3-carboxylate.

Step 3. Dimethyl (2-(4'-((tert-butyldimethylsilyl)oxy)-2'-isopropyl-[1,1'-biphenyl]-3-yl)-2-oxoethyl)phosphonate. In accordance with the procedure of Example 1, step 1, methyl 4'-((tert-butyldimethylsilyl)oxy)-2'-isopropyl-[1,1'-biphenyl]-3-carboxylate (200 mg, 0.52 mmol) was converted into 191 mg (77%) of dimethyl (2-(4'-((tert-butyldimethylsilyl)oxy)-2'-isopropyl-[1,1'-biphenyl]-3-yl)-2-oxoethyl)phosphonate.

Step 4. (R,E)-Methyl 4-(3-(2-(3-(4'-((tert-butyldimethylsilyl)oxy)-2'-isopropyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-((tert-butyldimethylsilyl)oxy)-2'-isopropyl-[1,1'-biphenyl]-3-yl)-2-oxoethyl)phosphonate (191 mg, 0.40 mmol) were converted into 60 mg (23%) of (R,E)-methyl 4-(3-(2-(3-(4'-((tert-butyldimethylsilyl)oxy)-2'-isopropyl-[1,1'-biphenyl]-3-yl)-3-oxoprop-1-en-1-yl)-5-oxopyrrolidin-1-yl)propyl)benzoate.

Step 5. Methyl 4-(3-((2R)-2-((E)-3-(4'-((tert-butyldimethylsilyl)oxy)-2'-isopropyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-((tert-butyldimethylsilyl)oxy)-2'-isopropyl-[1,1'-biphenyl]-3-yl)-3-oxoprop-1-en-1-yl)-5-oxopyrrolidin-1-yl)propyl)benzoate (60 mg, 0.094 mmol) was converted into 20 mg (33%) of high $R^f$ methyl 4-(3-((2R)-2-((E)-3-(4'-((tert-butyldimethylsilyl)oxy)-2'-isopropyl-[1,1'-biphenyl]-3-yl)-3-hydroxyprop-1-en-1-yl)-5-oxopyrrolidin-1-yl)propyl)benzoate and 17 mg (28%) of low $R^f$ methyl 4-(3-((2R)-2-((E)-3-(4'-((tert-butyldimethylsilyl)oxy)-2'-isopropyl-[1,1'-biphenyl]-3-yl)-3-hydroxyprop-1-en-1-yl)-5-oxopyrrolidin-1-yl)propyl)benzoate.

Step 6. Methyl 4-(3-((2R)-2-((E)-3-hydroxy-3-(4'-hydroxy-2'-isopropyl-[1,1'-biphenyl]-3-yl)prop-1-en-1-yl)-5-oxopyrrolidin-1-yl)propyl)benzoate (from high $R^f$ ester). In accordance with the procedure of Example 18, step 6, methyl 4-(3-((2R)-2-((E)-3-(4'-((tert-butyldimethylsilyl)oxy)-2'-isopropyl-[1,1'-biphenyl]-3-yl)-3-hydroxyprop-1-en-1-yl)-5-oxopyrrolidin-1-yl)propyl)benzoate (high $R^f$ ester, 20 mg, 0.031 mmol) was converted into 12 mg (73%) of methyl 4-(3-((2R)-2-((E)-3-hydroxy-3-(4'-hydroxy-2'-isopropyl-[1,1'-biphenyl]-3-yl)prop-1-en-1-yl)-5-oxopyrrolidin-1-yl)propyl)benzoate.

Step 7. 4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid (from high $R^f$ ester). In accordance with the procedure of Example 7, step 5, methyl 4-(3-((2R)-2-((E)-3-hydroxy-3-(4'-hydroxy-2'-isopropyl-[1,1'-biphenyl]-3-yl)prop-1-en-1-yl)-5-oxopyrrolidin-1-yl)propyl)benzoate (from high $R^f$ ester, 12 mg, 0.023 mmol) was converted into 5 mg (43%) of 4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid.

Example 31

4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid (from Low $R^f$ Ester)

Step 1. Methyl 4-(3-((2R)-2-((E)-3-hydroxy-3-(4'-hydroxy-2'-isopropyl-[1,1'-biphenyl]-3-yl)prop-1-en-1-yl)-5-oxopyrrolidin-1-yl)propyl)benzoate (from low $R^f$ ester). In accordance with the procedure of Example 18, step 6, methyl 4-(3-((2R)-2-((E)-3-(4'-((tert-butyldimethylsilyl)oxy)-2'-isopropyl-[1,1'-biphenyl]-3-yl)-3-hydroxyprop-1-en-1-yl)-5-oxopyrrolidin-1-yl)propyl)benzoate (low $R^f$ ester, 17 mg, 0.026 mmol) was converted into 5 mg (36%) of methyl 4-(3-((2R)-2-((E)-3-hydroxy-3-(4'-hydroxy-2'-isopropyl-[1, 1'-biphenyl]-3-yl)prop-1-en-1-yl)-5-oxopyrrolidin-1-yl)propyl)benzoate.

Step 2. 4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid (from low $R^f$ ester). In accordance with the procedure of Example 7, step 5, methyl 4-(3-((2R)-2-((E)-3-hydroxy-3-(4'-hydroxy-2'-isopropyl-[1, 1'-biphenyl]-3-yl)prop-1-en-1-yl)-5-oxopyrrolidin-1-yl)propyl)benzoate (from low $R^f$ ester, 5 mg, 0.009 mmol) was converted into 2 mg (41%) of 4-[3-(2(R)-{(1E)-3-hydroxy-3-[4'-hydroxy-2'-(propan-2-yl)biphenyl-3-yl]prop-1-en-1-yl}-5-oxopyrrolidin-1-yl)propyl]benzoic acid.

Example 32

4-[3-(2(R)-{(1E)-3-[5-(4-chloro-2-methylphenyl)thiophen-2-yl]-3-hydroxyprop-1-en-1-yl}-5-oxopyrrolidin-1-yl)propyl]benzoic acid (from High $R^f$ Ester)

Step 1. Methyl 5-(4-chloro-2-methylphenyl)thiophene-2-carboxylate. In accordance with the procedure of Example 7, step 1, methyl 5-bromothiophene-2-carboxylate (400 mg, 1.81 mmol) and (4-chloro-2-methylphenyl)boronic acid (617 mg, 3.62 mmol) were converted into approximately 500 mg of impure methyl 5-(4-chloro-2-methylphenyl)thiophene-2-carboxylate which was used in the next step without further purification.

Step 2. Dimethyl (2-(5-(4-chloro-2-methylphenyl)thiophen-2-yl)-2-oxoethyl)phosphonate. In accordance with the procedure of Example 1, step 1, impure methyl 5-(4-chloro-2-methylphenyl)thiophene-2-carboxylate (~1.8 mmol) was converted into 600 mg (49% over 2 steps) of dimethyl (2-(5-(4-chloro-2-methylphenyl)thiophen-2-yl)-2-oxoethyl)phosphonate.

Step 3. (R,E)-Methyl 4-(3-(2-(3-(5-(4-chloro-2-methylphenyl)thiophen-2-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(5-(4-chloro-2-methylphenyl)thiophen-2-yl)-2-oxoethyl)phosphonate (273 mg, 0.76 mmol) were converted into 200 mg (56%) of (R,E)-methyl 4-(3-(2-(3-(5-(4-chloro-2-methylphenyl)thiophen-2-yl)-3-oxoprop-1-en-1-yl)-5-oxopyrrolidin-1-yl)propyl)benzoate.

Step 4. Methyl 4-(3-((2R)-2-((E)-3-(5-(4-chloro-2-methylphenyl)thiophen-2-yl)-3-hydroxyprop-1-en-1-yl)-5-oxopyrrolidin-1-yl)propyl)benzoate. In accordance with Example 1, step 3, (R,E)-methyl 4-(3-(2-(3-(5-(4-chloro-2-methylphenyl)thiophen-2-yl)-3-oxoprop-1-en-1-yl)-5-oxopyrrolidin-1-yl)propyl)benzoate (200 mg, 0.38 mmol) was converted into 60 mg (30%) of high $R^f$ methyl 4-(3-((2R)-2-((E)-3-(5-(4-chloro-2-methylphenyl)thiophen-2-yl)-3-hydroxyprop-1-en-1-yl)-5-oxopyrrolidin-1-yl)propyl)benzoate and 24 mg (12%) of low $R^f$ methyl 4-(3-((2R)-2-((E)-3-(5-(4-chloro-2-methylphenyl)thiophen-2-yl)-3-hydroxyprop-1-en-1-yl)-5-oxopyrrolidin-1-yl)propyl)benzoate.

Step 5. 4-[3-(2(R)-{(1E)-3-[5-(4-chloro-2-methylphenyl)thiophen-2-yl]-3-hydroxyprop-1-en-1-yl}-5-oxopyrrolidin-1-yl)propyl]benzoic acid (from high $R^f$ ester). In accordance with example 7, step 5, methyl 4-(3-((2R)-2-((E)-3-(5-(4-chloro-2-methylphenyl)thiophen-2-yl)-3-hydroxyprop-1-en-1-yl)-5-oxopyrrolidin-1-yl)propyl)benzoate (high Rf, 30 mg, 0.057 mmol) was converted into 19 mg (65%) of 4-[3-(2(R)-{(1E)-3-[5-(4-chloro-2-methylphenyl)thiophen-2-yl]-3-hydroxyprop-1-en-1-yl}-5-oxopyrrolidin-1-yl)propyl]benzoic acid after purification on silica gel using a Teledyne-Isco Combiflash machine (4 g column, CH$_2$Cl$_2$ to 15% methanol/CH$_2$Cl$_2$, 120 minute gradient).

Example 33

4-[3-(2(R)-{(1E)-3-[5-(4-chloro-2-methylphenyl)thiophen-2-yl]-3-hydroxyprop-1-en-1-yl}-5-oxopyrrolidin-1-yl)propyl]benzoic acid (from Low $R^f$ Ester)

In accordance with example 7, step 5, methyl 4-(3-((2R)-2-((E)-3-(5-(4-chloro-2-methylphenyl)thiophen-2-yl)-3-hydroxyprop-1-en-1-yl)-5-oxopyrrolidin-1-yl)propyl)benzoate (low Rf, 12 mg, 0.023 mmol) was converted into 7 mg (60%) of 4-[3-(2(R)-{(1E)-3-[5-(4-chloro-2-methylphenyl)thiophen-2-yl]-3-hydroxyprop-1-en-1-yl}-5-oxopyrrolidin-1-yl)propyl]benzoic acid after purification on silica gel using a Teledyne-Isco Combiflash machine (4 g column, CH$_2$Cl$_2$ to 15% methanol/CH$_2$Cl$_2$, 120 minute gradient).

Example 34

4-(3-{2(R)-[(1E)-3-(4'-chloro-5-fluoro-2'-methylbiphenyl-3-yl)-3-hydroxyprop-1-en-1-yl]-5-oxopyrrolidin-1-yl}propyl)benzoic acid (from High $R^f$ Ester)

Step 1. Methyl 4'-chloro-5-fluoro-2'-methyl-[1,1'-biphenyl]-3-carboxylate. A 5 mL microwave vial (Biotage) was charged with methyl 3-bromo-5-fluorobenzoate (400 mg, 1.72 mmol), cesium carbonate (1.12 g, 3.43 mmol) and (4-chloro-2-methylphenyl)boronic acid (585 mg, 3.43 mmol) and purged with nitrogen. Toluene (5 mL) and tetrakis(triphenylphosphine) palladium (0) (20 mg, 0.17 mmol) were added to the mixture. Methanol (1 mL) was added down the walls of the vial to rinse in adhered palladium catalyst. The vial was capped and sealed with a standard Biotage microwave cap. The reaction was heated 135° C. for 30 minutes using a Biotage microwave. The reaction was then cooled, diluted with toluene and filtered through celite. The filtrate was concentrated in vacuo. The resulting crude residue was purified on silica gel using a Teledyne-Isco Combiflash machine (12 g column, hexanes to 100% EtOAc, gradient), to afford 200 mg (42%) of methyl 4'-chloro-5-fluoro-2'-methyl-[1,1'-biphenyl]-3-carboxylate.

Step 2. Dimethyl (2-(4'-chloro-5-fluoro-2'-methyl-[1,1'-biphenyl]-3-yl)-2-oxoethyl)phosphonate. In accordance with the procedure of Example 1, step 1, methyl 4'-chloro-5-fluoro-2'-methyl-[1,1'-biphenyl]-3-carboxylate (200 mg, 0.72 mmol) was converted into 265 mg (99%) of dimethyl (2-(4'-chloro-5-fluoro-2'-methyl-[1,1'-biphenyl]-3-yl)-2-oxoethyl)phosphonate.

Step 3. (R,E)-Methyl 4-(3-(2-(3-(4'-chloro-5-fluoro-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-5-fluoro-2'-methyl-[1,1'-biphenyl]-3-yl)-2-oxoethyl)phosphonate (282 mg, 0.76 mmol) were converted into 94 mg (25%) of (R,E)-methyl 4-(3-(2-(3-(4'-chloro-5-fluoro-2'-methyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-chloro-5-fluoro-2'-methyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-5-fluoro-2'-methyl-[1,1'-biphenyl]-3-yl)-3-oxoprop-1-en-1-yl)-5-oxopyrrolidin-1-yl)propyl)benzoate (44 mg, 0.083 mmol) was converted into 34 mg (75%) of high $R^f$ methyl 4-(3-((2R)-2-((E)-3-(4'-chloro-5-fluoro-2'-methyl-[1,1'-biphenyl]-3-yl)-3-hydroxyprop-1-en-1-yl)-5-oxopyrrolidin-1-yl)propyl)benzoate and 12 mg (25%) of low $R^f$ methyl 4-(3-((2R)-2-((E)-3-(4'-chloro-5-fluoro-2'-methyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(4'-chloro-5-fluoro-2'-methylbiphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-chloro-5-fluoro-2'-methyl-[1,1'-biphenyl]-3-yl)-3-hydroxyprop-1-en-1-yl)-5-oxopyrrolidin-1-yl)propyl)benzoate (high Rf, 34 mg, 0.63 mmol) was converted into 22 mg (66%) of 4-(3-{2(R)-[(1E)-3-(4'-chloro-5-fluoro-2'-methylbiphenyl-3-yl)-3-hydroxyprop-1-en-1-yl]-5-oxopyrrolidin-1-yl}propyl)benzoic acid.

Example 35

4-(3-{2(R)-[(1E)-3-(4'-chloro-5-fluoro-2'-methylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(4'-chloro-5-fluoro-2'-methyl-[1,1'-biphenyl]-3-yl)-3-hydroxyprop-1-en-1-yl)-5-oxopyrrolidin-1-yl)propyl)benzoate (low Rf, 12 mg, 0.22 mmol) was converted into 4 mg (34%) of 4-(3-{2(R)-[(1E)-3-(4'-chloro-5-fluoro-2'-methylbiphenyl-3-yl)-3-hydroxyprop-1-en-1-yl]-5-oxopyrrolidin-1-yl}propyl)benzoic acid.

Example 36

4-(3-{2(R)-[(1E)-3-(4'-chloro-6-fluoro-2'-methylbiphenyl-3-yl)-3-hydroxyprop-1-en-1-yl]-5-oxopyrrolidin-1-yl}propyl)benzoic acid (from High $R^f$ Ester)

Step 1. Methyl 4'-chloro-6-fluoro-2'-methyl-[1,1'-biphenyl]-3-carboxylate. In accordance with the procedure of Example 34, step 1, methyl 3-bromo-4-fluorobenzoate (400 mg, 1.72 mmol) and (4-chloro-2-methylphenyl)boronic acid (585 mg, 3.43 mmol) were converted into 200 mg (42%) of methyl 4'-chloro-6-fluoro-2'-methyl-[1,1'-biphenyl]-3-carboxylate.

Step 2. Dimethyl (2-(4'-chloro-6-fluoro-2'-methyl-[1,1'-biphenyl]-3-yl)-2-oxoethyl)phosphonate. In accordance with the procedure of Example 1, step 1, methyl 4'-chloro-6-fluoro-2'-methyl-[1,1'-biphenyl]-3-carboxylate (200 mg, 0.72 mmol) was converted into 250 mg (94%) of dimethyl (2-(4'-chloro-6-fluoro-2'-methyl-[1,1'-biphenyl]-3-yl)-2-oxoethyl)phosphonate.

Step 3. (R,E)-Methyl 4-(3-(2-(3-(4'-chloro-6-fluoro-2'-methyl-[1,1'-biphenyl]-3-yl)-3-oxoprop-1-en-1-yl)-5-oxopyrrolidin-1-yl)propyl)benzoate. In accordance with the procedure of Example 1, step 2, (R)-methyl 4-(3-(2-formyl-5-oxopyrrolidin-1-yl)propyl)benzoate (200 mg, 0.69 mmol) and dimethyl (2-(4'-chloro-6-fluoro-2'-methyl-[1,1'-biphenyl]-3-yl)-2-oxoethyl)phosphonate (250 mg, 0.67 mmol) were converted into 89 mg (25%) of (R,E)-methyl 4-(3-(2-(3-(4'-chloro-6-fluoro-2'-methyl-[1,1'-biphenyl]-3-yl)-3-oxoprop-1-en-1-yl)-5-oxopyrrolidin-1-yl)propyl)benzoate.

Step 4. Methyl 4-(3-((2R)-2-((E)-3-(4'-chloro-6-fluoro-2'-methyl-[1,1'-biphenyl]-3-yl)-3-hydroxyprop-1-en-1-yl)-5-oxopyrrolidin-1-yl)propyl)benzoate. In accordance with the procedure of Example 1, step 3, (R,E)-methyl 4-(3-(2-(3-(4'-chloro-6-fluoro-2'-methyl-[1,1'-biphenyl]-3-yl)-3-oxoprop-1-en-1-yl)-5-oxopyrrolidin-1-yl)propyl)benzoate (89 mg, 0.17 mmol) was converted into 48 mg (54%) of high $R^f$ methyl 4-(3-((2R)-2-((E)-3-(4'-chloro-6-fluoro-2'-methyl-[1,1'-biphenyl]-3-yl)-3-hydroxyprop-1-en-1-yl)-5-oxopyrrolidin-1-yl)propyl)benzoate and 16 mg (18%) of low $R^f$ methyl 4-(3-((2R)-2-((E)-3-(4'-chloro-6-fluoro-2'-methyl-[1,1'-biphenyl]-3-yl)-3-hydroxyprop-1-en-1-yl)-5-oxopyrrolidin-1-yl)propyl)benzoate.

Step 5. 4-(3-{2(R)-[(1E)-3-(4'-chloro-6-fluoro-2'-methyl-biphenyl-3-yl)-3-hydroxyprop-1-en-1-yl]-5-oxopyrrolidin-1-yl}propyl)benzoic acid (from high $R^f$ ester). In accordance with the procedure of Example 7, step 5, methyl 4-(3-((2R)-2-((E)-3-(4'-chloro-6-fluoro-2'-methyl-[1,1'-biphenyl]-3-yl)-3-hydroxyprop-1-en-1-yl)-5-oxopyrrolidin-1-yl)propyl)benzoate (high Rf, 24 mg, 0.045 mmol) was converted into 14 mg (60%) of 4-(3-{2(R)-[(1E)-3-(4'-chloro-6-fluoro-2'-methylbiphenyl-3-yl)-3-hydroxyprop-1-en-1-yl]-5-oxopyrrolidin-1-yl}propyl)benzoic acid.

Example 37

4-(3-{2(R)-[(1E)-3-(4'-chloro-6-fluoro-2'-methylbiphenyl-3-yl)-3-hydroxyprop-1-en-1-yl]-5-oxopyrrolidin-1-yl}propyl)benzoic acid (from Low $R^f$ Ester)

In accordance with the procedure of Example 7, step 5, methyl 4-(3-((2R)-2-((E)-3-(4'-chloro-6-fluoro-2'-methyl-[1,1'-biphenyl]-3-yl)-3-hydroxyprop-1-en-1-yl)-5-oxopyrrolidin-1-yl)propyl)benzoate (low Rf, 8 mg, 0.015 mmol) was converted into 5 mg (64%) of 4-(3-{2(R)-[(1E)-3-(4'-chloro-6-fluoro-2'-methylbiphenyl-3-yl)-3-hydroxyprop-1-en-1-yl]-5-oxopyrrolidin-1-yl}propyl)benzoic acid.

Binding Data (Ki)

Competition binding experiments were performed in a medium containing Hank's balanced salt solution, HEPES 20 mM, pH 7.3, membranes (~60 µg protein) or $2\times10^5$ cells from HEK 293 cells stably expressing human EP2 receptors, [$^3$H]PGE2 (10 nM) and various concentrations of test compounds in a total volume of 300 µl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 µM). Binding data fitted to the binding model for a single class of binding sites, using nonlinear regression analysis. $IC_{50}$ values thus obtained were converted to Ki using the equation of Ki= $(IC_{50}/(1+[L]/K_D)$ where [L] represents PGE2 concentration (10 nM) and $K_D$ the dissociation constant for [$^3$H]PGE2 at human EP2 receptors (40 nM).

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP$_4$/Gqs5; hFP; hIP; hTP), were cultured in 100 mm culture dishes in high-glucose DMEM medium containing 10% fetal bovine serum, 2 mM l-glutamine, 250 µg/ml geneticin (G418) and 200 microgram/mL hygromycin B as selection markers, and 100 units/ml penicillin G, 100 microgram/mL streptomycin and 0.25 microgram/mL amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 microliters in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 microliter volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3A}$/Gqi5; hEP$_4$/Gqs5); PGF$_{2a}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, up to forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an n≥3.

cAMP Assay

A 384-well drug plate was prepared to contain 6 test compounds, PGE2 and cAMP in 16 serial dilutions in triplicate, using a Biomek station. HEK-EBNA cells expressing a target PG receptor subtype (EP2 or EP4) were suspended in a stimulation buffer (HBSS, 0.1% BSA, 0.5 mM IBMX and 5 mM HEPES, pH 7.4) in a density of $10^4$ cells/5 microliters. The reaction was initiated by mixing 5 microliters drug dilutions with 5 microliters of HEK-EBNA cells in a well, carried out for 30 min at room temperature, and followed by the addition of 5 microliters anti-cAMP acceptor beads in the control buffer with Tween-20 (25 mM NaCl, 0.03% Tween-20, 5 mM HEPES, pH 7.4). After 30 min in the dark at room temperature, the mixtures were incubated with 15 microliters biotinylated-cAMP/streptavidin donor beads in Lysis/Detection buffer (0.1% BSA, 0.3% Tween-20 and 5 mM HEPES, pH 7.4) for 45 min at room temperature. Fluorescence changes were read using a Fusion-alpha microplate reader.

The results of the binding and activity studies are presented in Table 2 and in the subsequent paragraph.

Table 2. EP2 and EP4 binding and activity data. NT: Not tested.

TABLE 2

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 1 | (structure) | High | NT | >10K | >10K | 2037 |
| 2 | (structure) | Low | 149 | 7493 | 194 | 1207 |
| 3 | (structure) | High | NT | >10K | 9207 | >10K |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 4 | | Low | NT | >10K | 5543 | 4973 |
| 5 | | High | NT | >10K | NT | 8557 |
| 6 | | Low | NT | >10K | >10K | 6714 |
| 7 | | High | NT | >10K | 14 | 1154 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 8 | 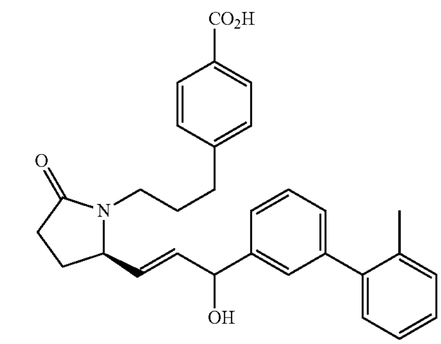 [SMILES: Cc1ccccc1-c1cccc(C(O)/C=C/[C@H]2CCC(=O)N2CCCc2ccc(C(=O)O)cc2)c1] | Low | NT | >10K | 2 | 159 |
| 9 | 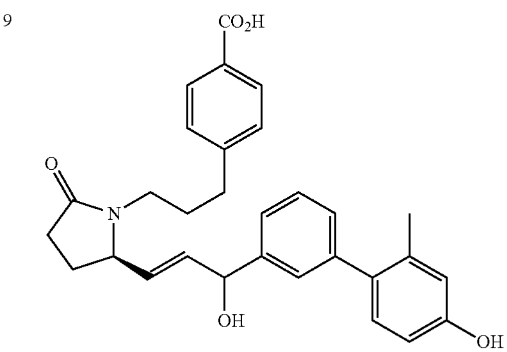 | High | NT | >10K | 326 | 3322 |
| 10 | 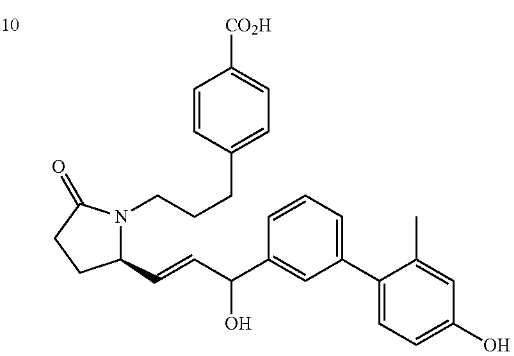 | Low | NT | >10K | 3 | 25 |
| 11 | 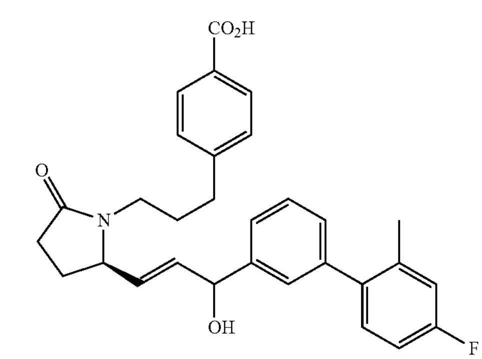 [SMILES: Cc1cc(F)ccc1-c1cccc(C(O)/C=C/[C@H]2CCC(=O)N2CCCc2ccc(C(=O)O)cc2)c1] | High | NT | >10K | NT | >1341 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
| --- | --- | --- | --- | --- | --- | --- |
| 12 | 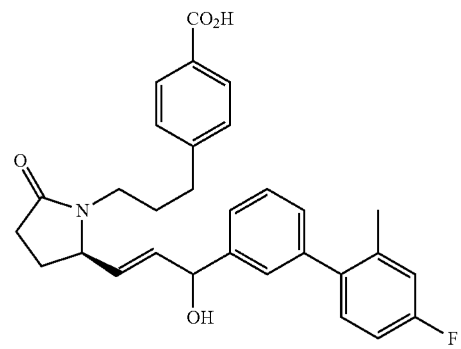 [SMILES: Cc1cc(F)ccc1-c1cccc(C(O)/C=C/[C@H]2CCC(=O)N2CCCc2ccc(C(=O)O)cc2)c1] | Low | NT | >10K | 8 | 53 |
| 13 | 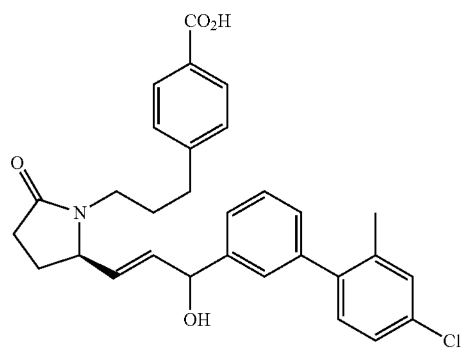 [SMILES: Cc1cc(Cl)ccc1-c1cccc(C(O)/C=C/[C@H]2CCC(=O)N2CCCc2ccc(C(=O)O)cc2)c1] | Low | NT | 4322 | 4 | 23 |
| 14 | 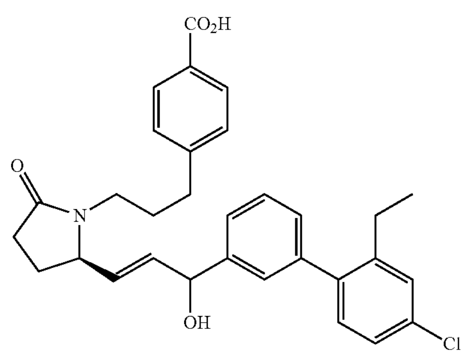 [SMILES: CCc1cc(Cl)ccc1-c1cccc(C(O)/C=C/[C@H]2CCC(=O)N2CCCc2ccc(C(=O)O)cc2)c1] | High | NT | >10K | 33 | 216 |
| 15 | 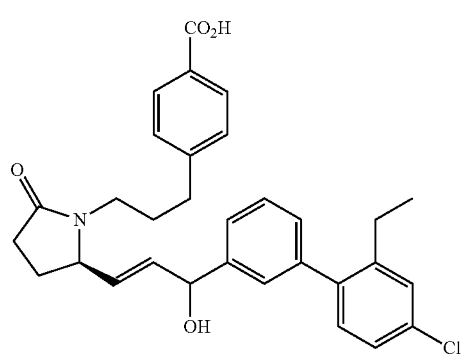 [SMILES: CCc1cc(Cl)ccc1-c1cccc(C(O)/C=C/[C@H]2CCC(=O)N2CCCc2ccc(C(=O)O)cc2)c1] | Low | NT | >10K | 3 | 6 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 16 | 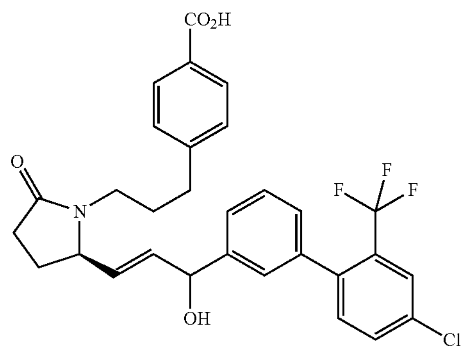 [SMILES: O=C(O)c1ccc(CCCN2C(=O)CC[C@@H]2/C=C/C(O)c2cccc(-c3ccc(Cl)cc3C(F)(F)F)c2)cc1] | High | NT | >10K | 87 | 332 |
| 17 | 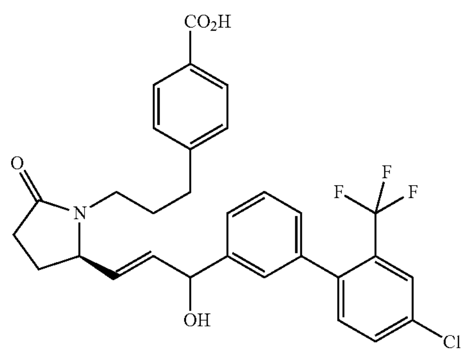 [SMILES: O=C(O)c1ccc(CCCN2C(=O)CC[C@@H]2/C=C/C(O)c2cccc(-c3ccc(Cl)cc3C(F)(F)F)c2)cc1] | Low | NT | >10K | 3 | 11 |
| 18 | 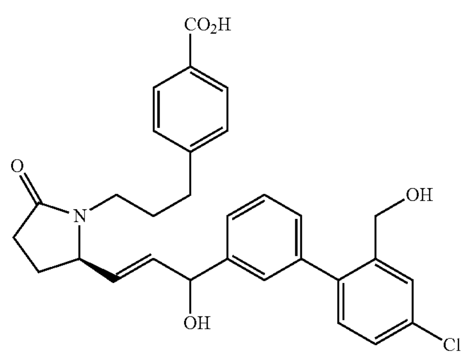 [SMILES: O=C(O)c1ccc(CCCN2C(=O)CC[C@@H]2/C=C/C(O)c2cccc(-c3ccc(Cl)cc3CO)c2)cc1] | High | NT | >10K | >10K | >10K |
| 19 | 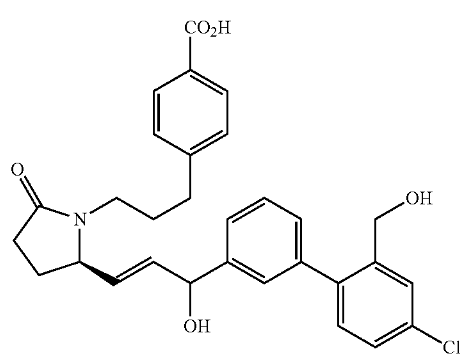 [SMILES: O=C(O)c1ccc(CCCN2C(=O)CC[C@@H]2/C=C/C(O)c2cccc(-c3ccc(Cl)cc3CO)c2)cc1] | Low | NT | >10K | 95,165 | 658 |

TABLE 2-continued

EP2 and EP4 binding and activity data. NT: Not tested.

| Example # | Structure | Relative Rf of Benzoate Ester Intermediate | EP2 cAMP $EC_{50}$ (nM) | EP2 Ki (nM) | EP4 cAMP $EC_{50}$ (nM) | EP4 Ki (nM) |
|---|---|---|---|---|---|---|
| 20 | 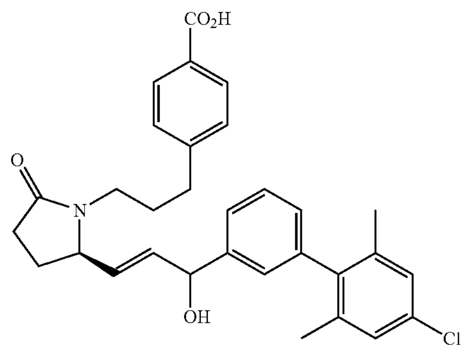 [SMILES: Cc1cc(Cl)cc(C)c1-c1cccc(C(O)/C=C/[C@H]2CCC(=O)N2CCCc2ccc(C(=O)O)cc2)c1] | High | NT | >10K | 138 | 955 |
| 21 | 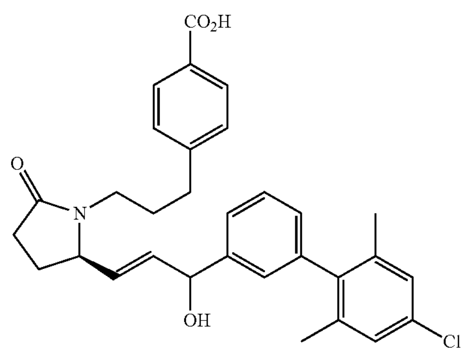 [SMILES: Cc1cc(Cl)cc(C)c1-c1cccc(C(O)/C=C/[C@H]2CCC(=O)N2CCCc2ccc(C(=O)O)cc2)c1] | Low | NT | >10K | 2 | 60 |
| 22 | 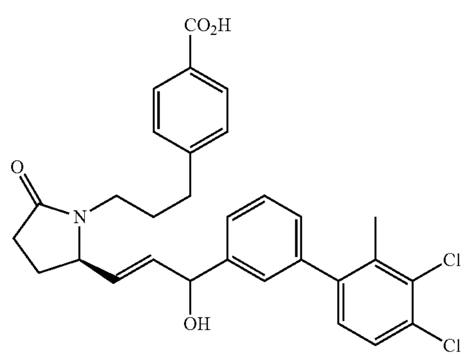 [SMILES: Cc1c(-c2cccc(C(O)/C=C/[C@H]3CCC(=O)N3CCCc3ccc(C(=O)O)cc3)c2)ccc(Cl)c1Cl] | High | NT | >10K | 35 | 2342 |
| 23 | 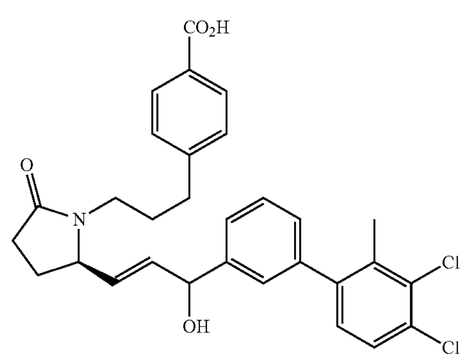 [SMILES: Cc1c(-c2cccc(C(O)/C=C/[C@H]3CCC(=O)N3CCCc3ccc(C(=O)O)cc3)c2)ccc(Cl)c1Cl] | Low | NT | >10K | 3 | 140 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 24 | 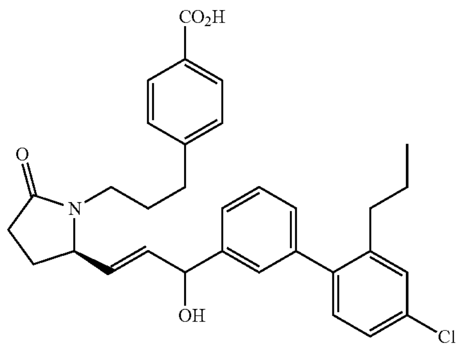 [SMILES: CCCc1cc(Cl)ccc1-c1cccc(C(O)/C=C/[C@H]2CCC(=O)N2CCCc2ccc(C(=O)O)cc2)c1] | High | NT | >10K | 2343 | 1312 |
| 25 | 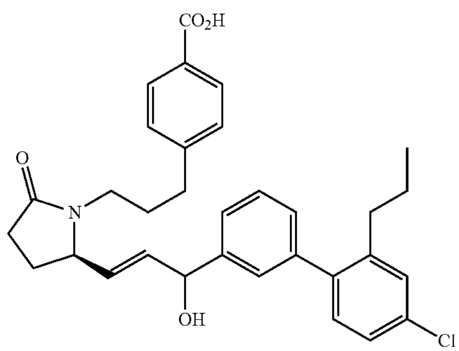 [SMILES: CCCc1cc(Cl)ccc1-c1cccc(C(O)/C=C/[C@H]2CCC(=O)N2CCCc2ccc(C(=O)O)cc2)c1] | Low | NT | >10K | 63 | 130 |
| 26 | 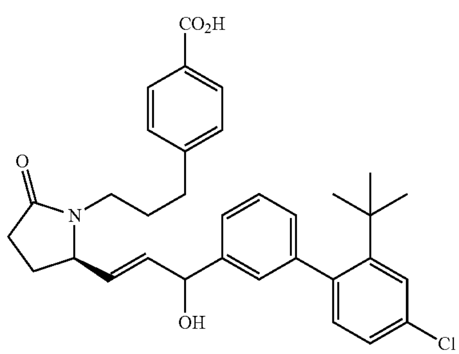 [SMILES: CC(C)(C)c1cc(Cl)ccc1-c1cccc(C(O)/C=C/[C@H]2CCC(=O)N2CCCc2ccc(C(=O)O)cc2)c1] | High | NT | >10K | >10K | 8849 |
| 27 | 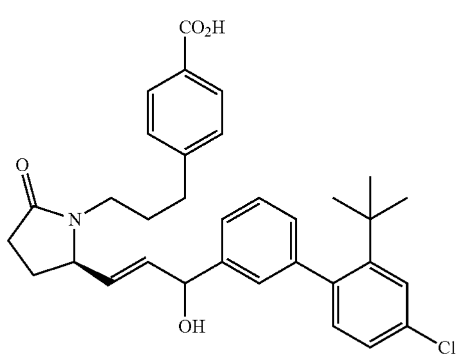 [SMILES: CC(C)(C)c1cc(Cl)ccc1-c1cccc(C(O)/C=C/[C@H]2CCC(=O)N2CCCc2ccc(C(=O)O)cc2)c1] | Low | NT | >10K | 107 | 757 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 28 | 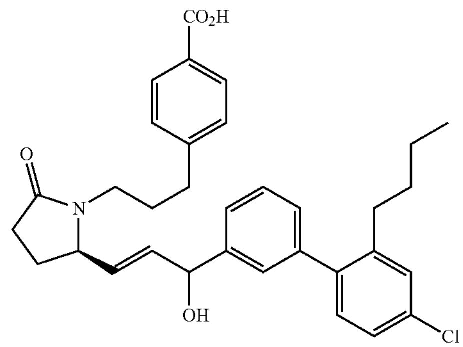 [SMILES: CCCCc1cc(Cl)ccc1-c1cccc(C(O)/C=C/[C@H]2CCC(=O)N2CCCc2ccc(C(=O)O)cc2)c1] | High | NT | >10K | NT | 5158 |
| 29 | 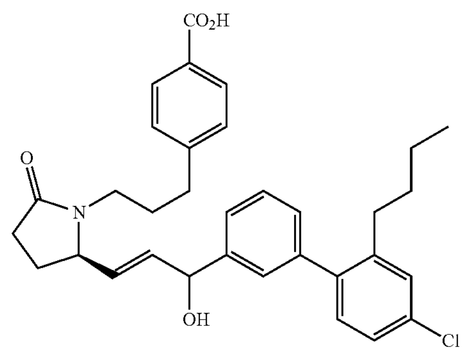 [SMILES: CCCCc1cc(Cl)ccc1-c1cccc(C(O)/C=C/[C@H]2CCC(=O)N2CCCc2ccc(C(=O)O)cc2)c1] | Low | NT | >10K | 117 | 319 |
| 30 | 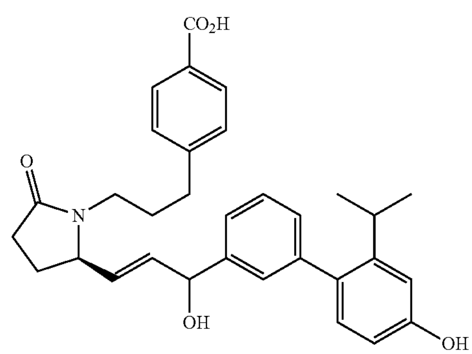 [SMILES: CC(C)c1cc(O)ccc1-c1cccc(C(O)/C=C/[C@H]2CCC(=O)N2CCCc2ccc(C(=O)O)cc2)c1] | High | NT | >10K | 134 | 582 |
| 31 | 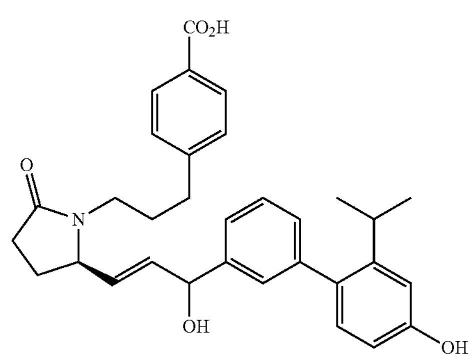 [SMILES: CC(C)c1cc(O)ccc1-c1cccc(C(O)/C=C/[C@H]2CCC(=O)N2CCCc2ccc(C(=O)O)cc2)c1] | Low | NT | >10K | 60 | 211 |

TABLE 2-continued
EP2 and EP4 binding and activity data. NT: Not tested.
| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 32 | 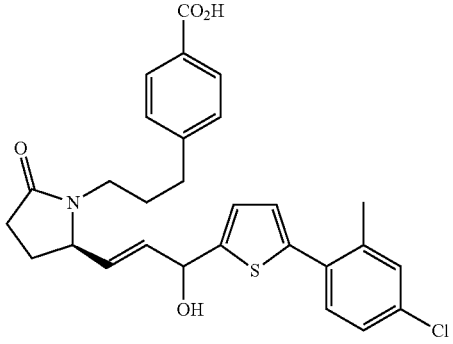 [SMILES: Cc1cc(Cl)ccc1-c1ccc(C(O)/C=C/[C@H]2CCC(=O)N2CCCc2ccc(C(=O)O)cc2)s1] | High | NT | >10K | NT | 4831 |
| 33 | 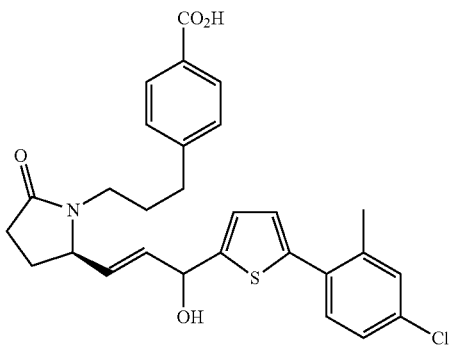 [SMILES: Cc1cc(Cl)ccc1-c1ccc(C(O)/C=C/[C@H]2CCC(=O)N2CCCc2ccc(C(=O)O)cc2)s1] | Low | NT | >10K | 118 | 536 |
| 34 | 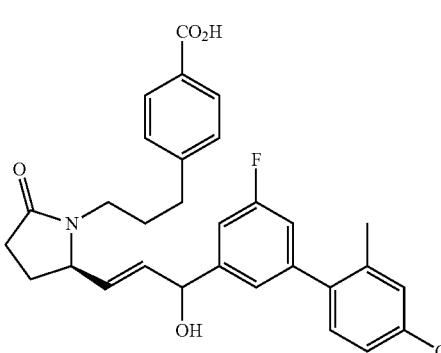 | High | NT | >10K | 1735 | 4342 |
| 35 | 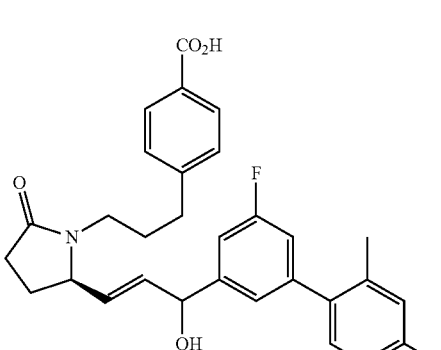 | Low | NT | >10K | 59, 99 | 352 |

TABLE 2-continued

EP2 and EP4 binding and activity data. NT: Not tested.

| Example # | Structure | Relative Rf of Benzoate Ester Intermediate | EP2 cAMP EC$_{50}$ (nM) | EP2 Ki (nM) | EP4 cAMP EC$_{50}$ (nM) | EP4 Ki (nM) |
|---|---|---|---|---|---|---|
| 36 | CO$_2$H structure | High | NT | >10K | 1033 | 4477 |
| 37 | CO$_2$H structure | Low | NT | 7493 | 123, 211 | 1079 |

The compounds of Examples 5-8 and 11-37 were evaluated to determine their EC$_{50}$ values against receptors hFP, hEP1, hEP3A, hTP, hIP, and hDP, and were not active. The compounds of Examples 9 and 10 were not tested for activity against hIP. When evaluated for EC$_{50}$ against hFP, hEP1, hEP3A, hTP and hDP, the compounds of Examples 9 and 10 were not active. The compounds of Examples 1-4 were not tested for activity against hFP, hEP1, hEP3A, hTP, hIP, or hDP.

The results of the binding and activity studies presented in Table 2 and in the preceding paragraph demonstrate that the compounds disclosed herein are selective prostaglandin EP4 agonists, and are thus useful for treating skin blemishes, healing wounds, and reducing scars, and treating other conditions mediated by EP4.

While this invention has been described with respect to these specific examples, it is understood that other modifications and variations are possible without departing from the spirit of the invention.

What is claimed is:

1. A compound of Formula I:

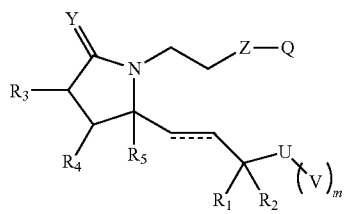

Formula I wherein:
Y is O;
Z is CH$_2$;
Q is aryl or heteroaryl, wherein said aryl and heteroaryl groups are optionally substituted with one or more R$^6$;

U is aryl or heteroaryl, wherein said aryl and heteroaryl groups are optionally substituted with one or more $R^7$;

V is aryl or heteroaryl; wherein said aryl and heteroaryl groups are optionally substituted with one or more $R^8$;

$R^1$ is —$OR^a$, wherein $R^a$ is H;

$R^2$ is H;

each $R^3$, $R^4$ and $R^5$ is H;

each $R^6$ is independently —$CO_2R^e$, —$CH_2OR^e$, —$CONR^eR^f$, or tetrazol-5-yl; wherein each $R^e$ is independently H, $C_1$-$C_6$ alkyl, haloalkyl, hydroxyalkyl, or aryl, and each $R^f$ is independently H, $C_1$-$C_6$ alkyl, $C(O)R^g$, or $SO_2R^g$, wherein $R^g$ is $C_1$-$C_6$ alkyl, $CF_3$, aryl, or heteroaryl;

each $R^7$ is independently H, $C_1$-$C_6$ alkyl, haloalkyl, halo, hydroxyl, nitro, cyano, or amino;

each $R^8$ is independently H, $C_1$-$C_6$ alkyl, haloalkyl, hydroxyalkyl, hydroxyl, halo, aryl, or heteroaryl; and m is 1;

wherein the dashed line represents the presence of a bond, and wherein the resulting olefin geometry is trans;

each aryl is $C_6$ aryl; and each heteroaryl comprises 5 or 6;

or a pharmaceutically acceptable salt thereof.

2. The compound of claim 1, wherein:

Q is:

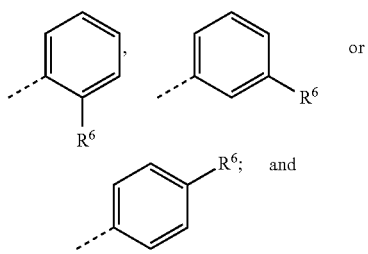

$R^6$ is —$CO_2R^e$, wherein $R^e$ is H, $C_1$-$C_6$ alkyl, haloalkyl, hydroxyalkyl, or aryl; or a pharmaceutically acceptable salt thereof.

3. The compound of claim 1, wherein:

U is:

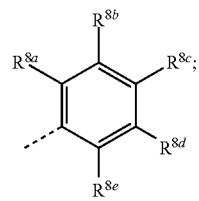

$R^{7a}$ is H, $C_1$-$C_6$alkyl, haloalkyl, halo, hydroxyl, nitro, cyano, or amino;

$R^{7b}$ is H, $C_1$-$C_6$alkyl, haloalkyl, halo, hydroxyl, nitro, cyano, or amino;

$R^{7c}$ is H, $C_1$-$C_6$alkyl, haloalkyl, halo, hydroxyl, nitro, cyano, or amino;

$R^{7d}$ is H, $C_1$-$C_6$alkyl, haloalkyl, halo, hydroxyl, nitro, cyano, or amino;

V is:

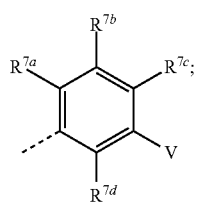

$R^{8a}$ is H, $C_1$-$C_6$alkyl, haloalkyl, halo, hydroxyl, hydroxyalkyl, aryl, or heteroaryl;

$R^{8b}$ is H, $C_1$-$C_6$alkyl, haloalkyl, halo, hydroxyl, hydroxyalkyl, aryl, or heteroaryl;

$R^{8c}$ is H, $C_1$-$C_6$alkyl, haloalkyl, halo, hydroxyl, hydroxyalkyl, aryl, or heteroaryl;

$R^{8d}$ is H, $C_1$-$C_6$alkyl, haloalkyl, halo, hydroxyl, hydroxyalkyl, aryl, or heteroaryl; and $R^{8e}$ is H, $C_1$-$C_6$alkyl, haloalkyl, halo, hydroxyl, hydroxyalkyl, aryl, or heteroaryl;

or a pharmaceutically acceptable salt thereof.

4. The compound of claim 3, wherein:

Q is:

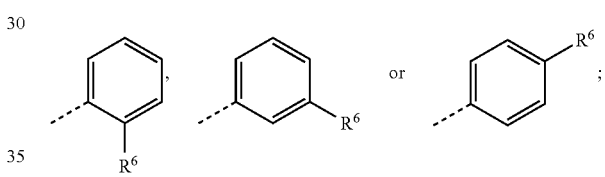

and $R^6$ is —$CO_2R^e$, wherein $R^e$ is H, $C_1$-$C_6$ alkyl, haloalkyl, hydroxyalkyl, or aryl;

or a pharmaceutically acceptable salt thereof.

5. The compound of claim 4 having the structure of Formula 1c:

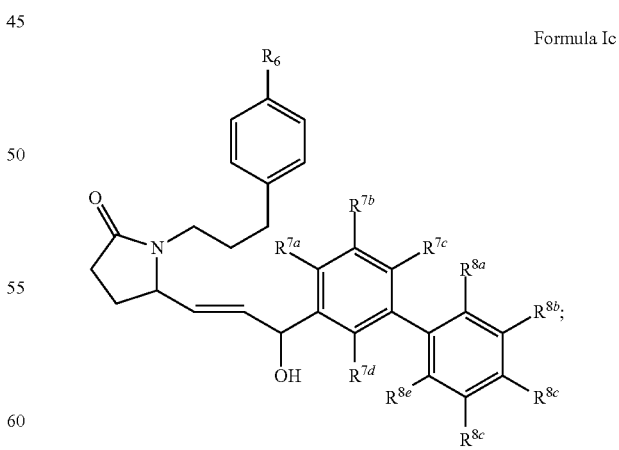

Formula Ic wherein $R^6$ is —$CO_2R^e$, and $R^e$ is H;

or a pharmaceutically acceptable salt thereof.

6. The compound of claim 5 having the structure of Formula Id:

Formula Id
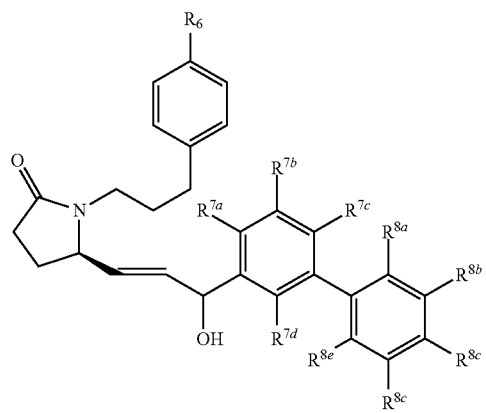
wherein $R^6$ is —$CO_2R^e$, and $R^e$ is H;
or a pharmaceutically acceptable salt thereof.
7. The compound of claim 1, wherein the compound is selected from the group consisting of:
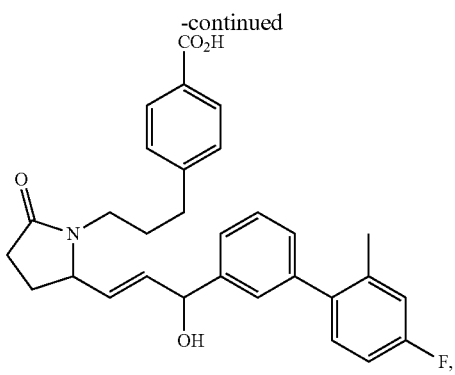
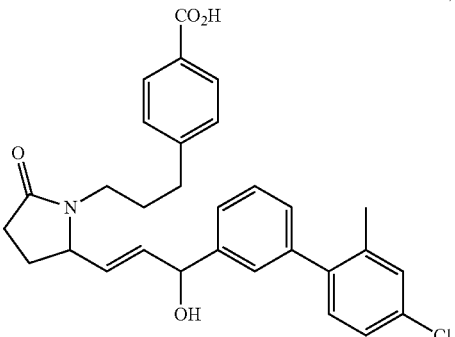
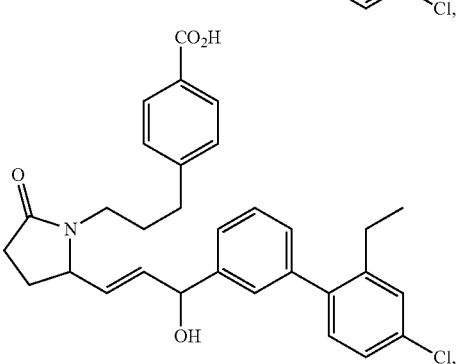
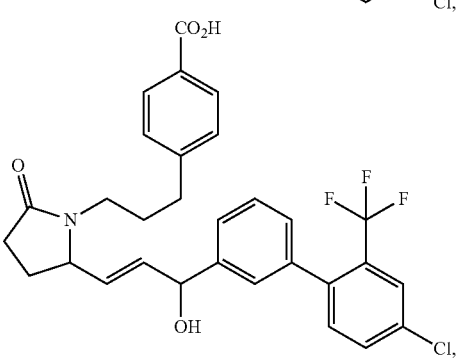
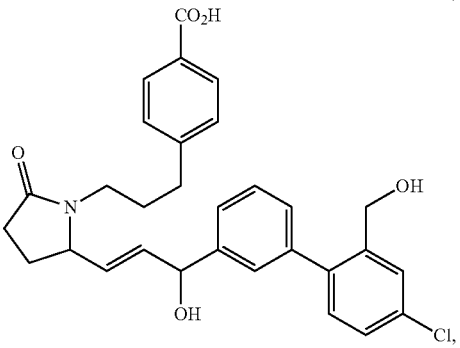

-continued
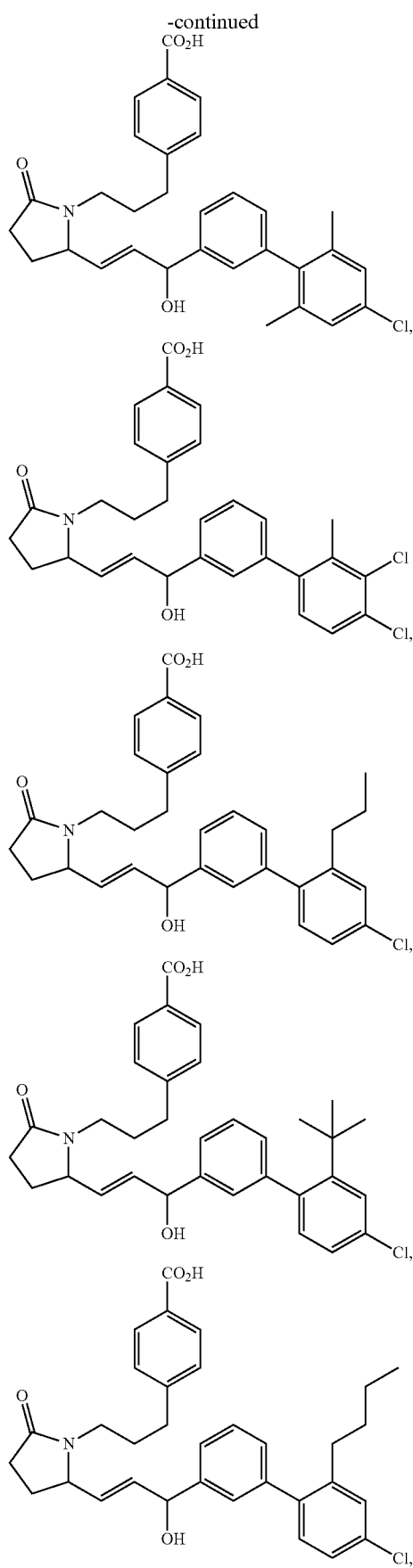
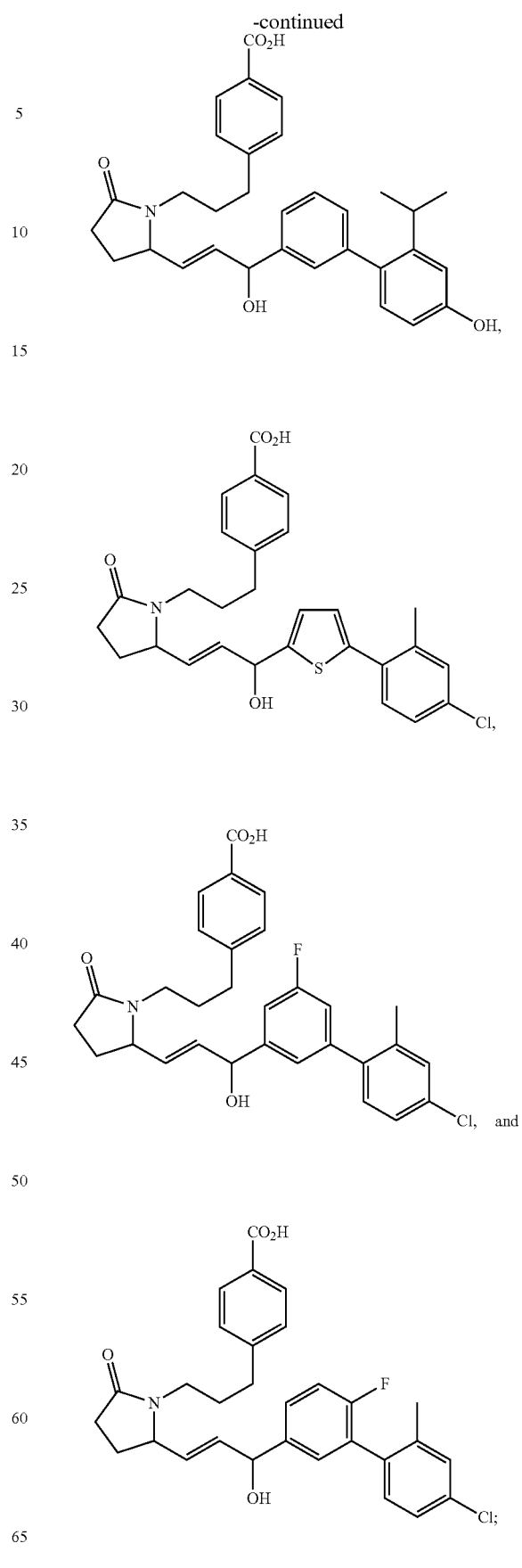
or pharmaceutically acceptable salts.

8. A pharmaceutical composition comprising a compound of claim 1 or a pharmaceutically acceptable salt thereof, and a pharmaceutically acceptable carrier.

9. A method of treating a wound, reducing a scar, or repairing skin in a subject in need of such treatment, reduction, or repair, the method comprising administering to the subject a compound of claim 1 or a pharmaceutically acceptable salt thereof.

10. The method of claim 9, the method comprising administering to the subject an effective amount of a compound of claim 1 or a pharmaceutically acceptable salt thereof.

11. A compound selected from the group consisting of:

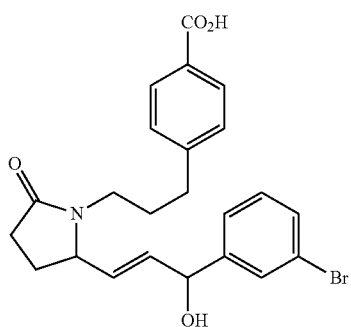

and

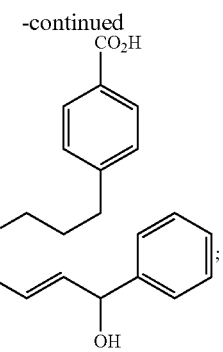

or pharmaceutically acceptable salts thereof.

12. The compound of claim 1, wherein:
Y is O;
Z is $CH_2$;
Q is phenyl substituted with one $R^6$;
U is phenyl or thiophenyl, wherein the phenyl or thiophenyl is optionally substituted with one $R^7$;
V is phenyl optionally substituted with one or more $R^8$;
$R^1$ is —OH;
$R^2$ is H;
each $R^3$, $R^4$ and $R^5$ is H;
$R^6$ is —$CO_2H$;
$R^7$ is halo;
each $R^8$ is independently $C_1$-$C_6$ alkyl, haloalkyl, hydroxyalkyl, hydroxyl, or halo; and
m is 1; and
wherein the dashed line represents the presence of a bond, and wherein the resulting olefin geometry is trans;
or a pharmaceutically acceptable salt thereof.

* * * * *

UNITED STATES PATENT AND TRADEMARK OFFICE
CERTIFICATE OF CORRECTION

PATENT NO. : 9,540,357 B1
APPLICATION NO. : 14/501760
DATED : January 10, 2017
INVENTOR(S) : Vinh X. Ngo et al.

It is certified that error appears in the above-identified patent and that said Letters Patent is hereby corrected as shown below:

On the Title Page

In Column 2, in item (57) "Abstract", Line 4, delete "and or" and insert -- and/or --, therefor.

In the Specification

In Column 2, Line 38, delete "S:" and insert -- S; --, therefor.

In Column 2, Line 39, delete "S:" and insert -- S; --, therefor.

In Column 2, Line 41, delete "$R^6$:" and insert -- $R^6$; --, therefor.

In Column 2, Line 43, delete "$R^7$:" and insert -- $R^7$; --, therefor.

In Column 2, Line 45, delete "$R^8$:" and insert -- $R^8$; --, therefor.

In Column 2, Line 46, delete "alkyl:" and insert -- alkyl; --, therefor.

In Column 2, Line 47, delete "alkyl:" and insert -- alkyl; --, therefor.

In Column 2, Line 51, delete "heteroaryl:" and insert -- heteroaryl; --, therefor.

In Column 2, Lines 57-58, delete "heteroaryl:" and insert -- heteroaryl; --, therefor.

In Column 2, Line 60, delete "amino:" and insert -- amino; --, therefor.

In Column 2, Line 64, delete "1:" and insert -- 1; --, therefor.

In Column 2, Line 67, delete "trans:" and insert -- trans; --, therefor.

Signed and Sealed this
Twenty-sixth Day of June, 2018

Andrei Iancu
*Director of the United States Patent and Trademark Office*

CERTIFICATE OF CORRECTION (continued)
U.S. Pat. No. 9,540,357 B1

In Column 3, Line 2, delete "atoms:" and insert -- atoms; --, therefor.

In Column 3, Line 4, delete "1:" and insert -- 1; --, therefor.

In Column 3, Line 52, delete "meanings." and insert -- meanings: --, therefor.

In Column 4, Line 13, delete "chain:" and insert -- chain; --, therefor.

In Column 4, Line 34, delete "chain:" and insert -- chain; --, therefor.

In Column 4, Lines 39-46, delete ""Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl." and insert the same on Column 4, Line 38 as a continuation of the same paragraph.

In Column 6, Line 27, delete "like:" and insert -- like; --, therefor.

In Column 9, Line 40, delete "(2004):" and insert -- (2004); --, therefor.

In Column 10, Line 13, delete "tartarates," and insert -- tartrates, --, therefor.

In Column 10, Line 32, delete "quarternized" and insert -- quaternized --, therefor.

In Column 13, Line 13, delete "S:" and insert -- S; --, therefor.

In Column 13, Line 14, delete "S:" and insert -- S; --, therefor.

In Column 13, Line 16, delete "$R^6$:" and insert -- $R^6$; --, therefor.

In Column 13, Line 18, delete "$R^7$:" and insert -- $R^7$; --, therefor.

In Column 13, Line 20, delete "$R^8$:" and insert -- $R^8$; --, therefor.

In Column 13, Line 22, delete "alkyl:" and insert -- alkyl; --, therefor.

In Column 13, Line 23, delete "alkyl:" and insert -- alkyl; --, therefor.

In Column 13, Line 25, delete "$OR^e$," and insert -- $OR^e$, --, therefor.

In Column 13, Line 25, delete "$R^e$" and insert -- $R^e$ --, therefor.

In Column 13, Line 27, delete "heteroaryl:" and insert -- heteroaryl; --, therefor.

In Column 13, Lines 33-34, delete "heteroaryl:" and insert -- heteroaryl; --, therefor.

In Column 13, Line 36, delete "amino:" and insert -- amino; --, therefor.

In Column 13, Line 40, delete "1:" and insert -- 1; --, therefor.

In Column 13, Line 43, delete "trans:" and insert -- trans; --, therefor.

In Column 13, Line 45, delete "atoms:" and insert -- atoms; --, therefor.

In Column 13, Line 47, delete "1:" and insert -- 1; --, therefor.

In Column 13, Line 51, delete "O:" and insert -- O; --, therefor.

In Column 13, Line 52, delete "$CH_2$:" and insert -- $CH_2$; --, therefor.

In Column 13, Line 53, delete "H:" and insert -- H; --, therefor.

In Column 13, Line 54, delete "H:" and insert -- H; --, therefor.

In Column 13, Line 55, delete "H:" and insert -- H; --, therefor.

In Column 13, Line 57, delete "trans:" and insert -- trans; --, therefor.

In Column 13, Line 59, delete "atoms:" and insert -- atoms; --, therefor.

In Column 14, Line 14, delete "aryl:" and insert -- aryl; --, therefor.

In Column 14, Line 22, delete "aryl:" and insert -- aryl; --, therefor.

In Column 14, Line 24, delete "1:" and insert -- 1; --, therefor.

In Column 14, Line 28, delete "O:" and insert -- O; --, therefor.

In Column 14, Line 29, delete "$CH_2$:" and insert -- $CH_2$; --, therefor.

In Column 14, Line 32, delete "$R^6$:" and insert -- $R^6$; --, therefor.

In Column 14, Line 33, delete "H:" and insert -- H; --, therefor.

In Column 14, Line 34, delete "H:" and insert -- H; --, therefor.

In Column 14, Line 35, delete "H:" and insert -- H; --, therefor.

In Column 14, Line 37, delete "aryl:" and insert -- aryl; --, therefor.

CERTIFICATE OF CORRECTION (continued)
U.S. Pat. No. 9,540,357 B1

In Column 14, Line 39, delete "trans:" and insert -- trans; --, therefor.

In Column 14, Line 41, delete "atoms:" and insert -- atoms; --, therefor.

In Column 14, Line 42, delete "1:" and insert -- 1; --, therefor.

In Column 14, Line 64, delete "S:" and insert -- S; --, therefor.

In Column 14, Line 65, delete "S:" and insert -- S; --, therefor.

In Column 14, Line 67, delete "$R^6$:" and insert -- $R^6$; --, therefor.

In Column 15, Line 2, delete "$R^7$:" and insert -- $R^7$; --, therefor.

In Column 15, Line 3, delete "alkyl:" and insert -- alkyl; --, therefor.

In Column 15, Line 4, delete "alkyl:" and insert -- alkyl; --, therefor.

In Column 15, Line 6, delete "$OR^e$," and insert -- $OR^c$, --, therefor.

In Column 15, Line 6, delete "$R^e$" and insert -- $R^c$ --, therefor.

In Column 15, Line 8, delete "heteroaryl:" and insert -- heteroaryl; --, therefor.

In Column 15, Line 18, delete "amino:" and insert -- amino; --, therefor.

In Column 15, Line 21, delete "trans:" and insert -- trans; --, therefor.

In Column 15, Line 23, delete "atoms:" and insert -- atoms; --, therefor.

In Column 15, Line 27, delete "O:" and insert -- O; --, therefor.

In Column 15, Line 28, delete "$CH_2$:" and insert -- $CH_2$; --, therefor.

In Column 15, Line 29, delete "H:" and insert -- H; --, therefor.

In Column 15, Line 30, delete "H:" and insert -- H; --, therefor.

In Column 15, Line 31, delete "H:" and insert -- H; --, therefor.

In Column 15, Line 33, delete "trans:" and insert -- trans; --, therefor.

In Column 15, Line 35, delete "atoms:" and insert -- atoms; --, therefor.

In Column 15, Line 57, delete "aryl:" and insert -- aryl; --, therefor.

CERTIFICATE OF CORRECTION (continued)
U.S. Pat. No. 9,540,357 B1

In Column 15, Line 64, delete "aryl:" and insert -- aryl; --, therefor.

In Column 16, Line 1, delete "O:" and insert -- O; --, therefor.

In Column 16, Line 2, delete "$CH_2$:" and insert -- $CH_2$; --, therefor.

In Column 16, Line 4, delete "$R^6$:" and insert -- $R^6$; --, therefor.

In Column 16, Line 5, delete "H:" and insert -- H; --, therefor.

In Column 16, Line 6, delete "H:" and insert -- H; --, therefor.

In Column 16, Line 7, delete "H:" and insert -- H; --, therefor.

In Column 16, Line 9, delete "aryl:" and insert -- aryl; --, therefor.

In Column 16, Line 11, delete "trans:" and insert -- trans; --, therefor.

In Column 16, Line 13, delete "atoms:" and insert -- atoms; --, therefor.

In Column 16, Line 20, delete "S:" and insert -- S; --, therefor.

In Column 16, Line 21, delete "S:" and insert -- S; --, therefor.

In Column 16, Line 23, delete "$R^6$:" and insert -- $R^6$; --, therefor.

In Column 16, Line 25, delete "$R^7$:" and insert -- $R^7$; --, therefor.

In Column 16, Line 26, delete "alkyl:" and insert -- alkyl; --, therefor.

In Column 16, Line 27, delete "alkyl:" and insert -- alkyl; --, therefor.

In Column 16, Line 29, delete "$OR^e$," and insert -- $OR^c$, --, therefor.

In Column 16, Line 29, delete "$R^e$" and insert -- $R^c$ --, therefor.

In Column 16, Line 31, delete "heteroaryl:" and insert -- heteroaryl; --, therefor.

In Column 16, Line 40, delete "amino:" and insert -- amino; --, therefor.

In Column 16, Line 43, delete "trans:" and insert -- trans; --, therefor.

In Column 16, Line 45, delete "atoms:" and insert -- atoms; --, therefor.

In Column 16, Line 49, delete "O:" and insert -- O; --, therefor.

In Column 16, Line 50, delete "CH₂:" and insert -- CH$_2$; --, therefor.

In Column 16, Line 51, delete "H:" and insert -- H; --, therefor.

In Column 16, Line 52, delete "H:" and insert -- H; --, therefor.

In Column 16, Line 53, delete "H:" and insert -- H; --, therefor.

In Column 16, Line 55, delete "trans:" and insert -- trans; --, therefor.

In Column 16, Line 57, delete "atoms:" and insert -- atoms; --, therefor.

In Column 17, Line 12, delete "aryl:" and insert -- aryl; --, therefor.

In Column 17, Line 23, delete "O:" and insert -- O; --, therefor.

In Column 17, Line 24, delete "CH₂:" and insert -- CH$_2$; --, therefor.

In Column 17, Line 26, delete "R⁶:" and insert -- R$^6$; --, therefor.

In Column 17, Line 27, delete "H:" and insert -- H; --, therefor.

In Column 17, Line 28, delete "H:" and insert -- H; --, therefor.

In Column 17, Line 29, delete "H:" and insert -- H; --, therefor.

In Column 17, Line 31, delete "aryl:" and insert -- aryl; --, therefor.

In Column 17, Line 33, delete "trans:" and insert -- trans; --, therefor.

In Column 17, Line 35, delete "atoms:" and insert -- atoms; --, therefor.

In Column 17, Line 41, delete "S:" and insert -- S; --, therefor.

In Column 17, Line 42, delete "S:" and insert -- S; --, therefor.

In Column 17, Line 44, delete "R⁶:" and insert -- R$^6$; --, therefor.

In Column 17, Line 59, delete "amino:" and insert -- amino; --, therefor.

In Column 17, Line 61, delete "amino:" and insert -- amino; --, therefor.

In Column 17, Line 63, delete "amino:" and insert -- amino; --, therefor.

In Column 17, Line 65, delete "amino:" and insert -- amino; --, therefor.

CERTIFICATE OF CORRECTION (continued)

U.S. Pat. No. 9,540,357 B1

In Column 17, Line 67, delete "amino:" and insert -- amino; --, therefor.

In Column 18, Line 1, delete "alkyl:" and insert -- alkyl; --, therefor.

In Column 18, Line 2, delete "alkyl:" and insert -- alkyl; --, therefor.

In Column 18, Line 4, delete "OR$^e$," and insert -- OR$^c$, --, therefor.

In Column 18, Line 4, delete "R$^e$" and insert -- R$^c$ --, therefor.

In Column 18, Line 12-13, delete "heteroaryl:" and insert -- heteroaryl; --, therefor.

In Column 18, Line 16, delete "trans:" and insert -- trans; --, therefor.

In Column 18, Line 19, delete "atoms:" and insert -- atoms; --, therefor.

In Column 18, Line 23, delete "O:" and insert -- O; --, therefor.

In Column 18, Line 24, delete "CH$_2$:" and insert -- CH$_2$; --, therefor.

In Column 18, Line 25, delete "H:" and insert -- H; --, therefor.

In Column 18, Line 26, delete "H:" and insert -- H; --, therefor.

In Column 18, Line 27, delete "H:" and insert -- H; --, therefor.

In Column 18, Line 29, delete "trans:" and insert -- trans; --, therefor.

In Column 18, Line 31, delete "atoms:" and insert -- atoms; --, therefor.

In Column 18, Line 53, delete "aryl:" and insert -- aryl; --, therefor.

In Column 18, Line 64, delete "O:" and insert -- O; --, therefor.

In Column 18, Line 65, delete "CH$_2$:" and insert -- CH$_2$; --, therefor.

In Column 18, Line 67, delete "R$^6$:" and insert -- R$^6$; --, therefor.

In Column 19, Line 1, delete "H:" and insert -- H; --, therefor.

In Column 19, Line 2, delete "H:" and insert -- H; --, therefor.

In Column 19, Line 3, delete "H:" and insert -- H; --, therefor.

In Column 19, Line 5, delete "aryl:" and insert -- aryl; --, therefor.

CERTIFICATE OF CORRECTION (continued)
U.S. Pat. No. 9,540,357 B1

In Column 19, Line 7, delete "trans:" and insert -- trans; --, therefor.

In Column 19, Line 9, delete "atoms:" and insert -- atoms; --, therefor.

In Column 19, Line 17, delete "S:" and insert -- S; --, therefor.

In Column 19, Line 18, delete "S:" and insert -- S; --, therefor.

In Column 19, Line 20, delete "$R^6$:" and insert -- $R^6$; --, therefor.

In Column 19, Line 22, delete "$R^7$:" and insert -- $R^7$; --, therefor.

In Column 19, Line 23, delete "alkyl:" and insert -- alkyl; --, therefor.

In Column 19, Line 24, delete "alkyl:" and insert -- alkyl; --, therefor.

In Column 19, Line 26, delete "$OR^e$," and insert -- $OR^e$, --, therefor.

In Column 19, Line 26, delete "$R^e$" and insert -- $R^e$ --, therefor.

In Column 19, Line 28, delete "heteroaryl:" and insert -- heteroaryl; --, therefor.

In Column 19, Line 38, delete "amino:" and insert -- amino; --, therefor.

In Column 19, Line 41, delete "trans:" and insert -- trans; --, therefor.

In Column 19, Line 43, delete "atoms:" and insert -- atoms; --, therefor.

In Column 19, Line 47, delete "O:" and insert -- O; --, therefor.

In Column 19, Line 48, delete "$CH_2$:" and insert -- $CH_2$; --, therefor.

In Column 19, Line 49, delete "H:" and insert -- H; --, therefor.

In Column 19, Line 50, delete "H:" and insert -- H; --, therefor.

In Column 19, Line 51, delete "H:" and insert -- H; --, therefor.

In Column 19, Line 54, delete "trans:" and insert -- trans; --, therefor.

In Column 19, Line 56, delete "atoms:" and insert -- atoms; --, therefor.

In Column 20, Line 12, delete "aryl:" and insert -- aryl; --, therefor.

In Column 20, Line 22, delete "O:" and insert -- O; --, therefor.

CERTIFICATE OF CORRECTION (continued)
U.S. Pat. No. 9,540,357 B1

In Column 20, Line 23, delete "CH$_2$:" and insert -- CH$_2$; --, therefor.

In Column 20, Line 25, delete "R$^6$:" and insert -- R$^6$; --, therefor.

In Column 20, Line 26, delete "H:" and insert -- H; --, therefor.

In Column 20, Line 27, delete "H:" and insert -- H; --, therefor.

In Column 20, Line 28, delete "H:" and insert -- H; --, therefor.

In Column 20, Line 30, delete "aryl:" and insert -- aryl; --, therefor.

In Column 20, Line 32, delete "trans:" and insert -- trans; --, therefor.

In Column 20, Line 34, delete "atoms:" and insert -- atoms; --, therefor.

In Column 20, Line 40, delete "S:" and insert -- S; --, therefor.

In Column 20, Line 41, delete "S:" and insert -- S; --, therefor.

In Column 20, Line 43, delete "R$^6$:" and insert -- R$^6$; --, therefor.

In Column 20, Line 46, delete "R$^7$:" and insert -- R$^7$; --, therefor.

In Column 20, Line 47, delete "alkyl:" and insert -- alkyl; --, therefor.

In Column 20, Line 48, delete "alkyl:" and insert -- alkyl; --, therefor.

In Column 20, Line 50, delete "OR$^e$," and insert -- OR$^c$, --, therefor.

In Column 20, Line 50, delete "R$^e$" and insert -- R$^c$ --, therefor.

In Column 20, Line 52, delete "heteroaryl:" and insert -- heteroaryl; --, therefor.

In Column 20, Line 61, delete "amino:" and insert -- amino; --, therefor.

In Column 20, Line 64, delete "trans:" and insert -- trans; --, therefor.

In Column 20, Line 66, delete "atoms:" and insert -- atoms; --, therefor.

In Column 21, Line 3, delete "O:" and insert -- O; --, therefor.

In Column 21, Line 4, delete "CH$_2$:" and insert -- CH$_2$; --, therefor.

In Column 21, Line 7, delete "R$^7$:" and insert -- R$^7$; --, therefor.

CERTIFICATE OF CORRECTION (continued)
U.S. Pat. No. 9,540,357 B1

In Column 21, Line 8, delete "H:" and insert -- H; --, therefor.

In Column 21, Line 9, delete "H:" and insert -- H; --, therefor.

In Column 21, Line 10, delete "H:" and insert -- H; --, therefor.

In Column 21, Line 12, delete "amino:" and insert -- amino; --, therefor.

In Column 21, Line 14, delete "trans:" and insert -- trans; --, therefor.

In Column 21, Line 16, delete "atoms:" and insert -- atoms; --, therefor.

In Column 21, Line 38, delete "aryl:" and insert -- aryl; --, therefor.

In Column 21, Line 49, delete "O:" and insert -- O; --, therefor.

In Column 21, Line 50, delete "$CH_2$:" and insert -- $CH_2$; --, therefor.

In Column 21, Line 52, delete "$R^6$:" and insert -- $R^6$; --, therefor.

In Column 21, Line 53, delete "H:" and insert -- H; --, therefor.

In Column 21, Line 54, delete "H:" and insert -- H; --, therefor.

In Column 21, Line 55, delete "H:" and insert -- H; --, therefor.

In Column 21, Line 57, delete "aryl:" and insert -- aryl; --, therefor.

In Column 21, Line 59, delete "trans:" and insert -- trans; --, therefor.

In Column 21, Line 61, delete "atoms:" and insert -- atoms; --, therefor.

In Column 22, Line 13, delete "S:" and insert -- S; --, therefor.

In Column 22, Line 14, delete "S:" and insert -- S; --, therefor.

In Column 22, Line 17, delete "$R^6$:" and insert -- $R^6$; --, therefor.

In Column 22, Line 19, delete "$R^7$:" and insert -- $R^7$; --, therefor.

In Column 22, Line 21, delete "$R^8$:" and insert -- $R^8$; --, therefor.

In Column 22, Line 22, delete "alkyl:" and insert -- alkyl; --, therefor.

In Column 22, Line 23, delete "alkyl:" and insert -- alkyl; --, therefor.

In Column 22, Line 25, delete "OR$^e$," and insert -- OR$^c$, --, therefor.

In Column 22, Line 25, delete "R$^e$" and insert -- R$^c$ --, therefor.

In Column 22, Line 27, delete "heteroaryl:" and insert -- heteroaryl; --, therefor.

In Column 22, Lines 33-34, delete "heteroaryl:" and insert -- heteroaryl; --, therefor.

In Column 22, Lines 39-40, delete "heteroaryl:" and insert -- heteroaryl; --, therefor.

In Column 22, Line 43, delete "trans:" and insert -- trans; --, therefor.

In Column 22, Line 45, delete "atoms:" and insert -- atoms; --, therefor.

In Column 22, Line 49, delete "O:" and insert -- O; --, therefor.

In Column 22, Line 50, delete "CH$_2$:" and insert -- CH$_2$; --, therefor.

In Column 22, Line 51, delete "H:" and insert -- H; --, therefor.

In Column 22, Line 52, delete "H:" and insert -- H; --, therefor.

In Column 22, Line 53, delete "H:" and insert -- H; --, therefor.

In Column 22, Line 55, delete "trans:" and insert -- trans; --, therefor.

In Column 22, Line 57, delete "atoms:" and insert -- atoms; --, therefor.

In Column 23, Line 12, delete "aryl:" and insert -- aryl; --, therefor.

In Column 23, Line 23, delete "O:" and insert -- O; --, therefor.

In Column 23, Line 24, delete "CH$_2$:" and insert -- CH$_2$; --, therefor.

In Column 23, Line 27, delete "R$^6$:" and insert -- R$^6$; --, therefor.

In Column 23, Line 28, delete "H:" and insert -- H; --, therefor.

In Column 23, Line 29, delete "H:" and insert -- H; --, therefor.

In Column 23, Line 30, delete "H:" and insert -- H; --, therefor.

In Column 23, Line 32, delete "aryl:" and insert -- aryl; --, therefor.

In Column 23, Line 34, delete "trans:" and insert -- trans; --, therefor.

In Column 23, Line 36, delete "atoms:" and insert -- atoms; --, therefor.

In Column 23, Line 42, delete "S:" and insert -- S; --, therefor.

In Column 23, Line 43, delete "S:" and insert -- S; --, therefor.

In Column 23, Line 45, delete "$R^6$:" and insert -- $R^6$; --, therefor.

In Column 23, Line 47, delete "$R^7$:" and insert -- $R^7$; --, therefor.

In Column 23, Line 49, delete "$R^8$:" and insert -- $R^8$; --, therefor.

In Column 23, Line 50, delete "alkyl:" and insert -- alkyl; --, therefor.

In Column 23, Line 51, delete "alkyl:" and insert -- alkyl; --, therefor.

In Column 23, Line 52, delete "$OR^e$," and insert -- $OR^e$, --, therefor.

In Column 23, Line 52, delete "$R^e$" and insert -- $R^e$ --, therefor.

In Column 23, Line 55, delete "heteroaryl:" and insert -- heteroaryl; --, therefor.

In Column 23, Lines 61-62, delete "heteroaryl:" and insert -- heteroaryl; --, therefor.

In Column 23, Lines 66-67, delete "heteroaryl:" and insert -- heteroaryl; --, therefor.

In Column 24, Line 3, delete "trans:" and insert -- trans; --, therefor.

In Column 24, Line 5, delete "atoms:" and insert -- atoms; --, therefor.

In Column 24, Line 9, delete "O:" and insert -- O; --, therefor.

In Column 24, Line 10, delete "$CH_2$:" and insert -- $CH_2$; --, therefor.

In Column 24, Line 11, delete "H:" and insert -- H; --, therefor.

In Column 24, Line 12, delete "H:" and insert -- H; --, therefor.

In Column 24, Line 13, delete "H:" and insert -- H; --, therefor.

In Column 24, Line 15, delete "trans:" and insert -- trans; --, therefor.

In Column 24, Line 18, delete "atoms:" and insert -- atoms; --, therefor.

In Column 24, Line 40, delete "aryl:" and insert -- aryl; --, therefor.

In Column 24, Line 51, delete "O:" and insert -- O; --, therefor.

In Column 24, Line 52, delete "CH$_2$:" and insert -- CH$_2$; --, therefor.

In Column 24, Line 55, delete "R$^6$:" and insert -- R$^6$; --, therefor.

In Column 24, Line 56, delete "H:" and insert -- H; --, therefor.

In Column 24, Line 57, delete "H:" and insert -- H; --, therefor.

In Column 24, Line 58, delete "H:" and insert -- H; --, therefor.

In Column 24, Line 60, delete "aryl:" and insert -- aryl; --, therefor.

In Column 24, Line 62, delete "trans:" and insert -- trans; --, therefor.

In Column 24, Line 64, delete "atoms:" and insert -- atoms; --, therefor.

In Column 25, Line 3, delete "S:" and insert -- S; --, therefor.

In Column 25, Line 4, delete "S:" and insert -- S; --, therefor.

In Column 25, Line 6, delete "R$^6$:" and insert -- R$^6$; --, therefor.

In Column 25, Line 28, delete "amino:" and insert -- amino; --, therefor.

In Column 25, Line 30, delete "amino:" and insert -- amino; --, therefor.

In Column 25, Line 32, delete "amino:" and insert -- amino; --, therefor.

In Column 25, Line 34, delete "amino:" and insert -- amino; --, therefor.

In Column 25, Line 36, delete "R$^8$:" and insert -- R$^8$; --, therefor.

In Column 25, Line 37, delete "alkyl:" and insert -- alkyl; --, therefor.

In Column 25, Line 38, delete "alkyl:" and insert -- alkyl; --, therefor.

In Column 25, Line 40, delete "OR$^e$," and insert -- OR$^e$, --, therefor.

In Column 25, Line 40, delete "R$^e$" and insert -- R$^e$ --, therefor.

In Column 25, Line 42, delete "heteroaryl:" and insert -- heteroaryl; --, therefor.

In Column 25, Lines 51-52, delete "heteroaryl:" and insert -- heteroaryl; --, therefor.

In Column 25, Line 55, delete "trans:" and insert -- trans; --, therefor.

In Column 25, Line 57, delete "atoms:" and insert -- atoms; --, therefor.

In Column 25, Line 61, delete "O:" and insert -- O; --, therefor.

In Column 25, Line 62, delete "CH$_2$:" and insert -- CH$_2$; --, therefor.

In Column 25, Line 63, delete "H:" and insert -- H; --, therefor.

In Column 25, Line 64, delete "H:" and insert -- H; --, therefor.

In Column 25, Line 65, delete "H:" and insert -- H; --, therefor.

In Column 25, Line 67, delete "trans:" and insert -- trans; --, therefor.

In Column 26, Line 2, delete "atoms:" and insert -- atoms; --, therefor.

In Column 26, Line 24, delete "aryl:" and insert -- aryl; --, therefor.

In Column 26, Line 36, delete "O:" and insert -- O; --, therefor.

In Column 26, Line 37, delete "CH$_2$:" and insert -- CH$_2$; --, therefor.

In Column 26, Line 40, delete "R$^6$:" and insert -- R$^6$; --, therefor.

In Column 26, Line 41, delete "H:" and insert -- H; --, therefor.

In Column 26, Line 42, delete "H:" and insert -- H; --, therefor.

In Column 26, Line 43, delete "H:" and insert -- H; --, therefor.

In Column 26, Line 48, delete "trans:" and insert -- trans; --, therefor.

In Column 26, Line 50, delete "atoms:" and insert -- atoms; --, therefor.

In Column 26, Line 56, delete "S:" and insert -- S; --, therefor.

In Column 26, Line 57, delete "S:" and insert -- S; --, therefor.

In Column 26, Line 59, delete "R$^6$:" and insert -- R$^6$; --, therefor.

In Column 26, Line 61, delete "R$^7$:" and insert -- R$^7$; --, therefor.

In Column 26, Line 63, delete "R$^8$:" and insert -- R$^8$; --, therefor.

In Column 26, Line 64, delete "alkyl:" and insert -- alkyl; --, therefor.

In Column 26, Line 65, delete "alkyl:" and insert -- alkyl; --, therefor.

In Column 26, Line 67, delete "$OR^e$," and insert -- $OR^e$, --, therefor.

In Column 26, Line 67, delete "$R^e$" and insert -- $R^e$ --, therefor.

In Column 27, Line 2, delete "heteroaryl:" and insert -- heteroaryl; --, therefor.

In Column 27, Lines 8-9, delete "heteroaryl:" and insert -- heteroaryl; --, therefor.

In Column 27, Lines 13-14, delete "heteroaryl:" and insert -- heteroaryl; --, therefor.

In Column 27, Line 17, delete "trans:" and insert -- trans; --, therefor.

In Column 27, Line 20, delete "atoms:" and insert -- atoms; --, therefor.

In Column 27, Line 24, delete "O:" and insert -- O; --, therefor.

In Column 27, Line 25, delete "$CH_2$:" and insert -- $CH_2$; --, therefor.

In Column 27, Line 26, delete "H:" and insert -- H; --, therefor.

In Column 27, Line 27, delete "H:" and insert -- H; --, therefor.

In Column 27, Line 28, delete "H:" and insert -- H; --, therefor.

In Column 27, Line 31, delete "trans:" and insert -- trans; --, therefor.

In Column 27, Line 33, delete "atoms:" and insert -- atoms; --, therefor.

In Column 27, Line 56, delete "aryl:" and insert -- aryl; --, therefor.

In Column 28, Line 1, delete "O:" and insert -- O; --, therefor.

In Column 28, Line 2, delete "$CH_2$:" and insert -- $CH_2$; --, therefor.

In Column 28, Line 5, delete "$R^6$:" and insert -- $R^6$; --, therefor.

In Column 28, Line 6, delete "H:" and insert -- H; --, therefor.

In Column 28, Line 7, delete "H:" and insert -- H; --, therefor.

In Column 28, Line 8, delete "H:" and insert -- H; --, therefor.

In Column 28, Line 10, delete "aryl:" and insert -- aryl; --, therefor.

In Column 28, Line 12, delete "trans:" and insert -- trans; --, therefor.

In Column 28, Line 14, delete "atoms:" and insert -- atoms; --, therefor.

In Column 28, Line 20, delete "S:" and insert -- S; --, therefor.

In Column 28, Line 21, delete "S:" and insert -- S; --, therefor.

In Column 28, Line 23, delete "$R^6$:" and insert -- $R^6$; --, therefor.

In Column 28, Line 26, delete "$R^7$:" and insert -- $R^7$; --, therefor.

In Column 28, Line 28, delete "$R^8$:" and insert -- $R^8$; --, therefor.

In Column 28, Line 29, delete "alkyl:" and insert -- alkyl; --, therefor.

In Column 28, Line 30, delete "alkyl:" and insert -- alkyl; --, therefor.

In Column 28, Line 32, delete "$OR^e$," and insert -- $OR^e$, --, therefor.

In Column 28, Line 32, delete "$R^e$" and insert -- $R^e$ --, therefor.

In Column 28, Line 34, delete "heteroaryl:" and insert -- heteroaryl; --, therefor.

In Column 28, Line 42, delete "amino:" and insert -- amino; --, therefor.

In Column 28, Line 45, delete "trans:" and insert -- trans; --, therefor.

In Column 28, Line 47, delete "atoms:" and insert -- atoms; --, therefor.

In Column 28, Line 51, delete "O:" and insert -- O; --, therefor.

In Column 28, Line 52, delete "$CH^2$:" and insert -- $CH^2$; --, therefor.

In Column 28, Line 53, delete "H:" and insert -- H; --, therefor.

In Column 28, Line 54, delete "H:" and insert -- H; --, therefor.

In Column 28, Line 55, delete "H:" and insert -- H; --, therefor.

In Column 28, Line 57, delete "trans:" and insert -- trans; --, therefor.

In Column 28, Line 59, delete "atoms:" and insert -- atoms; --, therefor.

In Column 28, Line 66, delete "aryl:" and insert -- aryl; --, therefor.

In Column 29, Line 14, delete "aryl:" and insert -- aryl; --, therefor.

In Column 29, Line 21, delete "aryl:" and insert -- aryl; --, therefor.

In Column 29, Line 25, delete "O:" and insert -- O; --, therefor.

In Column 29, Line 26, delete "$CH_2$:" and insert -- $CH_2$; --, therefor.

In Column 29, Line 29, delete "$R^6$:" and insert -- $R^6$; --, therefor.

In Column 29, Line 30, delete "H:" and insert -- H; --, therefor.

In Column 29, Line 31, delete "H:" and insert -- H; --, therefor.

In Column 29, Line 32, delete "H:" and insert -- H; --, therefor.

In Column 29, Line 34, delete "aryl:" and insert -- aryl; --, therefor.

In Column 29, Line 36, delete "trans:" and insert -- trans; --, therefor.

In Column 29, Line 38, delete "atoms:" and insert -- atoms; --, therefor.

In Column 29, Line 45, delete "S:" and insert -- S; --, therefor.

In Column 29, Line 46, delete "S:" and insert -- S; --, therefor.

In Column 29, Line 48, delete "$R^6$:" and insert -- $R^6$; --, therefor.

In Column 29, Line 50, delete "$R^7$:" and insert -- $R^7$; --, therefor.

In Column 29, Line 52, delete "$R^8$:" and insert -- $R^8$; --, therefor.

In Column 29, Line 53, delete "alkyl:" and insert -- alkyl; --, therefor.

In Column 29, Line 54, delete "alkyl:" and insert -- alkyl; --, therefor.

In Column 29, Line 56, delete "$OR^e$," and insert -- $OR^e$, --, therefor.

In Column 29, Line 56, delete "$R^e$" and insert -- $R^e$ --, therefor.

In Column 29, Line 58, delete "heteroaryl:" and insert -- heteroaryl; --, therefor.

In Column 29, Lines 64-65, delete "heteroaryl:" and insert -- heteroaryl; --, therefor.

In Column 30, Lines 2-3, delete "heteroaryl:" and insert -- heteroaryl; --, therefor.

In Column 30, Line 6, delete "trans:" and insert -- trans; --, therefor.

In Column 30, Line 8, delete "atoms:" and insert -- atoms; --, therefor.

In Column 30, Line 12, delete "O:" and insert -- O; --, therefor.

In Column 30, Line 13, delete "$CH_2$:" and insert -- $CH_2$; --, therefor.

In Column 30, Line 14, delete "H:" and insert -- H; --, therefor.

In Column 30, Line 15, delete "H:" and insert -- H; --, therefor.

In Column 30, Line 16, delete "H:" and insert -- H; --, therefor.

In Column 30, Line 18, delete "trans:" and insert -- trans; --, therefor.

In Column 30, Line 20, delete "atoms:" and insert -- atoms; --, therefor.

In Column 30, Line 42, delete "aryl:" and insert -- aryl; --, therefor.

In Column 30, Line 53, delete "O:" and insert -- O; --, therefor.

In Column 30, Line 54, delete "$CH_2$:" and insert -- $CH_2$; --, therefor.

In Column 30, Line 57, delete "$R^6$:" and insert -- $R^6$; --, therefor.

In Column 30, Line 58, delete "H:" and insert -- H; --, therefor.

In Column 30, Line 59, delete "H:" and insert -- H; --, therefor.

In Column 30, Line 60, delete "H:" and insert -- H; --, therefor.

In Column 30, Line 62, delete "aryl:" and insert -- aryl; --, therefor.

In Column 30, Line 64, delete "trans:" and insert -- trans; --, therefor.

In Column 30, Line 66, delete "atoms:" and insert -- atoms; --, therefor.

In Column 31, Line 6, delete "S:" and insert -- S; --, therefor.

In Column 31, Line 7, delete "S:" and insert -- S; --, therefor.

In Column 31, Line 9, delete "$R^6$:" and insert -- $R^6$; --, therefor.

CERTIFICATE OF CORRECTION (continued)
U.S. Pat. No. 9,540,357 B1

In Column 31, Line 32, delete "amino:" and insert -- amino; --, therefor.

In Column 31, Line 34, delete "amino:" and insert -- amino; --, therefor.

In Column 31, Line 37, delete "amino:" and insert -- amino; --, therefor.

In Column 31, Line 39, delete "amino:" and insert -- amino; --, therefor.

In Column 31, Line 41, delete "$R^8$:" and insert -- $R^8$; --, therefor.

In Column 31, Line 42, delete "alkyl:" and insert -- alkyl; --, therefor.

In Column 31, Line 43, delete "alkyl:" and insert -- alkyl; --, therefor.

In Column 31, Line 46, delete "$OR^e$," and insert -- $OR^e$, --, therefor.

In Column 31, Line 46, delete "$R^e$" and insert -- $R^e$ --, therefor.

In Column 31, Line 48, delete "heteroaryl:" and insert -- heteroaryl; --, therefor.

In Column 31, Lines 57-58, delete "heteroaryl:" and insert -- heteroaryl; --, therefor.

In Column 31, Line 61, delete "trans:" and insert -- trans; --, therefor.

In Column 31, Line 63, delete "atoms:" and insert -- atoms; --, therefor.

In Column 32, Line 1, delete "O:" and insert -- O; --, therefor.

In Column 32, Line 2, delete "$CH_2$:" and insert -- $CH_2$; --, therefor.

In Column 32, Line 3, delete "H:" and insert -- H; --, therefor.

In Column 32, Line 4, delete "H:" and insert -- H; --, therefor.

In Column 32, Line 5, delete "H:" and insert -- H; --, therefor.

In Column 32, Line 7, delete "trans:" and insert -- trans; --, therefor.

In Column 32, Line 9, delete "atoms:" and insert -- atoms; --, therefor.

In Column 32, Line 31, delete "aryl:" and insert -- aryl; --, therefor.

In Column 32, Line 42, delete "O:" and insert -- O; --, therefor.

In Column 32, Line 43, delete "$CH_2$:" and insert -- $CH_2$; --, therefor.

In Column 32, Line 46, delete "R⁶:" and insert -- $R^6$; --, therefor.

In Column 32, Line 47, delete "H:" and insert -- H; --, therefor.

In Column 32, Line 48, delete "H:" and insert -- H; --, therefor.

In Column 32, Line 49, delete "H:" and insert -- H; --, therefor.

In Column 32, Line 51, delete "aryl:" and insert -- aryl; --, therefor.

In Column 32, Line 53, delete "trans:" and insert -- trans; --, therefor.

In Column 32, Line 55, delete "atoms:" and insert -- atoms; --, therefor.

In Column 32, Line 62, delete "S:" and insert -- S; --, therefor.

In Column 32, Line 63, delete "S:" and insert -- S; --, therefor.

In Column 32, Line 65, delete "R⁶:" and insert -- $R^6$; --, therefor.

In Column 32, Line 67, delete "R⁷:" and insert -- $R^7$; --, therefor.

In Column 33, Line 2, delete "R⁸:" and insert -- $R^8$; --, therefor.

In Column 33, Line 3, delete "alkyl:" and insert -- alkyl; --, therefor.

In Column 33, Line 4, delete "alkyl:" and insert -- alkyl; --, therefor.

In Column 33, Line 6, delete "OR$^e$," and insert -- OR$^c$, --, therefor.

In Column 33, Line 6, delete "R$^e$" and insert -- R$^c$ --, therefor.

In Column 33, Line 8, delete "heteroaryl:" and insert -- heteroaryl; --, therefor.

In Column 33, Line 14-15, delete "heteroaryl:" and insert -- heteroaryl; --, therefor.

In Column 33, Line 19-20, delete "heteroaryl:" and insert -- heteroaryl; --, therefor.

In Column 33, Line 23, delete "trans:" and insert -- trans; --, therefor.

In Column 33, Line 25, delete "atoms:" and insert -- atoms; --, therefor.

In Column 33, Line 29, delete "O:" and insert -- O; --, therefor.

In Column 33, Line 30, delete "$CH_2$:" and insert -- $CH_2$; --, therefor.

In Column 33, Line 31, delete "H:" and insert -- H; --, therefor.

In Column 33, Line 32, delete "H:" and insert -- H; --, therefor.

In Column 33, Line 33, delete "H:" and insert -- H; --, therefor.

In Column 33, Line 35, delete "trans:" and insert -- trans; --, therefor.

In Column 33, Line 37, delete "atoms:" and insert -- atoms; --, therefor.

In Column 33, Line 59, delete "aryl:" and insert -- aryl; --, therefor.

In Column 34, Line 3, delete "O:" and insert -- O; --, therefor.

In Column 34, Line 4, delete "CH$_2$:" and insert -- CH$_2$; --, therefor.

In Column 34, Line 7, delete "R$^6$:" and insert -- R$^6$; --, therefor.

In Column 34, Line 8, delete "H:" and insert -- H; --, therefor.

In Column 34, Line 9, delete "H:" and insert -- H; --, therefor.

In Column 34, Line 10, delete "H:" and insert -- H; --, therefor.

In Column 34, Line 12, delete "aryl:" and insert -- aryl; --, therefor.

In Column 34, Line 14, delete "trans:" and insert -- trans; --, therefor.

In Column 34, Line 17, delete "atoms:" and insert -- atoms; --, therefor.

In Column 34, Line 24, delete "S:" and insert -- S; --, therefor.

In Column 34, Line 25, delete "S:" and insert -- S; --, therefor.

In Column 34, Line 37, delete "R$^6$:" and insert -- R$^6$; --, therefor.

In Column 34, Line 30, delete "R$^7$:" and insert -- R$^7$; --, therefor.

In Column 34, Line 32, delete "R$^8$:" and insert -- R$^8$; --, therefor.

In Column 34, Line 33, delete "alkyl:" and insert -- alkyl; --, therefor.

In Column 34, Line 34, delete "alkyl:" and insert -- alkyl; --, therefor.

In Column 34, Line 36, delete "OR$^c$," and insert -- OR$^c$, --, therefor.

In Column 34, Line 36, delete "R$^e$:" and insert -- R$^c$ --, therefor.

In Column 34, Line 38, delete "heteroaryl:" and insert -- heteroaryl; --, therefor.

In Column 34, Line 47, delete "amino:" and insert -- amino; --, therefor.

In Column 34, Line 50, delete "trans:" and insert -- trans; --, therefor.

In Column 34, Line 52, delete "atoms:" and insert -- atoms; --, therefor.

In Column 34, Line 56, delete "O:" and insert -- O; --, therefor.

In Column 34, Line 57, delete "CH$_2$:" and insert -- CH$_2$; --, therefor.

In Column 34, Line 58, delete "H:" and insert -- H; --, therefor.

In Column 34, Line 59, delete "H:" and insert -- H; --, therefor.

In Column 34, Line 60, delete "H:" and insert -- H; --, therefor.

In Column 34, Line 62, delete "trans:" and insert -- trans; --, therefor.

In Column 34, Line 64, delete "atoms:" and insert -- atoms; --, therefor.

In Column 35, Line 20, delete "aryl:" and insert -- aryl; --, therefor.

In Column 35, Line 32, delete "O:" and insert -- O; --, therefor.

In Column 35, Line 33, delete "CH$_2$:" and insert -- CH$_2$; --, therefor.

In Column 35, Line 37, delete "R$^6$:" and insert -- R$^6$; --, therefor.

In Column 35, Line 38, delete "H:" and insert -- H; --, therefor.

In Column 35, Line 39, delete "H:" and insert -- H; --, therefor.

In Column 35, Line 40, delete "H:" and insert -- H; --, therefor.

In Column 35, Line 42, delete "aryl:" and insert -- aryl; --, therefor.

In Column 35, Line 44, delete "trans:" and insert -- trans; --, therefor.

In Column 35, Line 47, delete "atoms:" and insert -- atoms; --, therefor.

In Column 35, Line 52, delete "S:" and insert -- S; --, therefor.

CERTIFICATE OF CORRECTION (continued)

In Column 35, Line 53, delete "S:" and insert -- S; --, therefor.

In Column 35, Line 55, delete "R6:" and insert -- R6; --, therefor.

In Column 36, Line 13, delete "amino:" and insert -- amino; --, therefor.

In Column 36, Line 15, delete "amino:" and insert -- amino; --, therefor.

In Column 36, Line 17, delete "amino:" and insert -- amino; --, therefor.

In Column 36, Line 19, delete "amino:" and insert -- amino; --, therefor.

In Column 36, Line 34, delete "heteroaryl:" and insert -- heteroaryl; --, therefor.

In Column 36, Line 36, delete "heteroaryl:" and insert -- heteroaryl; --, therefor.

In Column 36, Line 38, delete "heteroaryl:" and insert -- heteroaryl; --, therefor.

In Column 36, Line 40, delete "heteroaryl:" and insert -- heteroaryl; --, therefor.

In Column 36, Line 42, delete "heteroaryl:" and insert -- heteroaryl; --, therefor.

In Column 36, Line 43, delete "alkyl:" and insert -- alkyl; --, therefor.

In Column 36, Line 44, delete "alkyl:" and insert -- alkyl; --, therefor.

In Column 36, Line 46, delete "$OR^e$," and insert -- $OR^c$, --, therefor.

In Column 36, Line 46, delete "$R^e$" and insert -- $R^c$ --, therefor.

In Column 36, Line 49, delete "heteroaryl:" and insert -- heteroaryl; --, therefor.

In Column 36, Lines 58-59, delete "heteroaryl:" and insert -- heteroaryl; --, therefor.

In Column 36, Line 62, delete "trans:" and insert -- trans; --, therefor.

In Column 36, Line 64, delete "atoms:" and insert -- atoms; --, therefor.

In Column 37, Line 1, delete "O:" and insert -- O; --, therefor.

In Column 37, Line 2, delete "$CH_2$:" and insert -- $CH_2$; --, therefor.

In Column 37, Line 3, delete "H:" and insert -- H; --, therefor.

In Column 37, Line 4, delete "H:" and insert -- H; --, therefor.

CERTIFICATE OF CORRECTION (continued)
U.S. Pat. No. 9,540,357 B1

In Column 37, Line 5, delete "H:" and insert -- H; --, therefor.

In Column 37, Line 7, delete "trans:" and insert -- trans; --, therefor.

In Column 37, Line 9, delete "atoms:" and insert -- atoms; --, therefor.

In Column 37, Line 36, delete "aryl:" and insert -- aryl; --, therefor.

In Column 37, Line 47, delete "O:" and insert -- O; --, therefor.

In Column 37, Line 48, delete "CH$_2$:" and insert -- CH$_2$; --, therefor.

In Column 37, Line 51, delete "R$^6$:" and insert -- R$^6$; --, therefor.

In Column 37, Line 52, delete "H:" and insert -- H; --, therefor.

In Column 37, Line 53, delete "H:" and insert -- H; --, therefor.

In Column 37, Line 54, delete "H:" and insert -- H; --, therefor.

In Column 37, Line 56, delete "aryl:" and insert -- aryl; --, therefor.

In Column 37, Line 58, delete "trans:" and insert -- trans; --, therefor.

In Column 37, Line 60, delete "atoms:" and insert -- atoms; --, therefor.

In Column 37, Line 64, delete "S:" and insert -- S; --, therefor.

In Column 37, Line 65, delete "S:" and insert -- S; --, therefor.

In Column 37, Line 67, delete "R$^6$:" and insert -- R$^6$; --, therefor.

In Column 38, Line 15, delete "amino:" and insert -- amino; --, therefor.

In Column 38, Line 17, delete "amino:" and insert -- amino; --, therefor.

In Column 38, Line 19, delete "amino:" and insert -- amino; --, therefor.

In Column 38, Line 21, delete "amino:" and insert -- amino; --, therefor.

In Column 38, Line 36, delete "heteroaryl:" and insert -- heteroaryl; --, therefor.

In Column 38, Line 38, delete "heteroaryl:" and insert -- heteroaryl; --, therefor.

In Column 38, Line 40, delete "heteroaryl:" and insert -- heteroaryl; --, therefor.

In Column 38, Line 42, delete "heteroaryl:" and insert -- heteroaryl; --, therefor.

In Column 38, Line 44, delete "heteroaryl:" and insert -- heteroaryl; --, therefor.

In Column 38, Line 45, delete "alkyl:" and insert -- alkyl; --, therefor.

In Column 38, Line 46, delete "alkyl:" and insert -- alkyl; --, therefor.

In Column 38, Line 49, delete "$OR^e$," and insert -- $OR^c$, --, therefor.

In Column 38, Line 49, delete "$R^e$" and insert -- $R^c$ --, therefor.

In Column 38, Line 51, delete "heteroaryl:" and insert -- heteroaryl; --, therefor.

In Column 38, Line 61, delete "trans:" and insert -- trans; --, therefor.

In Column 38, Line 64, delete "atoms:" and insert -- atoms; --, therefor.

In Column 39, Line 1, delete "O:" and insert -- O; --, therefor.

In Column 39, Line 2, delete "$CH_2$:" and insert -- $CH_2$; --, therefor.

In Column 39, Line 3, delete "H:" and insert -- H; --, therefor.

In Column 39, Line 4, delete "H:" and insert -- H; --, therefor.

In Column 39, Line 5, delete "H:" and insert -- H; --, therefor.

In Column 39, Line 7, delete "trans:" and insert -- trans; --, therefor.

In Column 39, Line 9, delete "atoms:" and insert -- atoms; --, therefor.

In Column 39, Line 37, delete "aryl:" and insert -- aryl; --, therefor.

In Column 39, Line 49, delete "O:" and insert -- O; --, therefor.

In Column 39, Line 50, delete "$CH_2$:" and insert -- $CH_2$; --, therefor.

In Column 39, Line 53, delete "$R^6$:" and insert -- $R^6$; --, therefor.

In Column 39, Line 54, delete "H:" and insert -- H; --, therefor.

In Column 39, Line 55, delete "H:" and insert -- H; --, therefor.

In Column 39, Line 56, delete "H:" and insert -- H; --, therefor.

In Column 39, Line 59, delete "aryl:" and insert -- aryl; --, therefor.

In Column 39, Line 61, delete "trans:" and insert -- trans; --, therefor.

In Column 39, Line 63, delete "atoms:" and insert -- atoms; --, therefor.

In Column 39, Line 67, delete "1c:" and insert -- Ic: --, therefor.

In Column 40, Line 25, delete "amino:" and insert -- amino; --, therefor.

In Column 40, Line 27, delete "amino:" and insert -- amino; --, therefor.

In Column 40, Line 29, delete "amino:" and insert -- amino; --, therefor.

In Column 40, Line 31, delete "amino:" and insert -- amino; --, therefor.

In Column 40, Line 33, delete "heteroaryl:" and insert -- heteroaryl; --, therefor.

In Column 40, Line 35, delete "heteroaryl:" and insert -- heteroaryl; --, therefor.

In Column 40, Line 37, delete "heteroaryl:" and insert -- heteroaryl; --, therefor.

In Column 40, Line 39, delete "$R^{83}$" and insert -- $R^{8e}$ --, therefor.

In Column 40, Line 40, delete "heteroaryl:" and insert -- heteroaryl; --, therefor.

In Column 40, Line 43, delete "1d:" and insert -- Id: --, therefor.

In Column 41, Line 2, delete "amino:" and insert -- amino; --, therefor.

In Column 41, Line 4, delete "amino:" and insert -- amino; --, therefor.

In Column 41, Line 6, delete "amino:" and insert -- amino; --, therefor.

In Column 41, Line 8, delete "amino:" and insert -- amino; --, therefor.

In Column 41, Line 9, delete "$R^{sa}$" and insert -- $R^{8a}$ --, therefor.

In Column 41, Line 10, delete "heteroaryl:" and insert -- heteroaryl; --, therefor.

In Column 41, Line 12, delete "heteroaryl:" and insert -- heteroaryl; --, therefor.

In Column 41, Line 14, delete "heteroaryl:" and insert -- heteroaryl; --, therefor.

In Column 41, Line 17, delete "heteroaryl:" and insert -- heteroaryl; --, therefor.

CERTIFICATE OF CORRECTION (continued)
U.S. Pat. No. 9,540,357 B1

In Column 50, Line 31, delete "antipyrin," and insert -- antipyrine, --, therefor.

In Column 50, Line 37, delete "chrondroitin" and insert -- chondroitin --, therefor.

In Column 50, Line 38, delete "Inamarin," and insert -- linamarin, --, therefor.

In Column 51, Line 27, delete "flavanonse" and insert -- flavanones --, therefor.

In Column 51, Line 32, delete "tannis," and insert -- tannins, --, therefor.

In Column 51, Line 32, delete "tannis," and insert -- tannins, --, therefor.

In Column 51, Line 33, delete "tannis." and insert -- tannins. --, therefor.

In Column 64, Line 64, after "dimethylsilane" insert -- . --.

In Column 78, Line 25, delete "Whatman" and insert -- whatman --, therefor.

In the Claims

In Column 100, Line 42, in Claim 5, delete "1c:" and insert -- Ic: --, therefor.